United States Patent
Cooke et al.

(10) Patent No.: US 8,357,679 B2
(45) Date of Patent: Jan. 22, 2013

(54) HEXAFLUOROISOPROPANOL DERIVATIVES

(75) Inventors: Andrew John Cooke, Newhouse (GB); Andrew Stanley Edwards, Newhouse (GB); Fiona Elizabeth Andrews, Newhouse (GB); David Jonathan Bennett, Newhouse (GB); Olaf Nimz, Newhouse (GB); Emma Louise Carswell, Newhouse (GB)

(73) Assignee: MSD Oss B.V., Oss (NL)

( * ) Notice: Subject to any disclaimer, the term of this patent is extended or adjusted under 35 U.S.C. 154(b) by 304 days.

(21) Appl. No.: 12/465,134

(22) Filed: May 13, 2009

(65) Prior Publication Data

US 2010/0029621 A1 Feb. 4, 2010

Related U.S. Application Data

(60) Provisional application No. 61/053,454, filed on May 15, 2008.

(30) Foreign Application Priority Data

May 15, 2008 (EP) ..................................... 08156246

(51) Int. Cl.
| | |
|---|---|
| A61K 31/50 | (2006.01) |
| A61K 31/55 | (2006.01) |
| A61K 31/4965 | (2006.01) |
| A61K 31/497 | (2006.01) |
| A61K 31/51 | (2006.01) |
| A01N 43/54 | (2006.01) |
| C07D 239/02 | (2006.01) |
| C07D 243/00 | (2006.01) |
| C07D 403/00 | (2006.01) |
| C07D 241/04 | (2006.01) |
| C07D 295/00 | (2006.01) |

(52) U.S. Cl. .............. 514/218; 514/252.01; 514/252.12; 514/255.01; 514/255.02; 514/275; 540/492; 544/238; 544/332; 544/384; 544/389; 544/399; 544/400

(58) Field of Classification Search ............. 514/252.12, 514/255.01, 255.02; 544/384, 389, 399, 544/400
See application file for complete search history.

(56) References Cited

U.S. PATENT DOCUMENTS

2006/0074115 A1 4/2006 Dehmlow et al.
2009/0030015 A1* 1/2009 Kranich et al. .......... 514/255.01

FOREIGN PATENT DOCUMENTS

| EP | 0742208 | 11/1996 |
|---|---|---|
| WO | WO00/54759 | 9/2000 |
| WO | WO02/058690 | 8/2002 |
| WO | WO2004/048334 | 6/2004 |
| WO | WO2006/037480 | 4/2006 |
| WO | WO2007/051920 | 5/2007 |
| WO | WO2009/138438 | 11/2009 |
| WO | WO2011/051282 | 5/2011 |

OTHER PUBLICATIONS

International Search Report (PCT/EP2009/055790) mail date Aug. 11, 2009, 3 pages.
Written Opinion (PCT/EP2009/055790) mail date Aug. 11, 2009, 5 pages.
Bennett, et. al.; "An update on non-steroidal liver X receptor agaonists and their potential use in the treatment of atherosclerosis"; Expert Opinion On Therapeutic Patents, vol. 16; No. 12; 2006; pp. 1673-1699.
Levin, Nancy, et. al.; " Macrophage Liver X Receptor is Required for Antiatherogenic Activity of LXR Agonists"; Arterioscler Thromb Vasc Biol; Jan. 2005; pp. 135-142.
Joseph, Sean B.; et. al.; "Reciprocal regulation of inflammation and lipid metabolism by liver X receptors", Nature Medicine, vol. 9, No. 2; pp. 213-219, (2003).
Laffitte, Bryan A, et. al. "Activation of liver X receptor improves glucose tolerance through coordinate regulation of glucose metabolism in liver and adipose tissue", Proceedings Natl Acad Sci, vol. 100, No. 9, pp. 5419-5424, (2003).
International Search Report (PCT/EP2010/066157) mail date Mar. 2, 2011, 2 pages.

* cited by examiner

*Primary Examiner* — Erich A Leeser
(74) *Attorney, Agent, or Firm* — James L. McGinnis; Catherine D. Fitch

(57) ABSTRACT

The present invention relates to hexafluoroisopropanol derivatives having the general formula I Formula I

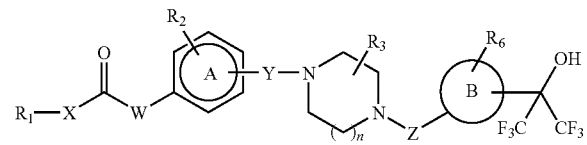

to pharmaceutical compositions comprising the same and to the use of these hexafluoroisopropanol derivatives in the treatment of atherosclerosis.

12 Claims, No Drawings

HEXAFLUOROISOPROPANOL DERIVATIVES

This application is a non-provisional application that claims priority under 35 U.S.C. §119(e) of provisional application U.S. Ser. No. 61/053,454 filed May 15, 2008, the contents of which are hereby incorporated by reference in its entirety.

BACKGROUND

The present invention relates to hexafluoroisopropanol derivatives, to pharmaceutical compositions comprising the same and to the use of these hexafluoroisopropanol derivatives in the treatment of atherosclerosis.

The Liver X Receptors (LXRs) are a family of nuclear receptors that are activated upon binding of the naturally occurring oxysterols inducing transcription of target genes. Two subtypes of LXR ($\alpha$ and $\beta$) have been identified and exhibit 77% homology of both their ligand- and DNA-binding domains. Both subtypes are highly conserved between humans and rodents however their tissue expression patterns differ significantly. The expression of LXR$\alpha$ is restricted to tissues involved in lipid metabolism with highest expression in the liver; there are also significant levels in kidney, spleen, small intestine and adipose tissue. LXR$\beta$ is very widely distributed and has been found in virtually every tissue examined, including liver and brain. Both LXR$\beta$ and LXR$\beta$ are expressed in macrophages. See Costet et al., *J. Biol. Chem.* 275:28240-28245 (2000).

The roles of the LXR receptors are not fully understood, however LXR is well established as a master regulator of lipid metabolism in the liver and peripheral tissues, and as the key inducer of the ATP-binding cassette transporter A1 (ABCA1) gene (Venkateswaran et al., *Proc. Natl. Acad. Sci. USA.* 97:12097-12102 (2000)). In the human population, mutations of the ABCA1 gene lead to highly atherogenic lipoprotein profiles (Singaraja et al., *Arterioscier. Thromb. Vasc. Biol.* 23:1322-1332 (2003)) which in the most severe form cause Tangier's Disease and associated premature atherosclerosis, (see Bodzioch et al., *Nat. Genet.* 22:347-351 (1999) and Rust et al., *Nat. Genet.* 22:352-355 (1999)). This rare inherited disorder is characterised by very low levels of high density lipoproteins (HDL), macrophage accumulation of cholesterol esters and significantly increased risk of atherosclerotic disease (Brooks-Wilson et al., *Nat. Genet.* 22:336-345 (1999)). Evidence has demonstrated that up-regulation of ABCA1 in human macrophages and enterocytes of the small intestine, is mediated by LXR activation (Costet et al., supra). Furthermore, LXR agonists have also been shown to promote cholesterol efflux. See Claudel et al., *Proc. Natl. Acad. Sci. USA.* 98:2610-2615 (2001). LXR receptors therefore play a critical role in cholesterol homeostasis in macrophages, and suppression within the local environment of the advanced atherosclerotic plaque may be a key feature of the pathology of the disease.

The potential utility of LXR agonists in the treatment of atherosclerosis has been increasingly documented over the last few years. See for example Levin et al., *Arterioscler. Thromb. Vasc. Biol.* 25:135-142 (2005). Atherosclerosis is a disease of the arteries that exists for many years without causing symptoms. Advanced atherosclerotic plaques can however become vulnerable to rupture, promoting acute thrombosis and clinical events such as myocardial infarction (MI) and stroke. The primary cell type implicated in rupture of atherosclerotic plaques, and subsequent clinical events, is the macrophage. The primary mechanism for achieving efficacy in atherosclerosis with an LXR agonist is expected to occur by lowering the cholesterol burden of arteries (via upregulation of ABCA1), to generate more stable lesions and thus reduce the clinical events. Additionally, LXR agonists may increase circulating HDL levels due to the role of ABCA1 in generation of nascent HDL by the liver. There is potential for further anti-atherosclerotic effects of LXR agonists due to suppression of inflammation (Joseph et al., *Nat. Med.* 9:213-219 (2003)) and effects on glucose metabolism. See Latiffe et al., *Proc. Natl. Acad. Sci. USA.* 100:5419-24 (2003).

The first compounds specifically identified as LXR agonists for the treatment of atherosclerosis were disclosed by Tularik, Inc. (International Patent Application WO 00/54759) and contain the hexafluoroisopropanol group. Since then a number of different chemotypes have been identified as LXR agonists (for a review see: Bennett et al. Expert Opin. Ther. Patents 16, 1673-1699, 2006).

There is a remaining need for compounds that are effective as LXR modulators.

To this aim the present invention provides hexafluoroisopropanol derivatives having the general Formula I

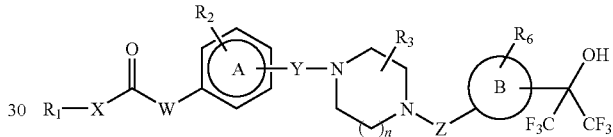

Formula I wherein

B represents a five or six membered aromatic ring which is substituted at a carbon atom by a hexafluoroisopropanol moiety, the ring optionally comprising one or two nitrogens, sulphur or oxygen;

n is 1 or 2;

Z is $CH_2$ or CO;

Y is CO, $SO_2$, $CH_2$ or a bond; and can be of meta or para substitution pattern;

A is a 6-membered aromatic ring optionally containing 1 or 2 nitrogen atoms;

X is $NR_4$, O or a bond;

W is NH, O or $CH_2$;

$R_1$ is $(C_{1-8})$alkyl, $(C_{3-8})$cycloalkyl or $(C_{3-8})$cycloalkyl($C_{1-4}$) alkyl, each of the alkyl groups being optionally substituted with hydroxyl, hydroxymethyl, $(C_{1-3})$alkyloxy, cyano, halogen, $CF_3$, $NR_7R_8$, $NR_7R_8CO$ or $R_9OCO$; or $R_1$ is 5- or 6-membered aromatic ring, optionally comprising 1-3 heteroatoms selected from O, S and N, the ring being optionally substituted by $(C_{1-3})$alkyl, $(C_{3-6})$cycloalkyl, $(C_{1-3})$alkyloxy, $(C_{1-3})$alkylsulfonyl, cyano, $CF_3$, $OCF_3$, halogen or $R_9OCO$, and the ring being optionally linked to X via a $(C_{1-3})$alkylene group which is optionally substituted by hydroxyl; or $R_1$ is a 5- or 6-membered saturated or unsaturated heterocyclic ring, comprising 1 or 2 heteroatoms selected from $NR_{10}$, O, S, SO and $SO_2$, the ring being optionally substituted by $(C_{1-3})$alkyl, hydroxyl, oxo, $NR_{11}R_{12}CH_2$ or $R_9OCO$, and the ring being optionally linked to X via a $(C_{1-3})$alkylene group which is optionally substituted by hydroxyl; or when X is $NR_4$, $R_1$ may together with $R_4$ and the N to which they are bonded form a 4-8 membered ring, which can be optionally substituted with hydroxyl or hydroxymethyl;

$R_2$ optionally represents 1-3 substituents independently selected from $(C_{1-4})$alkyl, $(C_{1-4})$alkyloxy, $CF_3$, $OCF_3$ and halogen;

$R_3$ optionally represents 1-4 substituents independently selected from $(C_{1-4})$alkyl and $(C_{1-4})$alkyl substituted by OH or 1 or more halogens; or $R_3$ represents oxo or $COOR_5$;

$R_4$, when present is H or $(C_{1-3})$alkyl;

$R_5$, when present is H or $(C_{1-3})$alkyl;

$R_6$, when present is H or $(C_{1-3})$alkyl;

$R_7$ and $R_8$, when present, are independently H, $(C_{1-3})$alkyl or $(C_{3-5})$cycloalkyl;

$R_9$, when present, is H, $(C_{1-3})$alkyl or $(C_{3-5})$cycloalkyl$(C_{1-3})$alkyl;

$R_{10}$, when present, is H, $(C_{1-3})$alkyl or $CO(C_{1-3})$alkyl;

$R_{11}$ and $R_{12}$, when present, are independently H or $(C_{1-3})$alkyl;

or a pharmaceutically acceptable salt thereof.

In one aspect the invention provides hexafluoroisopropanol derivatives having the general Formula II

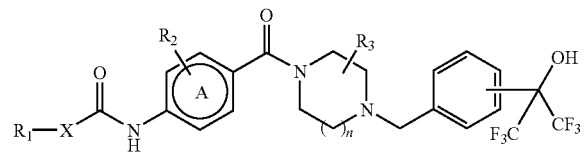

Formula II wherein n is 1 or 2;

A is a 6-membered aromatic ring optionally containing 1 or 2 nitrogen atoms;

X is $NR_4$, O or a bond;

$R_1$ is $(C_{1-8})$alkyl, $(C_{3-8})$cycloalkyl or $(C_{3-8})$cycloalkyl$(C_{1-4})$alkyl, each of the alkyl groups being optionally substituted with hydroxyl or hydroxymethyl; or when X is $NR_4$, $R_1$, may together with $R_4$ and the N to which they are bonded form a 4-8 membered ring, which can be optionally substituted with hydroxyl or hydroxymethyl;

$R_2$ optionally represents 1-3 substituents independently selected from $(C_{1-4})$alkyl, $(C_{1-4})$alkyloxy, $CF_3$ and halogen;

$R_3$ optionally represents 1-4 substituents independently selected from $(C_{1-4})$alkyl and $(C_{1-4})$alkyl substituted by OH or 1 or more halogens;

$R_4$, when present is H or $(C_{1-3})$alkyl;

or a pharmaceutically acceptable salt thereof.

Compounds according to Formula II correspond to certain of the compounds of Formula I wherein W represents NH, Y represents CO, Z represents $CH_2$, and ring B represents phenyl.

N-Benzyl, N'-arylcarbonylpiperazine derivatives, which are structurally related to the compounds of the present invention, have been disclosed in U.S. Pat. No. 5,286,728 (Ciba Geigy AG) as inhibitors of the biosynthesis of interleukin-1 (IL-1), useful in the treatment of diseases in which excess production of IL-1 plays a role, such as in inflammatory disorders.

The term $(C_{1-8})$alkyl as used in the definition of Formula I means a branched or unbranched alkyl group having 1-8 carbon atoms, like octyl, hexyl, pentyl, isopentyl, butyl, isobutyl, tertiary butyl, propyl, isopropyl, ethyl and methyl.

The term $(C_{1-4})$alkyl as used in the definition of Formula I means a branched or unbranched alkyl group having 1-4 carbon atoms, like butyl, isobutyl, tertiary butyl, propyl, isopropyl, ethyl and methyl.

Likewise, the term $(C_{1-3})$alkyl used in the definition of Formula I means a branched or un-branched alkyl group having 1-3 carbon atoms, like propyl, isopropyl, ethyl and methyl.

The term $(C_{3-8})$cycloalkyl means a cycloalkyl group having 3-8 carbon atoms, like cycloheptyl, cyclohexyl, cyclopentyl, cyclobutyl and cyclopropyl.

In the term $(C_{3-8})$cycloalkyl$(C_{1-4})$alkyl, $(C_{3-8})$cycloalkyl and $(C_{1-4})$alkyl have the meaning as given above. In addition the term $(C_{3-8})$cycloalkyl$(C_{1-4})$alkyl encompasses compounds in which one of the cycloalkyl carbon atom is a spiro-carbon atom, such as 2-methyl-2-cyclopropylethyl and (1-methylcyclobutyl)methyl and the like.

The term $(C_{1-3})$alkylene means an alkanediyl functional group such as methylene, 1,2-ethanediyl, 1,3-propanediyl or 2-propanediyl.

The term 5- or 6-membered aromatic ring, optionally comprising 1-3 heteroatoms selected from O, S and N, as used in the definition of $R_1$ is exemplified by ring systems such as phenyl, pyridine-2-yl, pyridine-3-yl, pyridine-4-yl, pyrazin-2-yl, pyrimidin-4-yl, 1H-pyrazol-5-yl, pyridazin-4-yl, furan-2-yl, thien-2-yl, oxazol-3-yl, thiazol-2-yl, 1,3,4-thiaziazol-2-yl, 1,2,4-thiadiazol-5-yl, 1,2,4-oxadiazol-5-yl and the like.

The term 5- or 6-membered saturated or unsaturated heterocyclic ring, comprising 1 or 2 heteroatoms selected from $NR_{10}$, O, S, SO and $SO_2$, as used in the definition of $R_1$ is exemplified by tetrahydro-2H-pyran-4-yl, tetrahydro-2H-furan-2-yl, tetrahydrothiophen-3-yl, imidazolidin-1-yl, morpholin-1-yl, pyrrolidin-1-yl, piperidinyl, pyrrolidinyl, 1,2-dioxo-tetrahydro-1$\lambda^6$-thiophen-3-yl and the like.

The term a five or six membered aromatic ring optionally comprising one or two nitrogens, sulphur or oxygen, as used in the definition of ring B, is exemplified by phenyl, thiazolyl, oxazolyl, pyridinyl, pyrazinyl, pyrimidinyl, 1H-pyrazolyl, thienyl, oxazoyl, thiazolyl, thiazolyl, thiadiazolyl, oxadiazolyl and the like. The preferred group B is phenyl. In these preferred compounds the hexafluoroisopropanol moiety at the phenyl group of the compounds of Formula I can be positioned at either the ortho, the meta or the para position, the para-position being the preferred one.

The term halogen means F, Cl, Br or I.

There is a preference for hexafluoroisopropanol derivatives of Formula I wherein B represents substituted phenyl.

Further preferred are the hexafluoroisopropanol derivatives of Formula I wherein Z is $CH_2$, Y is CO, W is NH, X is NH and n is 1.

Also preferred are hexafluoroisopropanol derivatives of Formula I, wherein in addition A is a phenyl ring and Y and W are in para-position to each other.

More preferred are the compounds of Formula I wherein $R_2$ represents F or Cl ortho to the W=NH-position; and wherein $R_3$ and $R_6$ are absent.

Particular hexafluoroisopropanol derivatives of the invention are:

1-(cyclopropylmethyl)-3-(4-(4-(4-(1,1,1,3,3,3-hexafluoro-2-hydroxypropan-2-yl)benzyl)-piperazine-1-carbonyl) phenyl)urea;

1-butyl-3-(4-(4-(4-(1,1,1,3,3,3-hexafluoro-2-hydroxypropan-2-yl)benzyl)piperazine-1-carbonyl)phenyl)urea;

1-(4-(4-(4-(1,1,1,3,3,3-hexafluoro-2-hydroxypropan-2-yl)
benzyl)piperazine-1-carbonyl)phenyl)-3-isobutylurea;

1-cyclobutyl-3-(4-(4-(4-(1,1,1,3,3,3-hexafluoro-2-hydroxypropan-2-yl)benzyl)piperazine-1-carbonyl)phenyl)urea;

1-(2-fluoro-4-(4-(4-(1,1,1,3,3,3-hexafluoro-2-hydroxypropan-2-yl)benzyl)piperazine-1-carbonyl)phenyl)-3-(2-hydroxy-2-methylpropyl)urea;

1-(2-fluoro-4-(4-(4-(1,1,1,3,3,3-hexafluoro-2-hydroxypropan-2-yl)benzyl)piperazine-1-carbonyl)phenyl)-3-(3-hydroxy-3-methylbutyl)urea;

1-(cyclopropylmethyl)-3-(2-fluoro-4-(4-(4-(1,1,1,3,3,3-hexafluoro-2-hydroxypropan-2-yl)benzyl)piperazine-1-carbonyl)phenyl)urea;

(S)-1-(2-fluoro-4-(4-(4-(1,1,1,3,3,3-hexafluoro-2-hydroxypropan-2-yl)benzyl)piperazine-1-carbonyl)phenyl)-3-(2-hydroxypropyl)urea;

(R)-1-(2-fluoro-4-(4-(4-(1,1,1,3,3,3-hexafluoro-2-hydroxypropan-2-yl)benzyl)piperazine-1-carbonyl)phenyl)-3-(2-hydroxypropyl)urea;

1-(2-fluoro-4-(4-(4-(1,1,1,3,3,3-hexafluoro-2-hydroxypropan-2-yl)benzyl)piperazine-1-carbonyl)phenyl)-3-((1-hydroxycyclopropyl)methyl)urea;

(S)-1-(2-fluoro-4-(4-(4-(1,1,1,3,3,3-hexafluoro-2-hydroxypropan-2-yl)benzyl)piperazine-1-carbonyl)phenyl)-3-(1-hydroxy-3-methylbutan-2-yl)urea;

1-(2-fluoro-4-(4-(4-(1,1,1,3,3,3-hexafluoro-2-hydroxypropan-2-yl)benzyl)piperazine-1-carbonyl)phenyl)-3-(4-hydroxycyclohexyl)urea, trans;

(S)-1-(2-fluoro-4-(4-(4-(1,1,1,3,3,3-hexafluoro-2-hydroxypropan-2-yl)benzyl)piperazine-1-carbonyl)phenyl)-3-(1-hydroxypentan-2-yl)urea;

1-(2-chloro-4-(4-(4-(1,1,1,3,3,3-hexafluoro-2-hydroxypropan-2-yl)benzyl)piperazine-1-carbonyl)phenyl)-3-(2-hydroxy-2-methylpropyl)urea;

(S)-1-(2-chloro-4-(4-(4-(1,1,1,3,3,3-hexafluoro-2-hydroxypropan-2-yl)benzyl)piperazine-1-carbonyl)phenyl)-3-(2-hydroxypropyl)urea;

(R)-1-(2-chloro-4-(4-(4-(1,1,1,3,3,3-hexafluoro-2-hydroxypropan-2-yl)benzyl)piperazine-1-carbonyl)phenyl)-3-(2-hydroxypropyl)urea;

1-(2-chloro-4-(4-(4-(1,1,1,3,3,3-hexafluoro-2-hydroxypropan-2-yl)benzyl)piperazine-1-carbonyl)phenyl)-3-(3-hydroxy-3-methylbutyl)urea;

1-(2-chloro-4-(4-(4-(1,1,1,3,3,3-hexafluoro-2-hydroxypropan-2-yl)benzyl)piperazine-1-carbonyl)phenyl)-3-((1-hydroxycyclopropyl)methyl)urea; and 1-(2-chloro-4-(4-(4-(1,1,1,3,3,3-hexafluoro-2-hydroxypropan-2-yl)benzyl)piperazine-1-carbonyl)phenyl)-3-(4-hydroxycyclohexyl)urea, trans;

1-(2-amino-2-methylpropyl)-3-(2-fluoro-4-(4-(4-(1,1,1,3,3,3-hexafluoro-2-hydroxypropan-2-yl)benzyl)piperazine-1-carbonyl)phenyl)urea;

1-(2-fluoro-4-(4-(4-(1,1,1,3,3,3-hexafluoro-2-hydroxypropan-2-yl)benzyl)piperazine-1-carbonyl)phenyl)-3-((1S,2R)-2-hydroxycyclopentyl)urea;

1-(2-fluoro-4-(4-(4-(1,1,1,3,3,3-hexafluoro-2-hydroxypropan-2-yl)benzyl)piperazine-1-carbonyl)phenyl)-3-(3-hydroxycyclobutyl)urea, trans;

1-(2-fluoro-4-(4-(4-(1,1,1,3,3,3-hexafluoro-2-hydroxypropan-2-yl)benzyl)piperazine-1-carbonyl)phenyl)-3-((1-hydroxycyclobutyl)methyl)urea;

1-(2-(dimethylamino)-2-methylpropyl)-3-(2-fluoro-4-(4-(4-(1,1,1,3,3,3-hexafluoro-2-hydroxypropan-2-yl)benzyl)piperazine-1-carbonyl)phenyl)urea;

1-(2-fluoro-4-(4-(4-(1,1,1,3,3,3-hexafluoro-2-hydroxypropan-2-yl)benzyl)piperazine-1-carbonyl)phenyl)-3-(3,3,3-trifluoro-2-hydroxypropyl)urea;

1-(2-fluoro-4-(4-(4-(1,1,1,3,3,3-hexafluoro-2-hydroxypropan-2-yl)benzyl)piperazine-1-carbonyl)phenyl)-3-(tetrahydro-2H-pyran-4-yl)urea;

(R)-1-(2-fluoro-4-(4-(4-(1,1,1,3,3,3-hexafluoro-2-hydroxypropan-2-yl)benzyl)piperazine-1-carbonyl)phenyl)-3-(2-hydroxy-2-phenylethyl)urea;

(S)-1-(2-fluoro-4-(4-(4-(1,1,1,3,3,3-hexafluoro-2-hydroxypropan-2-yl)benzyl)piperazine-1-carbonyl)phenyl)-3-(2-hydroxy-2-phenylethyl)urea;

(S)-1-(2-fluoro-4-(4-(4-(1,1,1,3,3,3-hexafluoro-2-hydroxypropan-2-yl)benzyl)piperazine-1-carbonyl)phenyl)-3-(6-oxopiperidin-3-yl)urea;

1-(2-fluoro-4-{4-[4-(2,2,2-trifluoro-1-hydroxy-1-trifluoromethyl-ethyl)-benzyl]-piperazine-1-carbonyl}-phenyl)-3-(4-hydroxy-1,1-dioxo-tetrahydro-1$\lambda^6$-thiophen-3-yl)-urea, cis racemate;

1-(1,1-dioxo-tetrahydro-1$\lambda^6$-thiophen-3-yl)-3-(2-fluoro-4-{4-[4-(2,2,2-trifluoro-1-hydroxy-1-trifluoromethyl-ethyl)-benzyl]-piperazine-1-carbonyl}-phenyl)-urea;

(R)-1-(2-fluoro-4-(4-(4-(1,1,1,3,3,3-hexafluoro-2-hydroxypropan-2-yl)benzyl)piperazine-1-carbonyl)phenyl)-3-(tetrahydrofuran-3-yl)urea;

1-(1,1-dioxo-hexahydro-1$\lambda^6$-thiopyran-4-yl)-3-(2-fluoro-4-{4-[4-(2,2,2-trifluoro-1-hydroxy-1-trifluoromethyl-ethyl)-benzyl]-piperazine-1-carbonyl}-phenyl)-urea;

1-(2-fluoro-4-(4-(4-(1,1,1,3,3,3-hexafluoro-2-hydroxypropan-2-yl)benzyl)piperazine-1-carbonyl)phenyl)-3-((4-hydroxytetrahydro-2H-pyran-4-yl)methyl)urea;

(S)-1-(2-fluoro-4-(4-(4-(1,1,1,3,3,3-hexafluoro-2-hydroxypropan-2-yl)benzyl)piperazine-1-carbonyl)phenyl)-3-(tetrahydrofuran-3-yl)urea;

1-(2-fluoro-4-(4-(4-(1,1,1,3,3,3-hexafluoro-2-hydroxypropan-2-yl)benzyl)piperazine-1-carbonyl)phenyl)-3-(4-hydroxytetrahydrofuran-3-yl)urea, cis racemate;

1-(2-fluoro-4-(4-(4-(1,1,1,3,3,3-hexafluoro-2-hydroxypropan-2-yl)benzyl)piperazine-1-carbonyl)phenyl)-3-((1S,2R)-2-hydroxycyclohexyl)urea, cis racemate;

1-(2-fluoro-4-(4-(4-(1,1,1,3,3,3-hexafluoro-2-hydroxypropan-2-yl)benzyl)piperazine-1-carbonyl)phenyl)-3-(2-hydroxybutyl)urea, racemate;

1-(2-chloro-4-{4-[4-FA(2,2,2-trifluoro-1-hydroxy-1-trifluoromethyl-ethyl)-benzyl]-piperazine-1-carbonyl}-phenyl)-3-(4-hydroxy-1,1-dioxo-tetrahydro-1$\lambda^6$-thiophen-3-yl)-urea, cis racemate;

1-(5-tert-butylisoxazol-3-yl)-3-(2-fluoro-4-(4-(4-(1,1,1,3,3,3-hexafluoro-2-hydroxypropan-2-yl)benzyl)piperazine-1-carbonyl)phenyl)urea;

1-(2-fluoro-4-(4-(4-(1,1,1,3,3,3-hexafluoro-2-hydroxypropan-2-yl)benzyl)piperazine-1-carbonyl)phenyl)-3-(2-methylpyridin-4-yl)urea;

1-(2-fluoro-4-(4-(4-(1,1,1,3,3,3-hexafluoro-2-hydroxypropan-2-yl)benzyl)piperazine-1-carbonyl)phenyl)-3-(2-(trifluoromethyl)pyridin-4-yl)urea;

1-(2-fluoro-4-(4-(4-(1,1,1,3,3,3-hexafluoro-2-hydroxypropan-2-yl)benzyl)piperazine-1-carbonyl)phenyl)-3-(5-methylisoxazol-3-yl)urea;

1-(2-fluoro-4-(4-(4-(1,1,1,3,3,3-hexafluoro-2-hydroxypropan-2-yl)benzyl)piperazine-1-carbonyl)phenyl)-3-(3-fluoropyridin-4-yl)urea;

1-(2-fluoro-4-(4-(4-(1,1,1,3,3,3-hexafluoro-2-hydroxypropan-2-yl)benzyl)piperazine-1-carbonyl)phenyl)-3-(1,3,4-thiadiazol-2-yl)urea;

1-(2-fluoro-4-(4-(4-(1,1,1,3,3,3-hexafluoro-2-hydroxypropan-2-yl)benzyl)piperazine-1-carbonyl)phenyl)-3-(pyridin-4-yl)urea;
1-(2-fluoro-4-(4-(4-(1,1,1,3,3,3-hexafluoro-2-hydroxypropan-2-yl)benzyl)piperazine-1-carbonyl)phenyl)-3-(isoxazol-3-yl)urea;
1-(5-cyanothiazol-2-yl)-3-(2-fluoro-4-(4-(4-(1,1,1,3,3,3-hexafluoro-2-hydroxypropan-2-yl)benzyl)piperazine-1-carbonyl)phenyl)urea;
1-(2-fluoro-4-(4-(4-(1,1,1,3,3,3-hexafluoro-2-hydroxypropan-2-yl)benzyl)piperazine-1-carbonyl)phenyl)-3-(isoxazol-4-yl)urea;
1-(2-fluoro-4-(4-(4-(1,1,1,3,3,3-hexafluoro-2-hydroxypropan-2-yl)benzyl)piperazine-1-carbonyl)phenyl)-3-(pyridin-2-yl)urea;
1-(2-fluoro-4-(4-(4-(1,1,1,3,3,3-hexafluoro-2-hydroxypropan-2-yl)benzyl)piperazine-1-carbonyl)phenyl)-3-(3-methylisoxazol-5-yl)urea;
1-(2-fluoro-4-(4-(4-(1,1,1,3,3,3-hexafluoro-2-hydroxypropan-2-yl)benzyl)piperazine-1-carbonyl)phenyl)-3-(3-methyl-1,2,4-oxadiazol-5-yl)urea;
1-(2-fluoro-4-(4-(4-(1,1,1,3,3,3-hexafluoro-2-hydroxypropan-2-yl)benzyl)piperazine-1-carbonyl)phenyl)-3-(pyridin-3-yl)urea;
1-(2-fluoro-4-(4-(4-(1,1,1,3,3,3-hexafluoro-2-hydroxypropan-2-yl)benzyl)piperazine-1-carbonyl)phenyl)-3-(pyrimidin-4-yl)urea;
1-(2-fluoro-4-(4-(4-(1,1,1,3,3,3-hexafluoro-2-hydroxypropan-2-yl)benzyl)piperazine-1-carbonyl)phenyl)-3-(pyrazin-2-yl)urea;
1-(2-fluoro-4-{4-[4-(2,2,2-trifluoro-1-hydroxy-1-trifluoromethyl-ethyl)-benzyl]-piperazine-1-carbonyl}-phenyl)-3-(1-oxo-tetrahydro-thiopyran-4-yl)-urea; and
1-(2-fluoro-4-{4-[4-(2,2,2-trifluoro-1-hydroxy-1-trifluoromethyl-ethyl)-benzyl]-piperazine-1-carbonyl}-phenyl)-3-(1-oxo-tetrahydro-thiophen-3-yl)-urea; or a pharmaceutically acceptable salt thereof.

The hexafluoroisopropanol derivatives of the invention can be prepared using general synthetic methods known in the art of organic synthesis, for instance by using synthetic routes depicted in Schemes 1-6. Those skilled in the art will know that the order of addition of the key building blocks according to Formulas 2-21 can be altered and still give the desired products of Formula I. Reaction Schemes 1-2 represent two general methods for synthesising the intermediate alkylating agents of Formula 5 and acid derivatives of Formula 6, starting with an amine intermediate of Formula 2 and an ester derivative of Formula 7 respectively. Reaction Scheme 3 gives general conditions for converting the intermediate alkylating agents of Formula 5 and acid derivatives of Formula 6 into the (homo)piperazine derivatives of Formula 11. The (homo)piperazine derivatives of Formula 11 are then used in reaction Schemes 4-6 to synthesise compounds of the invention according to Formula I, using the general methods described. More specifically, reaction Scheme 4 is utilised when W=NH, reaction Scheme 5 is utilised when W=O and reaction Scheme 6 is utilised when W=CH$_2$, to give compounds of the invention according to Formula I.

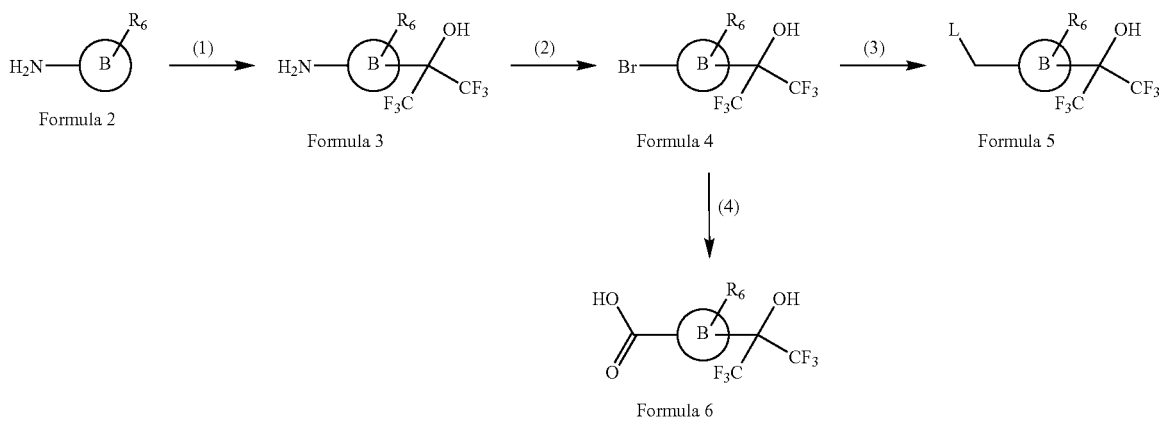

In this reaction scheme R$_6$ and ring B have the meaning as previously defined and L represents a leaving group e.q. OSO$_2$Me.

Conditions:
(1) hexafluoroacetone trihydrate, p-toluenesulfonic acid monohydrate, heat;
(2) dioxane, water, hydrobromic acid (48% weight in water), sodium nitrite, copper (I) bromide;
(3)(a) anhydrous tetrahydrofuran, −78° C., n-butyl lithium in hexane (2.5M), N,N-dimethylformamide;
(b) sodium borohydride, methanol, dichloromethane;
(c) When L is OSO$_2$Me: methanesulfonyl chloride, dichloromethane, triethylamine, 0° C.;
(4) anhydrous tetrahydrofuran, −78° C., n-butyl lithium in hexane (2.5M), carbon dioxide.

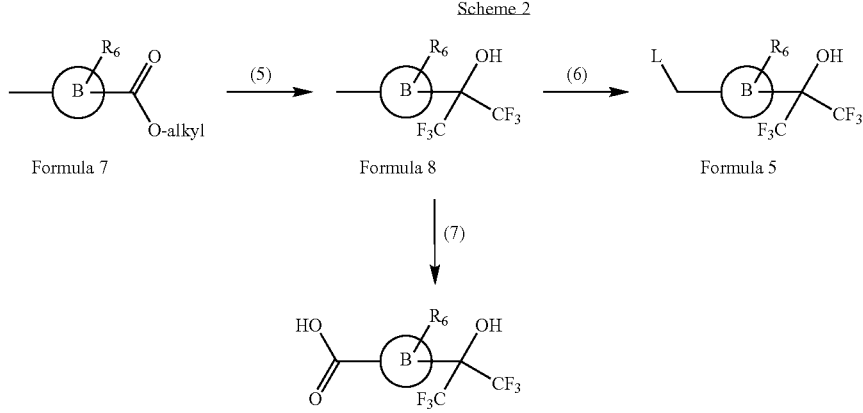

Scheme 2

In this reaction scheme R$_6$ and ring B have the meaning as previously defined, alkyl represents a (C$_{1-6}$)alkyl group and L represents a leaving group e.g. Br.

Conditions:
(5) cesium fluoride, (trifluoromethyl)trimethylsilane, N,N-dimethylformamide;
(6) When L is Br: N-bromosuccinimide, 2,2'-azobis(isobutyronitrile), CCl$_4$, reflux;
(7) potassium permanganate, water, elevated temperature.

Scheme 3

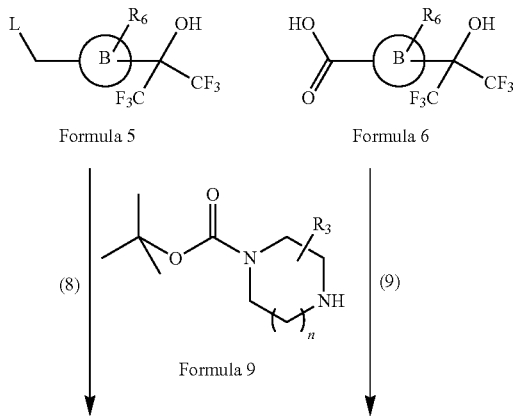

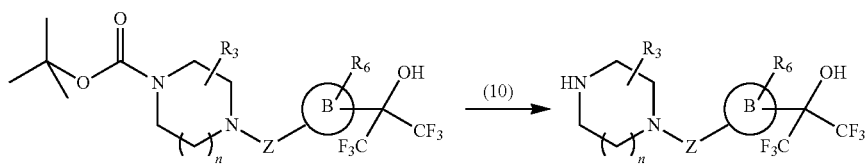

In this reaction scheme n, Z, R$_3$, R$_6$ and ring B have the meaning as previously defined and L represents a leaving group e.g. OSO$_2$Me or Br.

Conditions:

(8) Formula 9, potassium carbonate, acetonitrile, room or elevated temperature;

(9) Formula 9, N-(3-dimethylaminopropyl)-N'-ethylcarbodiimide hydrochloride or 1-propanephosphonic acid cyclic anhydride, dichloromethane, triethylamine;

(10) trifluoroacetic acid, dichloromethane.

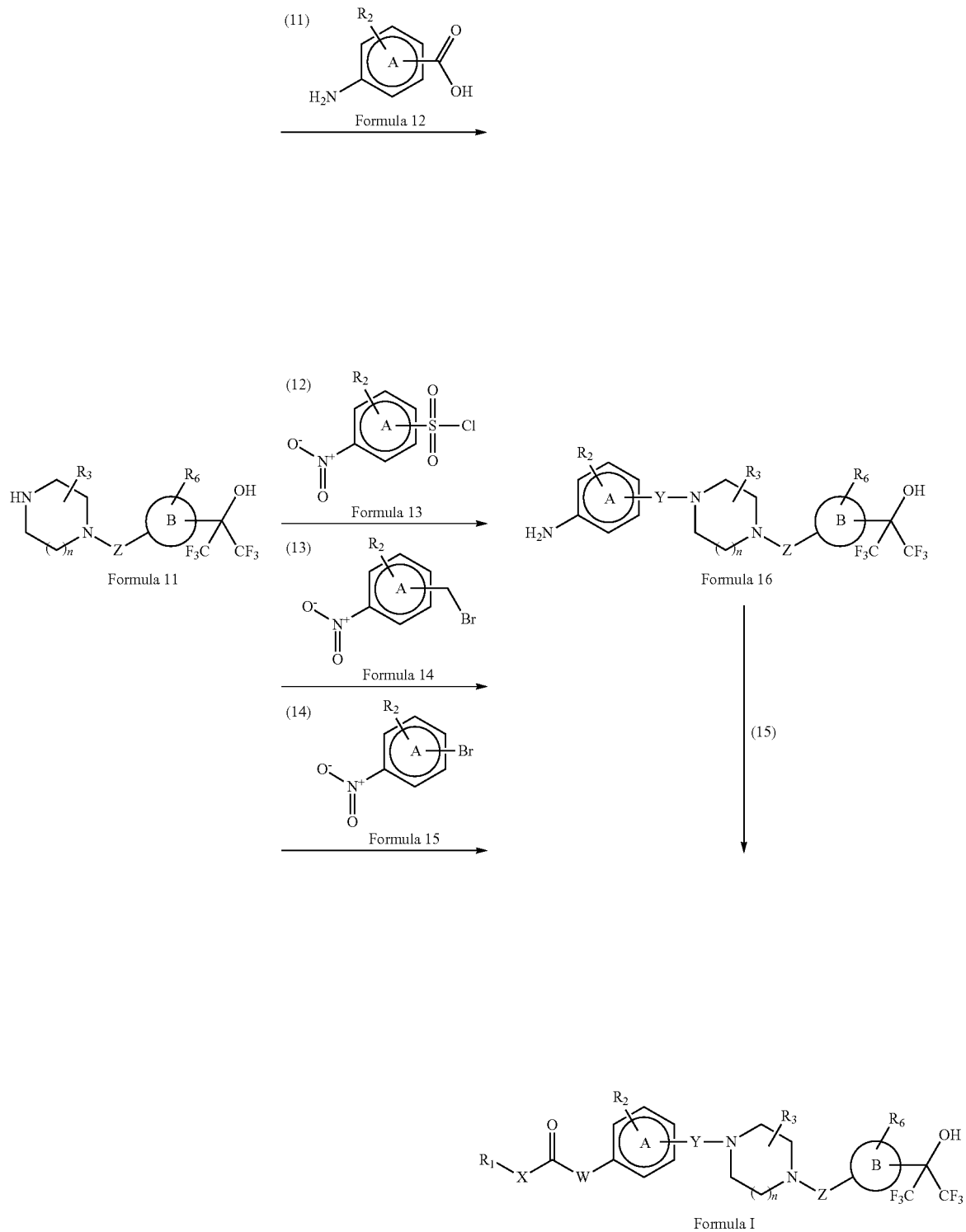

In this reaction scheme n, Z, R₁, R₂, R₃, R₄, R₆, X, Y and rings A and B have the meaning as previously defined.

Conditions:
(11) Formula 12, N-(3-dimethylaminopropyl)-N'-ethylcarbodiimide hydrochloride or 1-propanephosphonic acid cyclic anhydride, dichloromethane, triethylamine;
(12)(a) Formula 13, dichloromethane, pyridine;
(b) palladium on carbon, ethyl acetate, hydrogen or iron powder, isopropanol, hydrochloric acid, reflux;
(13)(a) Formula 14, acetonitrile, potassium carbonate, room or elevated temperature
(b) palladium on carbon, ethyl acetate, hydrogen or iron powder, isopropanol, hydrochloric acid, reflux;
(14)(a) Formula 15, tris(dibenzylideneacetone)dipalladium (0), 2-(dicyclohexylphosphino)-biphenyl, sodium tert-butoxide, toluene, heat;
(b) palladium on carbon, ethyl acetate, hydrogen or iron powder, isopropanol, hydrochloric acid, reflux;
(15) When X is NH, $NR_4$ or O: 4-nitrophenyl chloroformate or (bis(trichloromethyl)-carbonate (triphosgene), dichloromethane, and an amine of Formula $R_1NH_2$, an amine of Formula $R_1R_4NH$ or excess alcohol of Formula $R_1OH$, respectively;
When X is bond: dichloromethane, triethylamine, and an acid chloride of Formula $R_1CO_2Cl$.

Scheme 5 (when W is O):

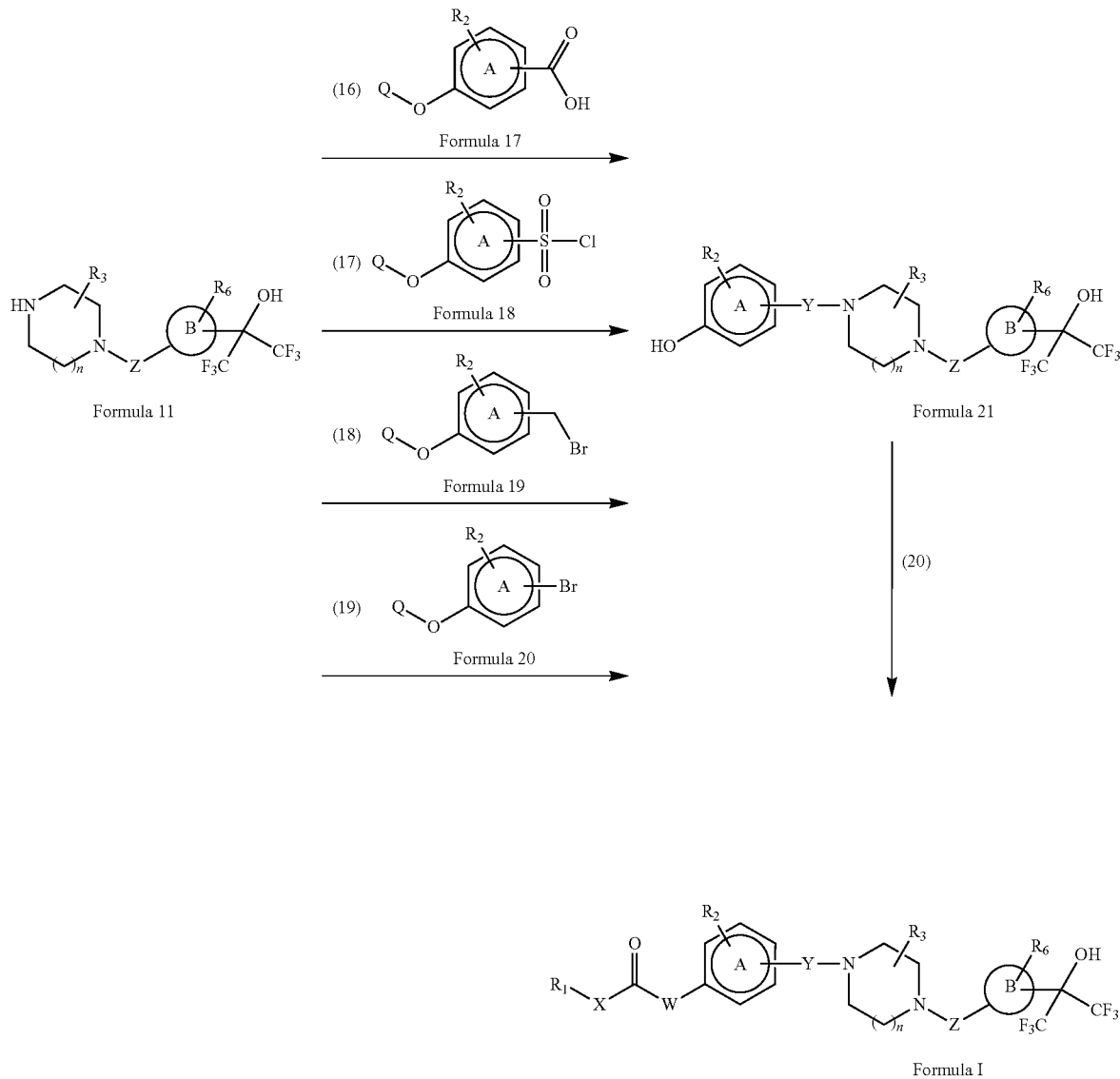

In this reaction scheme n, Z, $R_1$, $R_2$, $R_3$, $R_4$, $R_5$, $R_6$, X, Y and rings A and B have the meaning as previously defined.

In this reaction scheme Q represents hydrogen or if required an oxygen protecting group e.g. tert-butyldimethylsilyl or methyl which can be deprotected by e.g. hydrofluoric acid or boron tribromide respectively to yield the phenolic intermediates of Formula (21).

Conditions:
(16) Formula 17, N-(3-dimethylaminopropyl)-N'-ethylcarbodiimide hydrochloride or 1-propanephosphonic acid cyclic anhydride, dichloromethane, triethylamine;
(17) Formula 18, dichloromethane, pyridine;
(18) Formula 19, acetonitrile, potassium carbonate, room or elevated temperature;
(19) Formula 20, tris(dibenzylideneacetone)dipalladium(0), 2-(dicyclohexylphosphino)-biphenyl, sodium tert-butoxide, toluene, heat;
(20) When X is NH, $NR_4$ or O: 4-nitrophenyl chloroformate or (bis(trichloromethyl)carbonate (triphosgene), dichloromethane, and an amine of Formula $R_1NH_2$, an amine of Formula $R_1R_4NH$ or excess alcohol of Formula $R_1OH$, respectively;
When X is bond: dichloromethane, triethylamine, and an acid chloride of Formula $R_1CO_2Cl$.

(b) N-(3-dimethylaminopropyl)-N'-ethylcarbodiimide hydrochloride or 1-propanephosphonic acid cyclic anhydride, dichloromethane, triethylamine and an amine of Formula $R_1NH_2$, an amine of Formula $R_1R_4NH$ or an excess alcohol of Formula $R_1OH$, respectively;
When X is Bond: (a) Formula 26, lithium hydroxide tetrahydrofuran/methanol/water mixture
(b) N-methoxy-N-methyl amine, N-(3-dimethylaminopropyl)-N'-ethylcarbodiimide hydrochloride or 1-propanephosphonic acid cyclic anhydride, dichloromethane, triethylamine
(c) a Grignard reagent of Formula $R_1MgBr$, tetrahydrofuran.

The amine derivatives of Formula 2, the ester derivatives of Formula 7, the (homo)-piperazine derivatives of Formula 9, the acid derivatives of Formulae 12, 17 and 22, the sulfonyl chloride derivatives of Formulae 13, 18 and 23, and the bromide derivatives of Formulae 14, 15, 19, 20, 24 and 25 are

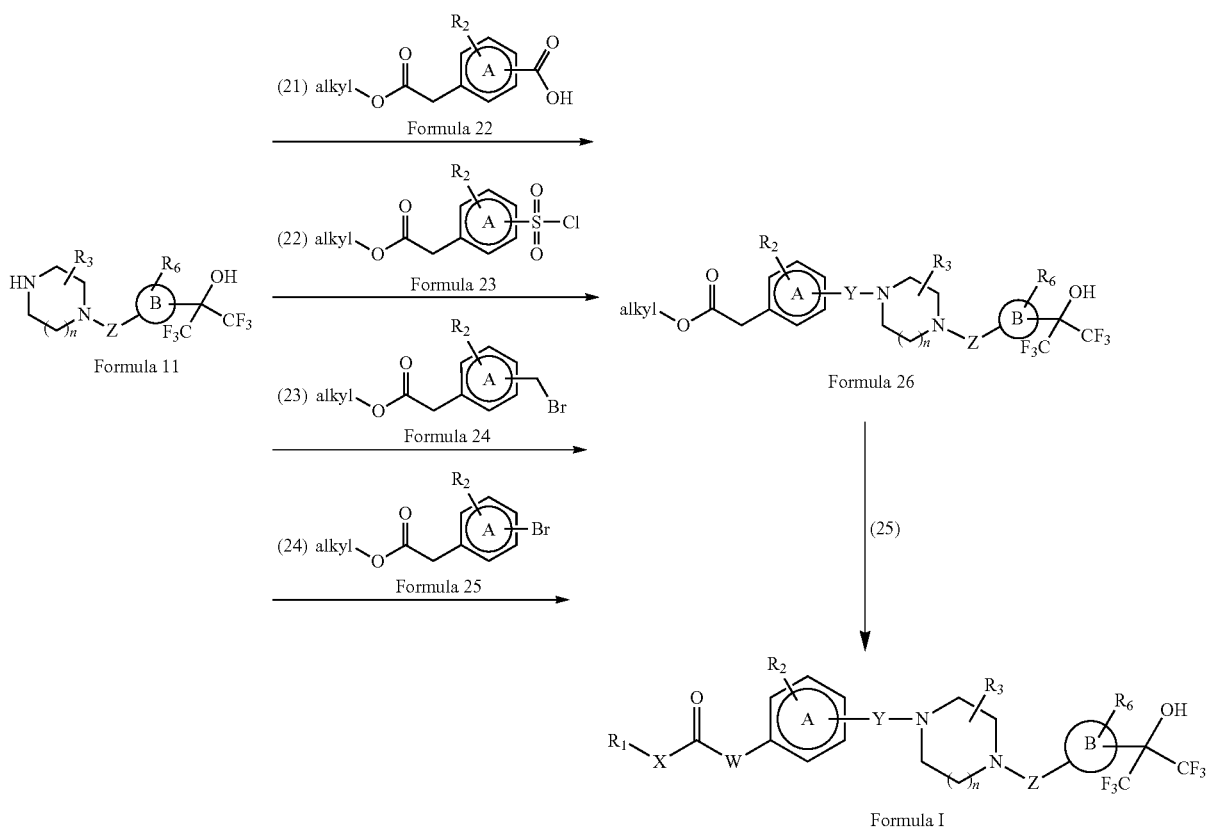

Scheme 6 (when W is CH₂)

Conditions:
(21) Formula 22, N-(3-dimethylaminopropyl)-N'-ethylcarbodiimide hydrochloride or 1-propanephosphonic acid cyclic anhydride, dichloromethane, triethylamine;
(22) Formula 23, dichloromethane, pyridine;
(23) Formula 24, acetonitrile, potassium carbonate, room or elevated temperature;
(24) Formula 25, tris(dibenzylideneacetone)dipalladium(0), 2-(dicyclohexylphosphino)-biphenyl, sodium tert-butoxide, toluene, heat;
(25) When X is NH or $NR_4$ or O: (a) Formula 26, lithium hydroxide tetrahydrofuran/methanol/water mixture compounds that can be prepared using methods well known in the art from commercially available intermediates.

The term O-protecting group, as used above, means a group commonly used for the protection of a hydroxyl group, like tert-butyldimethylsilyl or methyl. Removal of these and other protecting groups can take place in different ways, depending on the nature of those protecting groups. An overview of protecting groups and methods for their removal is given in T. W. Greene and P. G. M. Wuts, "*Protective Groups in Organic Synthesis*", 2$^{nd}$ edition, 1991, John Wiley & Sons, Inc.

The hexafluoroisopropanol derivatives of Formula I and their salts may contain at least one centre of chirality, and exist therefore as stereoisomers, including enantiomers and diastereomers. The present invention includes the aforementioned stereoisomers within its scope and each of the individual R and S enantiomers of the compounds of Formula I and their salts, substantially free, i.e. associated with less than 5%, preferably less than 2%, in particular less than 1% of the other enantiomer, and mixtures of such enantiomers in any proportions including the racemic mixtures containing substantially equal amounts of the two enantiomers. Methods for asymmetric synthesis whereby the pure stereoisomers are obtained are well known in the art, e.g. synthesis with chiral induction or starting from chiral intermediates, enantioselective enzymatic conversions, separation of stereoisomers or enantiomers using chromatography on chiral media. Such methods are for example described in *Chirality in Industry* (edited by A. N. Collins, G. N. Sheldrake and J. Crosby, 1992; John Wiley).

The present invention also embraces isotopically-labelled hexafluoroisopropanol derivatives of Formula I which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively.

Certain isotopically-labelled compounds of Formula (I) (e.g., those labelled with $^3$H and $^{14}$C) are useful in compound and/or substrate tissue distribution assays. Tritiated (i.e., $^3$H) and carbon-14 (i.e., $^{14}$C) isotopes are particularly preferred for their ease of preparation and detectability. Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. $^{11}$C and $^{18}$F are the preferred isotopes to be incorporated in a compound of the invention for use as a PET (Positron Emission Tomography) tracer. Isotopically labelled compounds of Formula (I) can generally be prepared by following procedures analogous to those disclosed in the Schemes and/or in the Examples hereinbelow, by substituting an appropriate isotopically labelled reagent for a non-isotopically labelled reagent.

Pharmaceutically acceptable salts may be obtained by treating a free base of a compound of Formula I with a mineral acid such as hydrochloric acid, hydrobromic acid, phosphoric acid and sulfuric acid, or an organic acid such as for example ascorbic acid, citric acid, tartaric acid, lactic acid, maleic acid, malonic acid, fumaric acid, glycolic acid, succinic acid, propionic acid, acetic acid, methane sulfonic acid, and the like.

The compounds of the invention may exist in unsolvated as well as in solvated forms with pharmaceutically acceptable solvents such as water, ethanol and the like. In general, the solvated forms are considered equivalent to the unsolvated forms for the purpose of the invention.

The present invention further provides pharmaceutical compositions comprising a hexafluoroisopropanol derivative having the general Formula I, or a pharmaceutically acceptable salt thereof, in admixture with one or more pharmaceutically acceptable auxiliaries, and optionally other therapeutic agents. The term "acceptable" means being compatible with the other ingredients of the composition and not deleterious to the recipients thereof. Compositions include e.g. those suitable for oral, sublingual, subcutaneous, intravenous, epidural, intrathecal, intramuscular, transdermal, pulmonary, local, or rectal administration, and the like, all in unit dosage forms for administration. For oral administration, the active ingredient may be presented as discrete units, such as tablets, capsules, powders, granulates, solutions, suspensions, and the like. For parenteral administration, the pharmaceutical composition of the invention may be presented in unit-dose or multi-dose containers, e.g. injection liquids in predetermined amounts, for example in sealed vials and ampoules, and may also be stored in a freeze dried (lyophilized) condition requiring only the addition of sterile liquid carrier, e.g. water, prior to use.

Mixed with one or more pharmaceutically acceptable auxiliaries, e.g. as described in the standard reference, Gennaro, A. R. et al., Remington: *The Science and Practice of Pharmacy* (20th Edition., Lippincott Williams & Wilkins, 2000, see especially Part 5: Pharmaceutical Manufacturing), the active agent may be compressed into solid dosage units, such as pills, tablets, or be processed into capsules, suppositories or patches. By means of pharmaceutically acceptable liquids the active agent can be applied as a fluid composition, e.g. as an injection preparation, in the form of a solution, suspension, emulsion, or as a spray, e.g. a nasal spray.

For making solid dosage units, the use of conventional additives such as fillers, colorants, polymeric binders and the like is contemplated. In general any pharmaceutically acceptable additive which does not interfere with the function of the active compounds can be used. Suitable carriers with which the active agent of the invention can be administered as solid compositions include lactose, starch, cellulose derivatives and the like, or mixtures thereof, used in suitable amounts. For parenteral administration, aqueous suspensions, isotonic saline solutions and sterile injectable solutions may be used, containing pharmaceutically acceptable dispersing agents and/or wetting agents, such as propylene glycol or butylene glycol.

The invention further includes a pharmaceutical composition, as hereinbefore described, in combination with packaging material suitable for said composition, said packaging material including instructions for the use of the composition for the use as hereinbefore described.

The hexafluoroisopropanol derivatives of the present invention were found to be modulators of LXRα and/or LXRβ, especially having agonistic activity thereon, and are as such useful in preventing and reducing the risk of atherosclerosis and related disorders associated with cholesterol and bile acids transport and metabolism, such as hypercholesterolemia (e.g. coronary heart disease), cholesterol gallstones, lipid storage diseases, diabetes and obesity.

The compounds of the invention are potentially also useful in further indications such as:

Inflammatory Disease:

Ligand activation of LXR has been shown to inhibit a number of inflammatory pathways e.g. Interleukin1-β, Interleukin-6, cyclooxygenase-2 and most recently shown to directly inhibit C-reactive protein expression. See Blaschke et al., *Circ. Res.* 99: 88-99. (2006). Compounds of the invention may have therapeutic utility in suppression of inflammation in inflammatory diseases such as contact dermatitis (see Fowler et al., *J. Invest. Dermatol.* 120:246-55. (2003); neuroinflammatory diseases such as multiple sclerosis (Zhang-Gandhi and Drew. *J. Neuroimmunol.* 183:50-59. (2007)) and autoimmune encephalomyelitis. See Hindinger et al., *J. Neurosci. Res.* 84:1225-1234 (2006).

Proliferative Vascular Disease:

The LXR ligand T0901317 has been shown to inhibit vascular smooth muscle cell proliferation and neointima formation following balloon injury in vitro and in vivo. Compounds of the invention may therefore have therapeutic utility in proliferative vascular diseases. See Blaschke et al., *Circ. Res.* 95:110-123 (2004).

Diabetes/Metabolic Syndrome:

Recent literature has demonstrated efficacy of LXR agonists in animal models of insulin resistance and diabetes and thus compounds of the invention may have potential therapeutic utility in the treatment of diabetes and metabolic syndrome (see Liu et al., *Endocrinology.* 147:5061-5068 (2006); Fernandez-Veledo et al., *Diabetologia.* 49:3038-3048 (2006)).

Cancer:

The LXR agonist T0901317 delayed progression of tumours in an animal model of prostate cancer. Compounds of the invention may be potentially useful for treatment of prostate cancer. See Chuu et al., *Cancer. Res.* 66:6482-6486 (2006).

Neurodegenerative Disease:

Via modulation of cellular cholesterol levels, LXR agonists can reduce the deposition of β-amyloid in the brain. In addition T0901317 has been shown to lower deposition of β-amyloid but also improve memory. See Riddell et al., *Mol. Cell. Neurosci.* 34: 621-628 (2007). The agonist derivatives of the present invention may therefore have therapeutic utility in neurodegenerative diseases such as Alzheimers disease.

Combination Therapies:

The compounds of the invention may be combined with another therapeutic agent that is useful in the treatment of other metabolic disorders such as; hypertension, hyperlipidaemias, dyslipidaemias, diabetes, chronic inflammatory disorders, obesity and in any condition where enhancement of reverse cholesterol transport and/or improvement of LDL: HDL ratios would be of potential clinical benefit. Examples of such therapies are: inhibitors of 3-hydroxy-3-methyl-glutaryl-CoA reductase (HMG CoA reductase) (e.g. atorvastatin, pravastatin, simvastatin, lovastatin, rosuvastatin and others), cholesterol absorption inhibitors (e.g. ezetimibe), bile sequestrants (e.g. cholestyramine), microsomal triglyceride transfer protein (MTP) inhibitors, peroxisome proliferator-activated receptor modulators (e.g. muraglitazar, rosiglitazone, fibrates and others), cholesterol ester transfer protein inhibitors, nicotinic acid derivatives (e.g. Niaspan® etc), Acyl coenzyme A: cholesterol acyl transferase (ACAT) inhibitors (e.g. eflucimibe), farnesoid X receptor modulators, therapies used for the treatment of metabollic syndrome or type 2 diabetes e.g. mefformin. Compounds of the invention may be combined with anti-inflammatory therapies (e.g. aspirin) and with treatments for neurodegenerative diseases (e.g Aricept®, Exelon®, Reminyl® and Ebixa®).

The compounds of the invention may be administered for humans in a sufficient amount and for a sufficient amount of time to alleviate the symptoms. Illustratively, daily dosage levels for humans can be in the range of 0.001-50 mg per kg body weight, preferably in a daily dosage of 0.01-20 mg per kg body weight.

The invention is illustrated by the following Examples.

GENERAL EXPERIMENTAL

High Performance Liquid Chromatography (HPLC)

HPLC purification is used within this experimental section and refers to High Performance Liquid Chromatography. Some examples of general methods that may be used to purify compounds are: acidic reverse phase HPLC (water/acetonitrile/0.1% trifluoroacetic acid) using a standard gradient of 5% acetonitrile/95% water to 100% acetonitrile or basic reverse phase HPLC (water/acetonitrile/0.1% ammonia solution) using a standard gradient of 10% acetonitrile/90% water to 100% acetonitrile. UV detection e.g. 254 nM is used for the collection of fractions from HPLC. This description gives general methods and variations in types of equipment, columns, mobile phase, detection wavelength, solvent gradient and run time may also be used to purify compounds.

Free Base and Salts

After purification by acidic HPLC basic products can either be isolated as the trifluoroacetic acid salt or liberated as the free base by common generic methods e.g. strong cation exchange chromatography eluting with 2M ammonia in methanol or silica carbonate column chromatography or partitioning between an organic solvent e.g. ethyl acetate and aqueous base e.g. sodium hydrogen carbonate, separating the organic layer, drying with inorganic solid e.g. magnesium sulfate, filtering and concentration under reduced pressure.

The free base of products can also be converted to hydrochloride salts by standard methods e.g. dissolving the free base in dichloromethane and adding 2M hydrochloric acid in ether and concentrating under reduced pressure to give the hydrochloride salt.

Abbreviations:

Boc: tert-butoxycarbonyl; CDCl$_3$: chloroform-d; CD$_3$OD: methanol-d4; (CD$_3$)$_2$SO: diemthylsulfoxide-d6; HPLC: high performance liquid chromatography; HOBt: 1H-benzo[d][1,2,3]triazol-1-ol; HATU: O-(7-azabenzotriazol-1-yl)-N,N,N,N-tetramethyl uronium hexafluorophosphate; EDCI: N-(3-dimethylaminopropyl)-N'-ethylcarbodiimide hydrochloride; triphosgene: bis(trichloromethyl) carbonate; Hunig's base: N-ethyl-N-isopropylpropan-2-amine; SCX: strong cation exchange.

EXAMPLE 1

1-(4-(4-(3-(1,1,1,3,3,3-Hexafluoro-2-hydroxypropan-2-yl)benzyl)piperazine-1-carbonyl)-phenyl)-3-isopropylurea

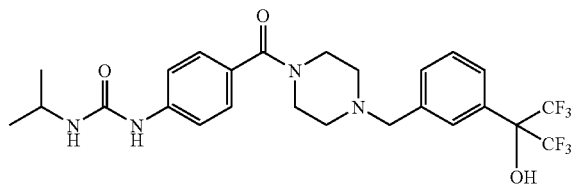 [SMILES: CC(C)NC(=O)Nc1ccc(C(=O)N2CCN(Cc3cccc(C(O)(C(F)(F)F)C(F)(F)F)c3)CC2)cc1]

A: Methyl 3-(piperazin-1-ylmethyl)benzoate

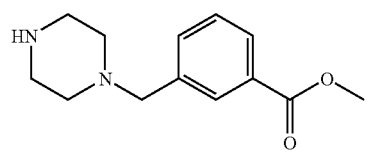 [SMILES: COC(=O)c1cccc(CN2CCNCC2)c1]

To a solution of methyl (3-bromomethyl)benzoate (4.00 g, 17.46 mmol), triethyl-amine (4.90 mL, 34.92 mmol) and acetonitrile (25 mL) was added tert-butyl 1-piperazine-carboxylate (3.25 g, 17.46 mmol). The reaction was stirred at ambient temperature for 3 hours and then concentrated under vacuum. The residue was dissolved in dichloromethane, filtered and treated with 2,2,2-trifluoroacetic acid (6.70 mL, 87.31 mmol). The mixture was stirred at 60° C. for 1 hour before being concentrated under vacuum and treated with strong cation exchange column chromatography to afford the title compound (2.47 g). MS (ESI) m/z 235.4 [M+H]$^+$

B: Methyl 3-((4-(4-nitrobenzoyl)piperazin-1-yl)methyl)benzoate

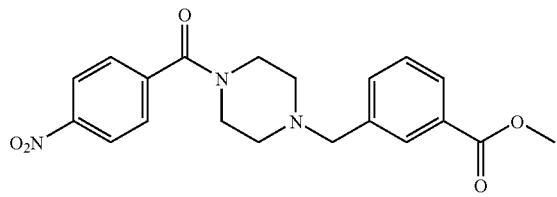 [SMILES: COC(=O)c1cccc(CN2CCN(C(=O)c3ccc([N+](=O)[O-])cc3)CC2)c1]

A mixture of methyl 3-(piperazin-1-ylmethyl)benzoate (2.47 g, 10.542 mmol), 4-nitrobenzoic acid (1.77 g, 10.542 mmol), 1-(3-dimethylaminopropyl)-3-ethylcarbodiimide hydrochloride (3.03 g, 15.813 mmol), triethylamine (2.94 mL, 21.084 mmol) and acetonitrile (40 mL) were stirred together, at ambient temperature, for 4 hours before being concentrated under vacuum. The residue was dissolved in ethyl acetate, filtered, washed with water (×2) and treated with strong cation exchange column chromatography to afford the title compound (3.12 g). MS (ESI) m/z 384.3 [M+H]$^+$

C: (4-(3-(1,1,1,3,3,3-Hexafluoro-2-hydroxypropan-2-yl)benzyl)piperazin-1-yl)(4-nitro-phenyl)methanone

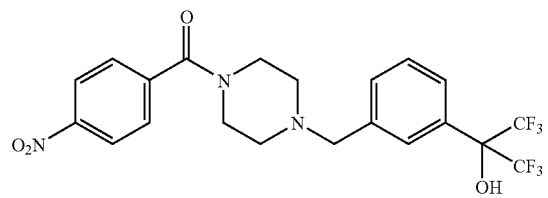 [SMILES: O=C(c1ccc([N+](=O)[O-])cc1)N1CCN(Cc2cccc(C(O)(C(F)(F)F)C(F)(F)F)c2)CC1]

Cesium fluoride (297 mg, 1.956 mmol) was added to a solution of methyl 3-((4-(4-nitrobenzoyl)piperazin-1-yl)methyl)benzoate (500 mg, 1.304 mmol) and (trifluoromethyl)-trimethylsilane (964 μL) in N,N-dimethylformamide at −78° C. The mixture was slowly allowed to warm to ambient temperature over 24 hours. The resulting brown liquid was absorbed onto silica and purified by silica chromatography (eluting with a solvent gradient from dichloromethane to 4% methanol/dichloromethane) to afford the title compound (180 mg). MS (ESI) m/z 492.1 [M+H]$^+$

D: (4-Aminophenyl)(4-(3-(1,1,1,3,3,3-hexafluoro-2-hydroxypropan-2-yl)benzyl)piperazin-1-yl)methanone

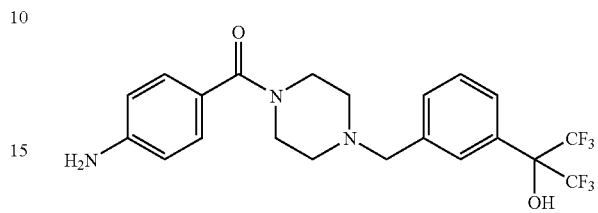

(4-(3-(1,1,1,3,3,3-Hexafluoro-2-hydroxypropan-2-yl)benzyl)piperazin-1-yl)(4-nitrophenyl)methanone (180 mg, 0.37 mmol), iron powder (205 mg, 3.66 mmol), 1 M hydrochloric acid (549 μL, 0.55 mmol) and isopropanol (10 mL) were stirred together, at ambient temperature, for 2 hours before being filtered and concentrated under vacuum. The residue was treated with strong cation exchange column chromatography and purified by silica chromatography (eluting with a solvent gradient from dichloromethane to 4% methanol/dichloromethane). The product was recrystallised from benzonitrile to afford the title compound (131 mg). MS (ESI) m/z 462.1 [M+H]$^+$

E: 1-(4-(4-(3-(1,1,1,3,3,3-Hexafluoro-2-hydroxypropan-2-yl)benzyl)piperazine-1-carbonyl)-phenyl)-3-isopropylurea (4-Aminophenyl)(4-(3-(1,1,1,3,3,3-hexafluoro-2-hydroxypropan-2-yl)benzyl)-piperazin-1-yl)methanone (131 mg, 0.28 mmol) was dissolved in acetonitrile (5 mL) and treated with 4-nitrophenyl carbonochloridate (57.8 mg, 0.29 mmol). This was stirred at room temperature for 1 hour before isopropylamine (0.121 mL, 1.42 mmol) was added. The reaction was stirred for a further 2 hours at room temperature, filtered and concentrated under vacuum. The mixture was purified by HPLC and then treated with strong cation exchange column chromatography to afford the title compound (17.0 mg).

MS (ESI) m/z 547.3 [M+H]$^+$

The following compound was prepared in a similar manner:

1B: 1-Cyclobutyl-3-(4-(4-(3-(1,1,1,3,3,3-hexafluoro-2-hydroxypropan-2-yl)benzyl)piperazine-1-carbonyl)phenyl)urea

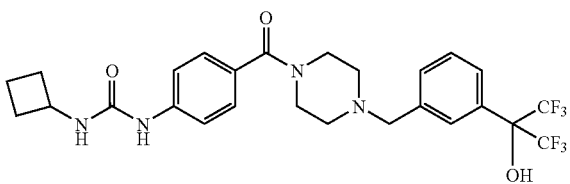 [SMILES: O=C(Nc1ccc(C(=O)N2CCN(Cc3cccc(C(O)(C(F)(F)F)C(F)(F)F)c3)CC2)cc1)NC1CCC1]

MS (ESI) m/z 559.2 [M+H]$^+$

EXAMPLE 2

1-(Cyclopropylmethyl)-3-(4-(4-(4-(1,1,1,3,3,3-hexafluoro-2-hydroxypropan-2-yl)benzyl)piperazine-1-carbonyl)phenyl)urea

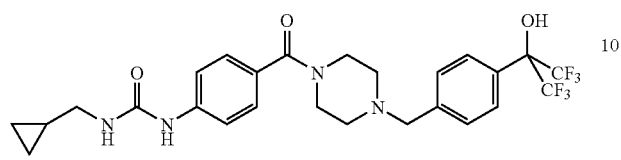

A: Ethyl 4-(3-(cyclopropylmethyl)ureido)benzoate

To cyclopropylmethanamine (57.5 mmol, 4.99 ml, 4.09 g) in dichloromethane (40 mL) was added to ethyl 4-isocyanatobenzoate (52.3 mmol, 10 g) in dichloromethane (45 mL) and the reaction stirred overnight. The reaction was then concentrated under reduced pressure to give the title compound (14.7 g).
$^1$H NMR (CDCl$_3$, 400 MHz): δ 0.2 (2H, m) 0.5, (2H, m) 0.95 (1H, m) 1.4 (3H, t), 3.1 (2H, m) 4.35 (2H, q), 5.15 (1H, br s), 7.0 (1H, br s), 7.4 (2H, d) 8.0 (2H, d)

B: 4-(3-(Cyclopropylmethyl)ureido)benzoic acid

Ethyl 4-(3-(cyclopropylmethyl)ureido)benzoate (55.3 mmol, 14.5 g) was suspended in ethanol (400 ml) and 4M sodium hydroxide (332 mmol, 83 mL) added. The reaction was then refluxed until complete saponification was achieved. The ethanol was removed by evaporation and the reaction neutralised with concentrated hydrochloric acid. The white precipitate was collected and washed with water. The material was dried under vacuum to give the title compound (12.1 g)
$^1$H NMR ((CDCl$_3$)$_2$SO, 400 MHz): δ0.2 (2H, m) 0.5, (2H, m) 0.95 (1H, m), 3.0 (2H, m) 6.35 (1H, br s) 7.4 (2H, d) 7.8 (2H, d) 8.9 (1H, br s)

C: tert-Butyl 4-(4-(3-(cyclopropylmethyl)ureido)benzoyl)piperazine-1-carboxylate To a stirred mixture of tert-butyl piperazine-1-carboxylate (45.8 mmol, 8.53 g) and 4-(3-(cyclopropylmethyl)ureido)benzoic acid (45.8 mmol, 10.73 g) in dichloromethane (200 ml) was added triethylamine (103 mmol, 14.36 mL, 10.43 g) followed by 1-propane-phosphonic acid cyclic anhydride (68.7 mmol, 40.7 mL, 43.7 g; 50% solution in ethyl acetate). The reaction was stirred for 1 hour, then poured into saturated sodium hydrogen carbonate solution and extracted with dichloromethane. The organic phase was dried (magnesium sulfate), filtered and evaporated to a white solid (17.13 g)
MS (ESI) m/z 403.5 [M+H]$^+$

D: 1-(Cyclopropylmethyl)-3-(4-(Piperazine-1-carbonyl)phenyl)urea tert-Butyl 4-(4-(3-(cyclopropylmethyl)ureido)benzoyl) piperazine-1-carboxylate (46.7 mmol, 18.78 g) was dissolved in dichloromethane (30 mL) and trifluoroacetic acid (233 mmol, 17.33 mL, 26.6 g) added. The reaction was stirred for 1 hour and then concentrated under reduced pressure. The crude material was triturated with ether to give a white powder after high vacuum drying, which was taken up in water and carefully taken to pH 10 with sodium carbonate. The aqueous was extracted with dichloromethane and the combined organic phases were dried, filtered and concentrated under reduced pressure to give the title compound (13.4 g)
$^1$H NMR(CDCl$_3$, 400 MHz): δ 0.2 (2H, m) 0.5, (2H, m) 0.95 (1H, m) 2.2 (2H, br s), 2.8 (4H, br s), 3.6 (4H, br s), 5.8 (1H, m) 7.2 (4H, m)

E: 2-(4-(Bromomethyl)phenyl)-1,1,1,3,3,3-hexafluoropropan-2-ol 1,1,1,3,3,3-Hexafluoro-2-p-tolylpropan-2-ol (387 mmol, 100 g) was dissolved in carbon tetrachloride (400 mL) and N-bromosuccinimide (387 mmol, 68.9 g) was added in one portion followed by 2,2'-azobis(isobutyronitrile) (0.387 mmol, 0.064 g). The reaction was stirred at reflux for 4 hours, filtered through dicalite and the filtrate was evaporated to leave crude oil. The crude oil was triturated with diethyl ether, the solid obtained was filtered off and the filtrate taken to dryness (3 times) to yield the title compound as an oil (138 g).
$^1$H NMR (CDCl$_3$, 400 MHz): δ 4.49 (2H, s), 7.49 (2H, d), 7.69 (2H, d)

F: 1-(Cyclopropylmethyl)-3-(4-(4-(4-(1,1,1,3,3,3-hexafluoro-2-hydroxypropan-2-yl))-piperazine-1-carbonyl)phenyl)urea A mixture of 1-(cyclopropylmethyl)-3-(4-(piperazine-1-carbonyl)phenyl)urea (100 mg, 0.33 mmol), 2-(4-(bromomethyl)phenyl)-1,1,1,3,3,3-hexafluoropropan-2-ol (117 mg, 0.347 mmol), potassium carbonate (100 mg 0.724 mmol) and sodium iodide (10 mg, 0.067 mmol) in acetonitrile (1.0 mL) was subject to microwave irradiation at 140° C. for 20 minutes. The mixture was diluted with acetonitrile, filtered and concentrated under vacuum. The residue was partitioned between ethyl acetate/water and the organic layer was separated. The aqueous layer was washed with ethyl acetate and the combined organic layers were washed with brine, dried over anhydrous magnesium sulfate and concentrated under vacuum. The mixture was purified by HPLC and then treated with strong cation exchange column chromatography to afford the title compound (25.1 mg).
MS (ESI) m/z 559.3 [M+H]$^+$

EXAMPLE 3

1-(4-(4-(4-(1,1,1,3,3,3-Hexafluoro-2-hydroxypropan-2-yl)benzyl)piperazine-1-carbonyl)phenyl)-3-(2-hydroxy-2-methylpropyl)urea

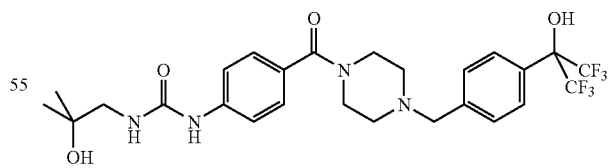

A: tert-Butyl 4-(4-aminobenzoyl)piperazine-1-carboxylate

1-Propanephosphonic acid cyclic anhydride (10.94 mmol, 6.51 mL, 6.96 g, 50% solution in ethyl acetate) was added to a stirred solution of 4-aminobenzoic acid (7.29 mmol, 1 g), tert-butyl piperazine-1-carboxylate (7.29 mmol, 1.358 g) and triethylamine (14.58 mmol, 1.969 mL, 1.473 g) in dichloromethane (30 mL). The reaction mixture was stirred for 5 hours, then was washed with sodium bicarbonate and filtered through silica, eluting with ethyl acetate. Evaporation of solvent afforded the title compound (1.53 g). $^1$H NMR (MeOD, 400 MHz): δ 1.4 (9H, s), 3.4 (4H, m), 3.6 (4H, m), 6.7 (1H, m), 7.2 (2H, m)

B: (4-Aminophenyl)(4-(4-(1,1,1,3,3,3-hexafluoro-2-hydroxypropan-2-yl)benzyl)piperazin-1-yl)methanone tert-Butyl 4-(4-aminobenzoyl)piperazine-1-carboxylate (4.98 mmol, 1.520 g) was dissolved in dichloromethane and trifluoroacetic acid added. The reaction was left overnight and then treated to SCX purification. The intermediate amine was combined with 2-(4-(bromomethyl)phenyl)-1,1,1,3,3,3-hexafluoropropan-2-ol (4.98 mmol, 1.678 g) and potassium carbonate (4.98 mmol, 0.688 g) in acetonitrile (30 mL) and stirred overnight. The reaction was concentrated under reduced pressure and the residue partitioned between water and ethyl acetate. The organic layer was separated and concentrated under reduced pressure. Purification by SCX column chromatography and silica chromatography (eluting with ethyl acetate) gave the title compound (1.25 g).

MS (ESI) m/z 462.5 [M+H]$^+$

C: 1-(4-(4-(4-(1,1,1,3,3,3-Hexafluoro-2-hydroxypropan-2-yl)benzyl)piperazine-1-carbonyl)phenyl)-3-(2-hydroxy-2-methylpropyl)urea 4-Nitrophenyl carbonochloridate (0.217 mmol, 43.7 mg) was added to a stirred solution of (4-aminophenyl)(4-(4-(1,1,1,3,3,3-hexafluoro-2-hydroxypropan-2-yl)benzyl)-piperazin-1-yl)methanone (0.217 mmol, 100 mg) in dichloromethane (1 mL). After 1 hour, 1-amino-2-methylpropan-2-ol (0.650 mmol, 58.0 mg) was added and stirring continued for 1 hour. The reaction mixture was purified by silica column chromatography (eluant dichloromethane/methanol 0% to 10%) to yield the title compound (30 mg).

MS (ESI) m/z 577.5 [M+H]$^+$

The following compounds were prepared in a similar manner:

3B: 1-(4-(4-(4-(1,1,1,3,3,3-Hexafluoro-2-hydroxypropan-2-yl)benzyl)piperazine-1-carbonyl)phenyl)-3-(3-hydroxy-3-methylbutyl)urea

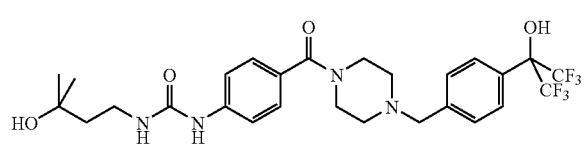 [SMILES: CC(C)(O)CCNC(=O)Nc1ccc(C(=O)N2CCN(Cc3ccc(C(O)(C(F)(F)F)C(F)(F)F)cc3)CC2)cc1]

MS (ESI) m/z 591.5 [M+H]$^+$

3C: 1-(4-(4-(4-(1,1,1,3,3,3-Hexafluoro-2-hydroxypropan-2-yl)benzyl)piperazine-1-carbonyl)phenyl)-3-((1-hydroxycyclopropyl)methyl)urea

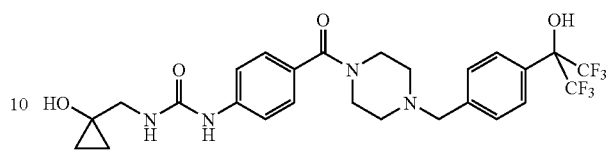

MS (ESI) m/z 575.3 [M+H]$^+$

3D: 1-Butyl-3-(4-(4-(4-(1,1,1,3,3,3-hexafluoro-2-hydroxypropan-2-yl)benzyl)piperazine-1-carbonyl)phenyl)urea

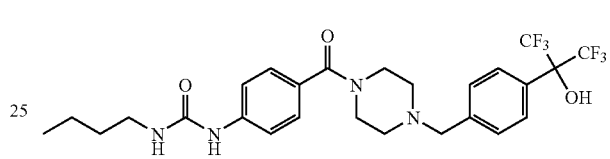

MS (ESI) m/z 561.3 [M+H]$^+$

EXAMPLE 4

1-(4-(4-(4-(1,1,1,3,3,3-Hexafluoro-2-hydroxypropan-2-yl)benzyl)piperazine-1-carbonyl)phenyl)-3-isopropylurea

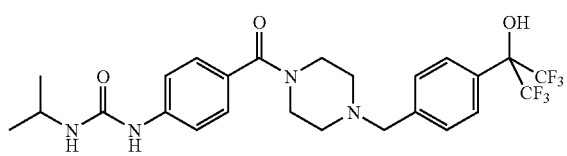 [SMILES: CC(C)NC(=O)Nc1ccc(C(=O)N2CCN(Cc3ccc(C(O)(C(F)(F)F)C(F)(F)F)cc3)CC2)cc1]

(4-Aminophenyl)(4-(4-(1,1,1,3,3,3-hexafluoro-2-hydroxypropan-2-yl)benzyl)-piperazin-1-yl)methanone (0.217 mmol, 0.1 g) and diisopropylethylamine (0.737 mmol, 0.122 mL, 0.095 g) were stirred in dichloromethane at room temperature. Triphosgene (0.080 mmol, 0.024 g) was added and the reaction mixture stirred for 30 minutes. Isopropylamine (0.433 mmol, 0.037 mL, 0.026 g) was added and the reaction stirred for a further 30 minutes. The reaction mixture was concentrated under vacuum and purified by reverse phase acidic preparative HPLC to afford the title compound (10 mg).

MS (ESI) m/z 547.3 [M+H]$^+$

The following compounds were prepared by a similar manner:

4B: 1-(4-(4-(4-(1,1,1,3,3,3-Hexafluoro-2-hydroxypropan-2-yl)benzyl)piperazine-1-carbonyl)phenyl)-3-isobutylurea MS (ESI) m/z 561.3 [M+H]$^+$ 4C: 1-Cyclobutyl-3-(4-(4-(4-(1,1,1,3,3,3-hexafluoro-2-hydroxypropan-2-yl)benzyl)-piperazine-1-carbonyl)phenyl)urea MS (ESI) m/z 559.0 [M+H]$^+$

EXAMPLE 5

N-(4-(4-(4-(1,1,1,3,3,3-Hexafluoro-2-hydroxypropan-2-yl)benzyl)piperazine-1-carbonyl)phenyl)-3-(1-methylcyclopropyl)propanamide

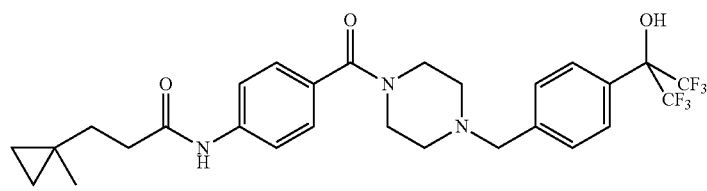 [SMILES: CC1(CCC(=O)Nc2ccc(C(=O)N3CCN(Cc4ccc(C(O)(C(F)(F)F)C(F)(F)F)cc4)CC3)cc2)CC1]

3-(1-Methylcyclopropyl)propionic acid (1.752 mmol, 0.2 g) was stirred in dichloromethane at 0° C. Oxalyl chloride (8.76 mmol, 0.752 mL, 1.112 g) was added and the reaction stirred overnight. The reaction mixture was concentrated under vacuum to give the intermediate 3-(1-methylcyclopropyl)propanoyl chloride. A mixture of 3-(1-methyl-cyclopropyl)propanoyl chloride (0.813 mmol, 0.119 g), (4-aminophenyl)(4-(4-(1,1,1,3,3,3-hexafluoro-2-hydroxypropan-2-yl)benzyl)piperazin-1-yl)methanone (0.542 mmol, 0.25 g) and triethylamine (1.084 mmol, 0.151 mL, 0.110 g) were stirred in dichloromethane at 0° C. for 1 hour. The reaction mixture was allowed to warm to room temperature. The reaction mixture was washed with water, concentrated under vacuum and purified by acidic prep HPLC to afford the title compound (67 mg). MS (ESI) m/z 572.3 [M+H]$^+$ The following compound was prepared in a similar manner:

5B: 3-Cyclopropyl-N-(4-(4-(4-(1,1,1,3,3,3-hexafluoro-2-hydroxypropan-2-yl)benzyl)piperazine-1-carbonyl)phenyl)propanamide MS (ESI) m/z 558.2 [M+H]$^+$

EXAMPLE 6

N-(4-(4-(4-(1,1,1,3,3,3-hexafluoro-2-hydroxypropan-2-yl)benzyl)piperazine-1-carbonyl)phenyl)-4-hydroxy-4-methylpentanamide

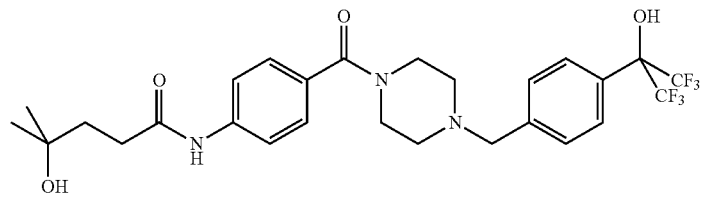 [SMILES: CC(C)(O)CCC(=O)Nc1ccc(C(=O)N2CCN(Cc3ccc(C(O)(C(F)(F)F)C(F)(F)F)cc3)CC2)cc1]

5,5-Dimethyldihydrofuran-2(3H)-one (0.433 mmol, 0.049 g) was stirred in toluene (5 mL). Trimethylaluminium (0.867 mmol, 0.867 mL, 1 M in heptane) was added and the reaction stirred for 10 minutes at room temperature. (4-Aminophenyl)(4-(4-(1,1,1,3,3,3-hexafluoro-2-hydroxypropan-2-yl)benzyl)piperazin-1-yl)methanone (0.433 mmol, 0.2 g) was added and the reaction heated to reflux for 1 hour then a drop of N,N-dimethylformamide was added. The reaction mixture was heated to reflux for 1 hour. The reaction mixture was quenched with water. Ethyl acetate was added and the layers separated. The organic phase was concentrated under vacuum and the resulting residue purified by acidic preparative HPLC to afford the desired compound (1 mg).

MS (ESI) m/z 576.3 [M+H]$^+$

EXAMPLE 7

1-(2-Fluoro-4-(4-(4-(1,1,1,3,3,3-hexafluoro-2-hydroxypropan-2-yl)benzyl)piperazine-1-carbonyl)phenyl)-3-(2-hydroxy-2-methylpropyl)urea

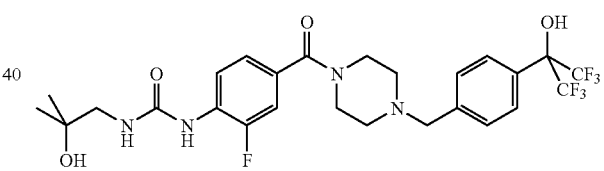

A: tert-Butyl 4-(4-amino-3-fluorobenzoyl)piperazine-1-carboxylate

1-Propanephosphonic acid cyclic anhydride (9.67 mmol, 5.76 mL, 50% solution in ethyl acetate) was added to a solution of 4-amino-3-fluorobenzoic acid (6.45 mmol, 1 g), tert-butyl piperazine-1-carboxylate (6.45 mmol, 1.2 g) and triethylamine (12.89 mmol, 1.74 mL) in dichloromethane (20 mL) and stirred for 2 hours. The reaction mixture was washed with sodium bicarbonate solution and concentrated under vacuum to give the title compound (2.09 g). MS (ESI) m/z 324.5 [M+H]⁺

B: (4-Amino-3-fluorophenyl)(4-(4-(1,1,1,3,3,3-hexafluoro-2-hydroxypropan-2-yl)benzyl)-piperazin-1-yl)methanone tert-Butyl 4-(4-amino-3-fluorobenzoyl)piperazine-1-carboxylate (0.649 mmol, 210 mg) was stirred with dichloromethane (~2 mL) and trifluoroacetic acid (~0.5 mL) overnight. The mixture was purified by SCX chromatography to give the intermediate (4-amino-3-fluorophenyl)(piperazin-1-yl)methanone. 2-(4-(Bromomethyl)phenyl)-1,1,1,3,3,3-hexafluoropropan-2-ol (0.649 mmol, 219 mg), potassium carbonate (0.649 mmol, 90 mg) and acetonitrile (5 mL) were added to the intermediate (4-amino-3-fluorophenyl)(piperazin-1-yl)methanone and the mixture was stirred for 6 hours. The reaction mixture was concentrated under reduced pressure. The residue obtained was stirred in dichloromethane, filtered and the filtrate was purified by silica chromatography (eluting with dichloromethane increasing to ethyl acetate) to afford the title compound (46 mg).

MS (ESI) m/z 480.1 [M+H]⁺

C: 1-(2-Fluoro-4-(4-(4-(1,1,1,3,3,3-hexafluoro-2-hydroxypropan-2-yl)benzyl)piperazine-1-carbonyl)phenyl)-3-(2-hydroxy-2-methylpropyl)urea 4-Nitrophenyl carbonochloridate (0.209 mmol, 42.0 mg) was added to a stirred solution of (4-amino-3-fluorophenyl)(4-(4-(1,1,1,3,3,3-hexafluoro-2-hydroxypropan-2-yl)benzyl)piperazin-1-yl)methanone (0.209 mmol, 100 mg) in dichloromethane (1 mL). After 1 hour, 1-amino-2-methylpropan-2-ol (0.626 mmol, 55.8 mg) was added and stirring continued for 1 hour. The reaction mixture was diluted with methanol and purified by SCX chromatography, followed by silica chromatography (eluting with dichloromethane increasing to dichloromethane/methanol 10%) to afford the title compound (33 mg).

MS (ESI) m/z 595.5 [M+H]⁺

The following compound was prepared in a similar manner:

7B: 1-(2-Fluoro-4-(4-(4-(1,1,1,3,3,3-hexafluoro-2-hydroxypropan-2-yl)benzyl)piperazine-1-carbonyl)phenyl)-3-(3-hydroxy-3-methylbutyl)urea MS (ESI) m/z 609.5 [M+H]⁺

7C: 1-((1-Cyanocyclopropyl)methyl)-3-(2-fluoro-4-(4-(4-(1,1,1,3,3,3-hexafluoro-2-hydroxypropan-2-yl)benzyl)piperazine-1-carbonyl)phenyl)urea

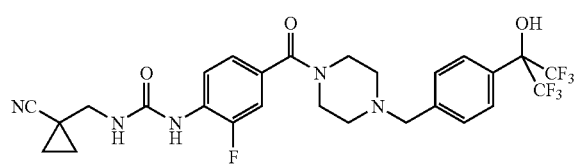

MS (ESI) m/z 602.5 [M+H]⁺

The 1-(aminomethyl)cyclopropanecarbonitrile used in this synthesis was prepared as described in WO 2009/024550 (N.V. Organon).

7D: 1-(2-Fluoro-4-(4-(4-(1,1,1,3,3,3-hexafluoro-2-hydroxypropan-2-yl)benzyl)piperazine-1-carbonyl)phenyl)-3-(6-(trifluoromethyl)pyridin-3-yl)urea MS (ESI) m/z 668.2 [M+H]⁺

7E: 1-(2-fluoro-4-(4-(4-(1,1,1,3,3,3-hexafluoro-2-hydroxypropan-2-yl)benzyl)piperazine-1-carbonyl)phenyl)-3-(2-(pyridin-4-yl)ethyl)urea MS (ESI) m/z 628.7 [M+H]⁺

EXAMPLE 8

1-(2-Fluoro-4-(4-(4-(1,1,1,3,3,3-hexafluoro-2-hydroxypropan-2-yl)benzyl)piperazine-1-carbonyl)phenyl)-3-isopropylurea

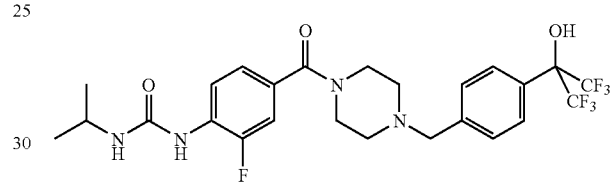

(4-Amino-3-fluorophenyl)(4-(4-(1,1,1,3,3,3-hexafluoro-2-hydroxypropan-2-yl)-benzyl)piperazin-1-yl)methanone (0.209 mmol, 0.1 g) and N,N-diisopropylethylamine (0.709 mmol, 0.117 mL, 0.092 g) were stirred in dichloromethane at room temperature. Triphosgene (0.077 mmol, 0.023 g) was added and the reaction mixture stirred for 30 minutes. Isopropylamine (0.417 mmol, 0.036 mL, 0.025 g) was added and the reaction stirred for a further 30 minutes. The reaction was concentrated at reduced pressure and the resulting residue was purified by silica chromatography (eluting with a solvent gradient from dichloromethane to 5% methanol/dichloromethane) to afford the title compound (20 mg). MS (ESI) m/z 565.5 [M+H]⁺

The following compounds were prepared in a similar manner:

8B: 1-(Cyclopropylmethyl)-3-(2-fluoro-4-(4-(4-(1,1,1,3,3,3-hexafluoro-2-hydroxypropan-2-yl)benzyl)piperazine-1-carbonyl)phenyl)urea MS (ESI) m/z 577.5 [M+H]⁺

8C: (S)-1-(2-Fluoro-4-(4-(4-(1,1,1,3,3,3-hexafluoro-2-hydroxypropan-2-yl)benzyl)piperazine-1-carbonyl)phenyl)-3-(2-hydroxypropyl)urea MS (ESI) m/z 581.5 [M+H]⁺

8D: (R)-1-(2-Fluoro-4-(4-(4-(1,1,1,3,3,3-hexafluoro-2-hydroxypropan-2-yl)benzyl)-piperazine-1-carbonyl)phenyl)-3-(2-hydroxypropyl)urea MS (ESI) m/z 581.3 [M+H]⁺

8E: N-(2-Fluoro-4-(4-(4-(1,1,1,3,3,3-hexafluoro-2-hydroxypropan-2-yl)benzyl)piperazine-1-carbonyl)phenyl)piperidine-1-carboxamide

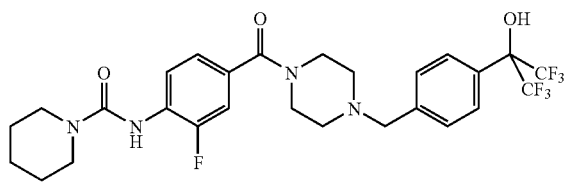 [SMILES: O=C(Nc1ccc(C(=O)N2CCN(Cc3ccc(C(O)(C(F)(F)F)C(F)(F)F)cc3)CC2)cc1F)N1CCCCC1]

MS (ESI) m/z 591.5 [M+H]$^+$

8F: 1-(2-Fluoro-4-(4-(4-(1,1,1,3,3,3-hexafluoro-2-hydroxypropan-2-yl)benzyl)piperazine-1-carbonyl)phenyl)-3-((1-hydroxycyclopropyl)methyl)urea MS (ESI) m/z 593.8 [M+H]$^+$ 8G: 1-(2-(2,4-Difluorophenyl)-2-hydroxyethyl)-3-(2-fluoro-4-(4-(4-(1,1,1,3,3,3-hexafluoro-2-hydroxypropan-2-yl)benzyl)piperazine-1-carbonyl)phenyl)urea MS (ESI) m/z 679.2 [M+H]$^+$ 8H: 1-(2-fluoro-4-(4-(4-(1,1,1,3,3,3-hexafluoro-2-hydroxypropan-2-yl)benzyl)piperazine-1-carbonyl)phenyl)-3-(4-hydroxy-4-methylcyclohexyl)urea

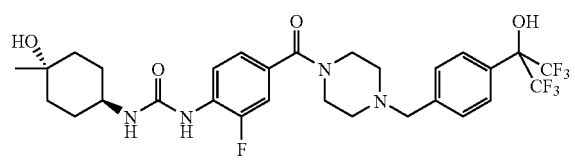 [SMILES: C[C@]1(O)CC[C@H](NC(=O)Nc2ccc(C(=O)N3CCN(Cc4ccc(C(O)(C(F)(F)F)C(F)(F)F)cc4)CC3)cc2F)CC1]

MS (ESI) m/z 635.5 [M+H]$^+$

8I: 1-(2-Fluoro-4-(4-(4-(1,1,1,3,3,3-hexafluoro-2-hydroxypropan-2-yl)benzyl)piperazine-1-carbonyl)phenyl)-3-(2-(4-fluorophenyl)-2-hydroxypropyl)urea MS (ESI) m/z 674.8 [M+H]$^+$ 8J: 1-(2-Amino-2-methylpropyl)-3-(2-fluoro-4-(4-(4-(1,1,1,3,3,3-hexafluoro-2-hydroxypropan-2-yl)benzyl)piperazine-1-carbonyl)phenyl)urea MS (ESI) m/z 594.2 [M+H]$^+$

EXAMPLE 9

(S)-1-(2-Fluoro-4-(4-(4-(1,1,1,3,3,3-hexafluoro-2-hydroxypropan-2-yl)benzyl)piperazine-1-carbonyl)phenyl)-3-(1-hydroxybutan-2-yl)urea

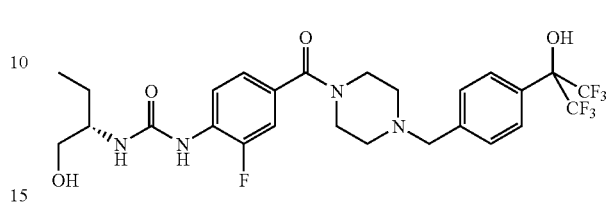

A: (4-Amino-3-fluorophenyl)(4-(4-(2-(tert-butyldimethylsilyloxy)-1,1,1,3,3,3-hexafluoropropan-2-yl)benzyl)piperazin-1-yl)methanone

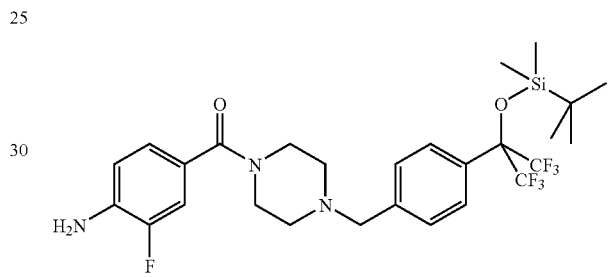

1,8-Diazabicyclo[5.4.0]undec-7-ene (1.559 mmol, 0.233 mL, 237 mg) was added to a cooled (ice/slurry) solution of (4-amino-3-fluorophenyl)(4-(4-(1,1,1,3,3,3-hexafluoro-2-hydroxypropan-2-yl)benzyl)piperazin-1-yl)methanone (1.199 mmol, 575 mg) and tert-butyldimethylchlorosilane (1.559 mmol, 235 mg) in dichloromethane (20 mL) under nitrogen. The resulting solution was stirred for 15 minutes prior to the removal of the external cooling bath. The reaction was allowed to warm to room temperature and stirred for 16 hours. The reaction mixture was diluted with dichloromethane (100 ml) and washed with 0.5M hydrochloric acid (100 ml), 0.5M sodium hydroxide (100 ml) and brine (100 ml). The organic phase was dried on magnesium sulfate, filtered and concentrated under vacuum to give a crude oil. This oil was purified by SCX chromatography to afford the title compound (534 mg). MS (ESI) m/z 594.3 [M+H]$^+$ B: (S)-1-(4-(4-(4-(2-(tert-Butyldimethylsilyloxy)-1,1,1,3,3,3-hexafluoropropan-2-yl)benzyl)-piperazine-1-carbonyl)-2-fluorophenyl)-3-(1-hydroxybutan-2-yl)urea

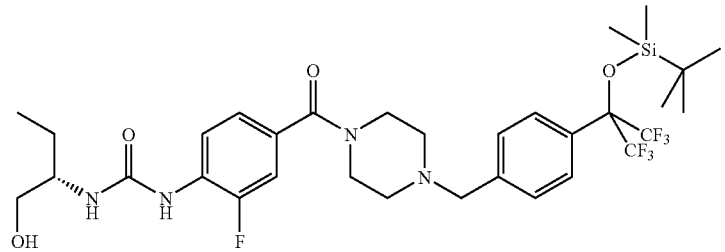 [SMILES: CC[C@@H](CO)NC(=O)Nc1ccc(C(=O)N2CCN(Cc3ccc(C(O[Si](C)(C)C(C)(C)C)(C(F)(F)F)C(F)(F)F)cc3)CC2)cc1F]

A solution of (4-amino-3-fluorophenyl)(4-(4-(2-(tert-butyldimethylsilyloxy)-1,1,1,3,3,3-hexafluoropropan-2-yl)benzyl)piperazin-1-yl)methanone (0.421 mmol, 250 mg) and 4-nitrophenyl carbonochloridate (0.421 mmol, 85 mg) in dichloromethane (1 ml) was stirred at room temperature for 30 minutes. (S)-2-Aminobutan-1-ol (0.839 mmol, 0.079 mL, 74.8 mg) was added, followed by triethylamine (1.263 mmol, 0.176 mL, 128 mg) and the reaction stirred at room temperature overnight. The reaction mixture was diluted with dichloromethane (3 ml) and washed with saturated aqueous sodium hydrogen carbonate solution (5 ml). The organic phase was concentrated and the resulting residue was purified by column chromatography (2-5% methanol in dichloromethane) to afford the title compound (215 mg). MS (ESI) m/z 709.2 [M+H]$^+$ C: (S)-1-(2-Fluoro-4-(4-(4-(1,1,1,3,3,3-hexafluoro-2-hydroxypropan-2-yl)benzyl)-piperazine-1-carbonyl)phenyl)-3-(1-hydroxybutan-2-yl)urea To a stirring solution of (S)-1-(4-(4-(4-(2-(tert-butyldimethylsilyloxy)-1,1,1,3,3,3-hexafluoropropan-2-yl)benzyl)piperazine-1-carbonyl)-2-fluorophenyl)-3-(1-hydroxybutan-2-yl)urea (0.303 mmol, 215 mg) in tetrahydrofuran (1 mL) was added potassium fluoride (50% weight on celite) (1.517 mmol, 176 mg). The resulting suspension was heated to 80° C. for 48 hours. The reaction mixture was filtered through celite and concentrated under vacuum. The resulting residue was purified by SCX chromatography to afford the title compound (132.4 mg).
MS (ESI) m/z 595.0 [M+H]$^+$ The following compounds were prepared in a similar manner:

9B: 1-(2-Fluoro-4-(4-(4-(1,1,1,3,3,3-hexafluoro-2-hydroxypropan-2-yl)benzyl)piperazine-1-carbonyl)phenyl)-3-(2-hydroxycyclobutyl)urea, trans racemate MS (ESI) m/z 593.0 [M+H]$^+$ 9C: 1-(2-Fluoro-4-(4-(4-(1,1,1,3,3,3-hexafluoro-2-hydroxypropan-2-yl)benzyl)piperazine-1-carbonyl)phenyl)-3-(3-hydroxycyclohexyl)urea, mix of 4 diastereomers MS (ESI) m/z 621.0 [M+H]$^+$ 9D: (S)-1-(2-Fluoro-4-(4-(4-(1,1,1,3,3,3-hexafluoro-2-hydroxypropan-2-yl)benzyl)-piperazine-1-carbonyl)phenyl)-3-(1-hydroxy-3,3-dimethylbutan-2-yl)urea MS (ESI) m/z 623.0 [M+H]$^+$ 9E: (S)-1-(2-Fluoro-4-(4-(4-(1,1,1,3,3,3-hexafluoro-2-hydroxypropan-2-yl)benzyl)-piperazine-1-carbonyl)phenyl)-3-(1-hydroxy-3-methylbutan-2-yl)urea MS (ESI) m/z 609.2 [M+H]$^+$ 9F: 1-(2-Fluoro-4-(4-(4-(1,1,1,3,3,3-hexafluoro-2-hydroxypropan-2-yl)benzyl)piperazine-1-carbonyl)phenyl)-3-(4-hydroxycyclohexyl)urea, trans MS (ESI) m/z 621.3 [M+H]$^+$ 9G: 1-(2-Fluoro-4-(4-(4-(1,1,1,3,3,3-hexafluoro-2-hydroxypropan-2-yl)benzyl)piperazine-1-carbonyl)phenyl)-3-((1S,2S)-2-hydroxycyclohexyl)urea, trans racemate MS (ESI) m/z 621.3 [M+H]$^+$ 9H: 1-(2-Fluoro-4-(4-(4-(1,1,1,3,3,3-hexafluoro-2-hydroxypropan-2-yl)benzyl)piperazine-1-carbonyl)phenyl)-3-((1S,2S)-2-(hydroxymethyl)cyclohexyl)urea, trans racemate MS (ESI) m/z 635.0 [M+H]$^+$ 9I: 1-(2-Fluoro-4-(4-(4-(1,1,1,3,3,3-hexafluoro-2-hydroxypropan-2-yl)benzyl)piperazine-1-carbonyl)phenyl)-3-((1 S,2R)-2-hydroxycyclopentyl)urea MS (ESI) m/z 607.2 [M+H]$^+$ 9J: 1-(2-fluoro-4-(4-(4-(1,1,1,3,3,3-hexafluoro-2-hydroxypropan-2-yl)benzyl)piperazine-1-carbonyl)phenyl)-3-(1-(hydroxymethyl)cyclopentyl)urea MS (ESI) m/z 621.3 [M+H]$^+$ 9K: 1-(1-Cyclopropyl-3-hydroxypropyl)-3-(2-fluoro-4-(4-(4-(1,1,1,3,3,3-hexafluoro-2-hydroxypropan-2-yl)benzyl)piperazine-1-carbonyl)phenyl)urea, racemate MS (ESI) m/z 621.3 [M+H]$^+$ 9L: (R)-1-(2-Fluoro-4-(4-(4-(1,1,1,3,3,3-hexafluoro-2-hydroxypropan-2-yl)benzyl)piperazine-1-carbonyl)phenyl)-3-(1-hydroxypentan-2-yl)urea MS (ESI) m/z 609.0 [M+H]$^+$ 9M: (S)-1-(2-Fluoro-4-(4-(4-(1,1,1,3,3,3-hexafluoro-2-hydroxypropan-2-yl)benzyl)piperazine-1-carbonyl)phenyl)-3-(1-hydroxypentan-2-yl)urea MS (ESI) m/z 609.0 [M+H]$^+$ 9N: 1-(2-Fluoro-4-(4-(4-(1,1,1,3,3,3-hexafluoro-2-hydroxypropan-2-yl)benzyl)piperazine-1-carbonyl)phenyl)-3-((1-hydroxycycloheptyl)methyl)urea MS (ESI) m/z 649.3 [M+H]$^+$ 9O: 1-(2-Fluoro-4-(4-(4-(1,1,1,3,3,3-hexafluoro-2-hydroxypropan-2-yl)benzyl)piperazine-1-carbonyl)phenyl)-3-(3-hydroxycyclobutyl)urea, trans MS (ESI) m/z 593.0 [M+H]$^+$ 9P: 1-(2-fluoro-4-(4-(4-(1,1,1,3,3,3-hexafluoro-2-hydroxypropan-2-yl)benzyl)piperazine-1-carbonyl)phenyl)-3-((1-(hydroxymethyl)cyclopentyl)methyl)urea MS (ESI) m/z 635.0 [M+H]$^+$ 9O: 1-(2-Fluoro-4-(4-(4-(1,1,1,3,3,3-hexafluoro-2-hydroxypropan-2-yl)benzyl)piperazine-1-carbonyl)phenyl)-3-((1-(hydroxymethyl)cyclobutyl)methyl)urea MS (ESI) m/z 621.3 [M+H]$^+$ 9R: 1-(2-Fluoro-4-(4-(4-(1,1,1,3,3,3-hexafluoro-2-hydroxypropan-2-yl)benzyl)piperazine-1-carbonyl)phenyl)-3-((1-hydroxycyclobutyl)methyl)urea MS (ESI) m/z 607.0 [M+H]$^+$ 9S: 1-(2-Fluoro-4-(4-(4-(1,1,1,3,3,3-hexafluoro-2-hydroxypropan-2-yl)benzyl)piperazine-1-carbonyl)phenyl)-3-(2-(4-hydroxytetrahydro-2H-pyran-4-yl)ethyl)urea MS (ESI) m/z 651.5 [M+H]$^+$ 9T: 1-(2-Fluoro-4-(4-(4-(1,1,1,3,3,3-hexafluoro-2-hydroxypropan-2-yl)benzyl)piperazine-1-carbonyl)phenyl)-3-(tetrahydrothiophen-3-yl)urea MS (ESI) m/z 609.3 [M+H]$^+$ 9U: 1-(2-Fluoro-4-(4-(4-(1,1,1,3,3,3-hexafluoro-2-hydroxypropan-2-yl)benzyl)piperazine-1-carbonyl)phenyl)-3-((1R,2R)-2-hydroxycyclopentyl)urea MS (ESI) m/z 607.0 [M+H]$^+$ 9V: 1-(3-Cyclopropyl-1-methyl-1H-pyrazol-5-yl)-3-(2-fluoro-4-(4-(4-(1,1,1,3,3,3-hexafluoro-2-hydroxypropan-2-yl)benzyl)piperazine-1-carbonyl)phenyl)urea

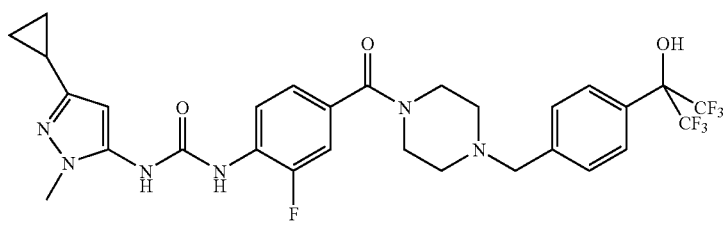 [SMILES: Cn1nc(C2CC2)cc1NC(=O)Nc1ccc(C(=O)N2CCN(Cc3ccc(C(O)(C(F)(F)F)C(F)(F)F)cc3)CC2)cc1F]

MS (ESI) m/z 643.3 [M+H]$^+$

9W: 1-(2-(Dimethylamino)-2-methylpropyl)-3-(2-fluoro-4-(4-(4-(1,1,1,3,3,3-hexafluoro-2-hydroxypropan-2-yl)benzyl)piperazine-1-carbonyl)phenyl)urea MS (ESI) m/z 622.5 [M+H]+

9X: 1-(2-Fluoro-4-(4-(4-(1,1,1,3,3,3-hexafluoro-2-hydroxypropan-2-yl)benzyl)piperazine-1-carbonyl)phenyl)-3-(2-(2-oxoimidazolidin-1-yl)ethyl)urea

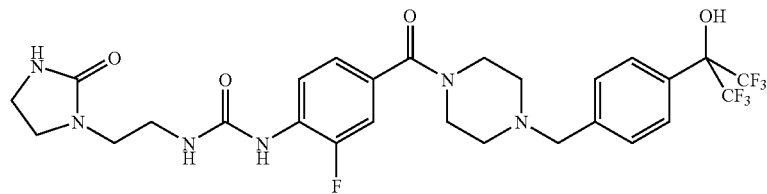 [SMILES: O=C(NCCN1CCNC1=O)Nc1ccc(C(=O)N2CCN(Cc3ccc(C(O)(C(F)(F)F)C(F)(F)F)cc3)CC2)cc1F]

MS (ESI) m/z 635.2 [M+H]+

9Y: 1-(2-Fluoro-4-(4-(4-(1,1,1,3,3,3-hexafluoro-2-hydroxypropan-2-yl)benzyl)piperazine-1-carbonyl)phenyl)-3-(2-methoxyethyl)urea MS (ESI) m/z 580.8 [M+H]+

9Z: 1-(2-Fluoro-4-(4-(4-(1,1,1,3,3,3-hexafluoro-2-hydroxypropan-2-yl)benzyl)piperazine-1-carbonyl)phenyl)-3-((5-methylisoxazol-3-yl)methyl)urea

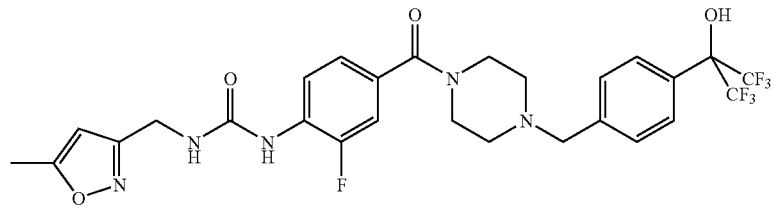 [SMILES: Cc1cc(CNC(=O)Nc2ccc(C(=O)N3CCN(Cc4ccc(C(O)(C(F)(F)F)C(F)(F)F)cc4)CC3)cc2F)no1]

MS (ESI) m/z 618.3 [M+H]+

9AA: 1-((1,4-Dioxan-2-yl)methyl)-3-(2-fluoro-4-(4-(4-(1,1,1,3,3,3-hexafluoro-2-hydroxypropan-2-yl)benzyl)piperazine-1-carbonyl)phenyl)urea

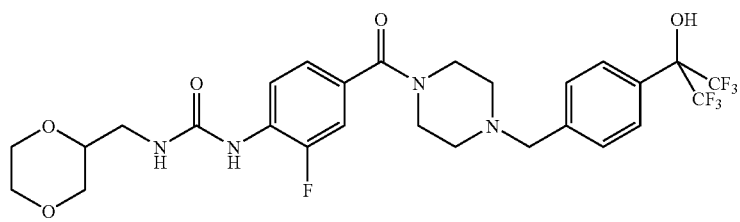 [SMILES: O=C(NCC1COCCO1)Nc1ccc(C(=O)N2CCN(Cc3ccc(C(O)(C(F)(F)F)C(F)(F)F)cc3)CC2)cc1F]

MS (ESI) m/z 623.2 [M+H]+

9AB: 1-(2-Fluoro-4-(4-(4-(1,1,1,3,3,3-hexafluoro-2-hydroxypropan-2-yl)benzyl)piperazine-1-carbonyl)phenyl)-3-(3,3,3-trifluoro-2-hydroxypropyl)urea MS (ESI) m/z 635.2 [M+H]$^+$ 9AC: (S)-1-(2-Fluoro-4-(4-(4-(1,1,1,3,3,3-hexafluoro-2-hydroxypropan-2-yl)benzyl)piperazine-1-carbonyl)phenyl)-3-((tetrahydrofuran-2-yl)methyl)urea MS (ESI) m/z 607.0 [M+H]$^+$ 9AD: (R)-1-(2-Fluoro-4-(4-(4-(1,1,1,3,3,3-hexafluoro-2-hydroxypropan-2-yl)benzyl)piperazine-1-carbonyl)phenyl)-3-((tetrahydrofuran-2-yl)methyl)urea MS (ESI) m/z 607.0 [M+H]$^+$ 9AE: 1-(2-Fluoro-4-(4-(4-(1,1,1,3,3,3-hexafluoro-2-hydroxypropan-2-yl)benzyl)piperazine-1-carbonyl)phenyl)-3-(tetrahydro-2H-pyran-4-yl)urea MS (ESI) m/z 607.0 [M+H]$^+$ 21AF: 1-(2-Fluoro-4-(4-(4-(1,1,1,3,3,3-hexafluoro-2-hydroxypropan-2-yl)benzyl)piperazine-1-carbonyl)phenyl)-3-(2-morpholinoethyl)urea MS (ESI) m/z 636.2 [M+H]$^+$ 9AG: 1-(2-Fluoro-4-(4-(4-(1,1,1,3,3,3-hexafluoro-2-hydroxypropan-2-yl)benzyl)piperazine-1-carbonyl)phenyl)-3-(3-(2-oxopyrrolidin-1-yl)propyl)urea MS (ESI) m/z 648.2 [M+H]$^+$ 9AH: 1-(2-Fluoro-4-(4-(4-(1,1,1,3,3,3-hexafluoro-2-hydroxypropan-2-yl)benzyl)piperazine-1-carbonyl)phenyl)-3-(2-(furan-2-yl)-2-hydroxyethyl)urea MS (ESI) m/z 633.2 [M+H]$^+$

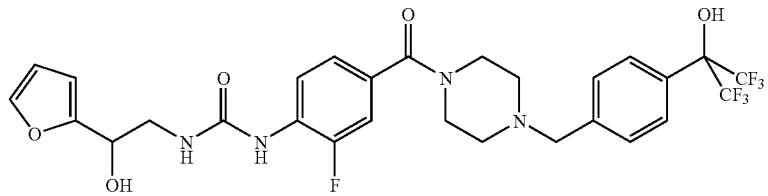 [SMILES: O=C(NCC(O)c1ccco1)Nc1ccc(C(=O)N2CCN(Cc3ccc(C(O)(C(F)(F)F)C(F)(F)F)cc3)CC2)cc1F]

9AI: (R)-1-(2-Fluoro-4-(4-(4-(1,1,1,3,3,3-hexafluoro-2-hydroxypropan-2-yl)benzyl)piperazine-1-carbonyl)phenyl)-3-(2-hydroxy-2-phenylethyl)urea MS (ESI) m/z 643.2 [M+H]$^+$ 9AJ: (S)-1-(2-Fluoro-4-(4-(4-(1,1,1,3,3,3-hexafluoro-2-hydroxypropan-2-yl)benzyl)piperazine-1-carbonyl)phenyl)-3-(2-hydroxy-2-phenylethyl)urea MS (ESI) m/z 643.3 [M+H]$^+$ 9AK: 1-(2-Fluoro-4-(4-(4-(1,1,1,3,3,3-hexafluoro-2-hydroxypropan-2-yl)benzyl)piperazine-1-carbonyl)phenyl)-3-(2-hydroxy-1-(tetrahydrofuran-3-yl)ethyl)urea

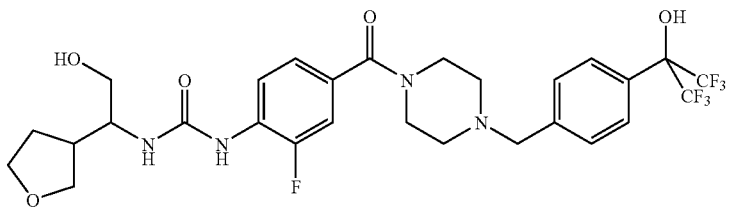 [SMILES: O=C(Nc1ccc(C(=O)N2CCN(Cc3ccc(C(O)(C(F)(F)F)C(F)(F)F)cc3)CC2)cc1F)NC(CO)C1CCOC1]

MS (ESI) m/z 637.2 [M+H]$^+$

9AL: 1-(2-Fluoro-4-(4-(4-(1,1,1,3,3,3-hexafluoro-2-hydroxypropan-2-yl)benzyl)piperazine-1-carbonyl)phenyl)-3-(2-methoxy-2-methylpropyl)urea MS (ESI) m/z 609.2 [M+H]+

9AM: 1-((3-(2-Fluoro-4-(4-(4-(1,1,1,3,3,3-hexafluoro-2-hydroxypropan-2-yl)benzyl)piperazine-1-carbonyl)phenyl)ureido)methyl)-N,N-dimethylcyclopropanecarboxamide

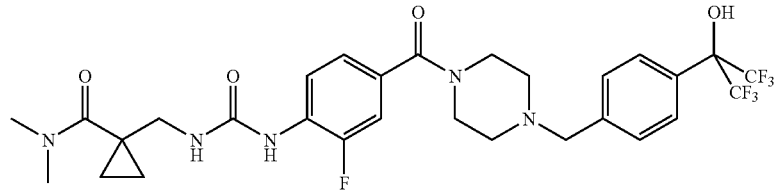 [SMILES: CN(C)C(=O)C1(CNC(=O)Nc2ccc(C(=O)N3CCN(Cc4ccc(C(O)(C(F)(F)F)C(F)(F)F)cc4)CC3)cc2F)CC1]

MS (ESI) m/z 648.3 [M+H]+

9AN: (R)-1-(2-Fluoro-4-(4-(4-(1,1,1,3,3,3-hexafluoro-2-hydroxypropan-2-yl)benzyl)piperazine-1-carbonyl)phenyl)-3-(6-oxopiperidin-3-yl)urea

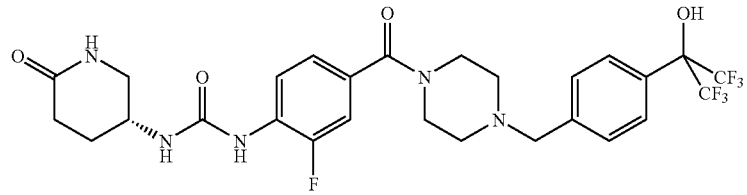 [SMILES: O=C1CC[C@@H](NC(=O)Nc2ccc(C(=O)N3CCN(Cc4ccc(C(O)(C(F)(F)F)C(F)(F)F)cc4)CC3)cc2F)CN1]

MS (ESI) m/z 620.2 [M+H]+

9AO: (S)-1-(2-Fluoro-4-(4-(4-(1,1,1,3,3,3-hexafluoro-2-hydroxypropan-2-yl)benzyl)piperazine-1-carbonyl)phenyl)-3-(6-oxopiperidin-3-yl)urea MS (ESI) m/z 620.2 [M+H]+

9AP: (S)-1-(2-Fluoro-4-(4-(4-(1,1,1,3,3,3-hexafluoro-2-hydroxypropan-2-yl)benzyl)piperazine-1-carbonyl)phenyl)-3-(2-oxopyrrolidin-3-yl)urea MS (ESI) m/z 606.2 [M+H]+

9AQ: 1-(2-Fluoro-4-(4-(4-(1,1,1,3,3,3-hexafluoro-2-hydroxypropan-2-yl)benzyl)piperazine-1-carbonyl)phenyl)-3-(5-oxo-1-propylpyrrolidin-3-yl)urea MS (ESI) m/z 648.2 [M+H]+

9AR: 1-(2-Fluoro-4-(4-(4-(1,1,1,3,3,3-hexafluoro-2-hydroxypropan-2-yl)benzyl)piperazine-1-carbonyl)phenyl)-3-(4-hydroxytetrahydrofuran-3-yl)urea, trans racemate MS (ESI) m/z 608.8 [M+H]+

9AS: 1-(2-Fluoro-4-{4-[4-(2,2,2-trifluoro-1-hydroxy-1-trifluoromethyl-ethyl)-benzyl]-piperazine-1-carbonyl}-phenyl)-3-(3-methyl-1,1-dioxo-tetrahydro-1λ6-thiophen-3-yl)-urea MS (ESI) m/z 655.0 [M+H]+

9AT: 1-(1,1-Dioxo-tetrahydro-1λ6-thiophen-3-yl)-3-(2-fluoro-4-{4-[4-(2,2,2-trifluoro-1-hydroxy-1-trifluoromethyl-ethyl)-benzyl]-piperazine-1-carbonyl}-Phenyl)-urea MS (ESI) m/z 641.0 [M+H]+

9AU: 1-((5-((Dimethylamino)methyl)furan-2-yl)methyl)-3-(2-fluoro-4-(4-(4-(1,1,1,3,3,3-hexafluoro-2-hydroxypropan-2-yl)benzyl)piperazine-1-carbonyl)phenyl)urea MS (ESI) m/z 660.2 [M+H]+

9AV: (S)-1-(2,3-Dihydroxypropyl)-3-(2-fluoro-4-(4-(4-(1,1,1,3,3,3-hexafluoro-2-hydroxypropan-2-yl)benzyl)piperazine-1-carbonyl)phenyl)urea MS (ESI) m/z 597.2 [M+H]+

9AW: 1-(2-Fluoro-4-(4-(4-(1,1,1,3,3,3-hexafluoro-2-hydroxypropan-2-yl)benzyl)piperazine-1-carbonyl)phenyl)-3-(2-hydroxy-3-methoxypropyl)urea MS (ESI) m/z 611.2 [M+H]+

9AX: (R)-1-(2-Fluoro-4-(4-(4-(1,1,1,3,3,3-hexafluoro-2-hydroxypropan-2-yl)benzyl)piperazine-1-carbonyl)phenyl)-3-(tetrahydrofuran-3-yl)urea MS (ESI) m/z 593.2 [M+H]+

9AY: 1-(1,1-Dioxo-hexahydro-1$\lambda_6$-thiopyran-4-yl)-3-(2-fluoro-4-{4-[4-(2,2,2-trifluoro-1-hydroxy-1-trifluoromethyl-ethyl)-benzyl]-piperazine-1-carbonyl}-phenyl)-urea MS (ESI) m/z 655.0 [M+H]+

9AZ: 1-(2-Fluoro-4-(4-(4-(1,1,1,3,3,3-hexafluoro-2-hydroxypropan-2-yl)benzyl)piperazine-1-carbonyl)phenyl)-3-(tetrahydro-2H-thiopyran-4-yl)urea MS (ESI) m/z 623.0 [M+H]+

9BA: 1-(2-Fluoro-4-(4-(4-(1,1,1,3,3,3-hexafluoro-2-hydroxypropan-2-yl)benzyl)piperazine-1-carbonyl)phenyl)-3-((4-hydroxytetrahydro-2H-Pyran-4-yl)methyl)urea MS (ESI) m/z 637.3 [M+H]+

9BB: 1-(2-Fluoro-4-(4-(4-(1,1,1,3,3,3-hexafluoro-2-hydroxypropan-2-yl)benzyl)piperazine-1-carbonyl)phenyl)-3-((4-(hydroxymethyl)tetrahydro-2H-pyran-4-yl)methyl)urea

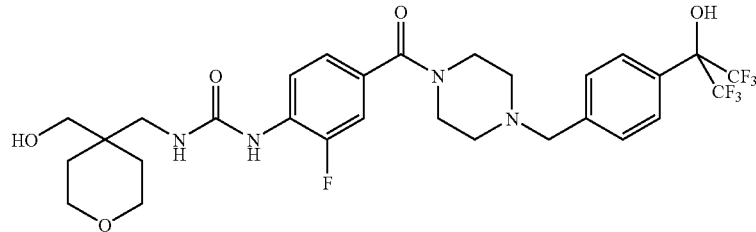 [SMILES: O=C(NCC1(CO)CCOCC1)Nc1ccc(C(=O)N2CCN(Cc3ccc(C(O)(C(F)(F)F)C(F)(F)F)cc3)CC2)cc1F]

MS (ESI) m/z 651.2 [M+H]+

9BC: 1-(1,1-Dioxo-tetrahydro-1$\lambda^6$-thiophen-3-ylmethyl)-3-(2-fluoro-4-{4-[4-(2,2,2-trifluoro-1-hydroxy-1-trifluoromethyl-ethyl)-benzyl]-piperazine-1-carbonyl}-phenyl)-urea MS (ESI) m/z 655.0 [M+H]+

9BD: (S)-1-(2-Fluoro-4-(4-(4-(1,1,1,3,3,3-hexafluoro-2-hydroxypropan-2-yl)benzyl)piperazine-1-carbonyl)phenyl)-3-(tetrahydrofuran-3-yl)urea MS (ESI) m/z 593.5 [M+H]+

9BE: 1-(2-Fluoro-4-(4-(4-(1,1,1,3,3,3-hexafluoro-2-hydroxypropan-2-yl)benzyl)piperazine-1-carbonyl)phenyl)-3-(4-hydroxytetrahydrofuran-3-yl)urea, cis racemate MS (ESI) m/z 608.8 [M+H]+

9BF: 3-(3-(2-fluoro-4-(4-(4-(1,1,1,3,3,3-hexafluoro-2-hydroxypropan-2-yl)benzyl)piperazine-1-carbonyl)phenyl)ureido)-2,2-dimethylpropanamide MS (ESI) m/z 622.3 [M+H]+

9BG: 1-(2-Fluoro-4-(4-(4-(1,1,1,3,3,3-hexafluoro-2-hydroxypropan-2-yl)benzyl)piperazine-1-carbonyl)phenyl)-3-((1S,2R)-2-hydroxycyclohexyl)urea, cis racemate MS (ESI) m/z 621.3 [M+H]+

9BH: 1-(2-Fluoro-4-(4-(4-(1,1,1,3,3,3-hexafluoro-2-hydroxypropan-2-yl)benzyl)piperazine-1-carbonyl)phenyl)-3-(2-hydroxybutyl)urea, racemate MS (ESI) m/z 595.0 [M+H]+

EXAMPLE 10

N-(2-Fluoro-4-(4-(4-(1,1,1,3,3,3-hexafluoro-2-hydroxypropan-2-yl)benzyl)piperazine-1-carbonyl)phenyl)-3,3-dimethylbutanamide

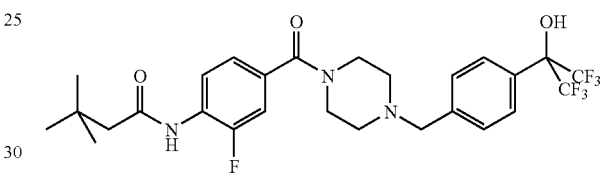

(4-Amino-3-fluorophenyl)(4-(4-(1,1,1,3,3,3-hexafluoro-2-hydroxypropan-2-yl)-benzyl)piperazin-1-yl)methanone (100 mg, 0.209 mmol) was stirred in dichloromethane (1 mL) with triethylamine (53 mg, 0.073 mL, 0.521 mmol) at 0° C. 3,3-Dimethylbutanoyl chloride (42 mg, 0.313 mmol) was added and the reaction allowed to stir for 2 hours. The reaction mixture was washed with water and the organic phase was purified by reverse phase acidic preparative HPLC to afford the title compound (12 mg). MS (ESI) m/z 578.5 [M+H]+

The following compounds were prepared in a similar manner:

10B: N-(2-Fluoro-4-(4-(4-(1,1,1,3,3,3-hexafluoro-2-hydroxypropan-2-yl)benzyl)piperazine-1-carbonyl)phenyl)cyclohexanecarboxamide MS (ESI) m/z 590.5 [M+H]+

10C: N-(2-Fluoro-4-(4-(4-(1,1,1,3,3,3-hexafluoro-2-hydroxypropan-2-yl)benzyl)piperazine-1-carbonyl)phenyl)cyclopentanecarboxamide MS (ESI) m/z 576.3 [M+H]+

10D: 2-Cyclopentyl-N-(2-fluoro-4-(4-(4-(1,1,1,3,3,3-hexafluoro-2-hydroxypropan-2-yl)benzyl)piperazine-1-carbonyl)phenyl)acetamide MS (ESI) m/z 590.5 [M+H]$^+$ 10E: N-(2-Fluoro-4-(4-(4-(1,1,1,3,3,3-hexafluoro-2-hydroxypropan-2-yl)benzyl)piperazine-1-carbonyl)phenyl)isoxazole-5-carboxamide MS (ESI) m/z 575.3 [M+H]$^+$ 10F: N-(2-Fluoro-4-(4-(4-(1,1,1,3,3,3-hexafluoro-2-hydroxypropan-2-yl)benzyl)piperazine-1-carbonyl)phenyl)furan-3-carboxamide MS (ESI) m/z 574.2 [M+H]$^+$ 10G: N-(2-Fluoro-4-(4-(4-(1,1,1,3,3,3-hexafluoro-2-hydroxypropan-2-yl)benzyl)piperazine-1-carbonyl)phenyl)-5-methylisoxazole-3-carboxamide MS (ESI) m/z 589.3 [M+H]$^+$ 10H: N-(2-Fluoro-4-(4-(4-(1,1,1,3,3,3-hexafluoro-2-hydroxypropan-2-yl)benzyl)piperazine-1-carbonyl)phenyl)furan-2-carboxamide
MS (ESI) m/z 574.2 [M+H]$^+$ 10I: N-(2-Fluoro-4-(4-(4-(1,1,1,3,3,3-hexafluoro-2-hydroxypropan-2-yl)benzyl)piperazine-1-carbonyl)phenyl)thiophene-2-carboxamide MS (ESI) m/z 590.5 [M+H]$^+$ 10J: N-(2-Fluoro-4-(4-(4-(1,1,1,3,3,3-hexafluoro-2-hydroxypropan-2-yl)benzyl)piperazine-1-carbonyl)phenyl)-2-phenylacetamide MS (ESI) m/z 598.2 [M+H]$^+$ 10K: N-(2-Fluoro-4-(4-(4-(1,1,1,3,3,3-hexafluoro-2-hydroxypropan-2-yl)benzyl)piperazine-1-carbonyl)phenyl)-2-(tetrahydro-2H-pyran-4-yl)acetamide MS (ESI) m/z 606.0 [M+H]$^+$ 10L: 5-Cyclopropyl-N-(2-fluoro-4-(4-(4-(1,1,1,3,3,3-hexafluoro-2-hydroxypropan-2-yl)benzyl)piperazine-1-carbonyl)phenyl)isoxazole-3-carboxamide MS (ESI) m/z 615.2 [M+H]$^+$ 10M: N-(2-Fluoro-4-(4-(4-(1,1,1,3,3,3-hexafluoro-2-hydroxypropan-2-yl)benzyl)piperazine-1-carbonyl)phenyl)isonicotinamide

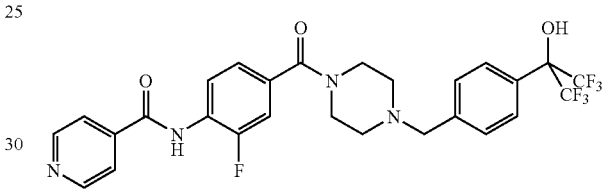

MS (ESI) m/z 584.8 [M+H]$^+$

EXAMPLE 11

N-(2-Fluoro-4-(4-(4-(1,1,1,3,3,3-hexafluoro-2-hydroxypropan-2-yl)benzyl)piperazine-1-carbonyl)phenyl)-4-methylpentanamide

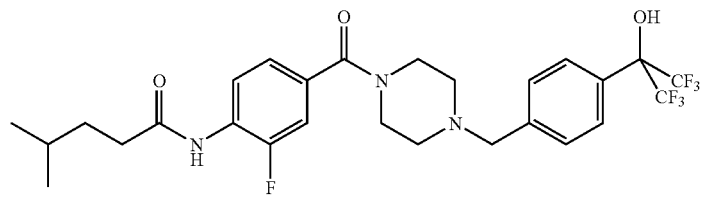 [SMILES: CC(C)CCC(=O)Nc1ccc(C(=O)N2CCN(Cc3ccc(C(O)(C(F)(F)F)C(F)(F)F)cc3)CC2)cc1F]

4-Methylvaleric acid (4.30 mmol, 0.543 mL, 0.5 g) was stirred in dichloromethane (5 mL) at 0° C. Oxalyl chloride (21.52 mmol, 1.848 mL, 2.73 g) was added. The reaction mixture allowed to warm to room temperature and stirred for 18 hours. The reaction mixture was concentrated under vacuum to give the intermediate 4-methylpentanoyl chloride.

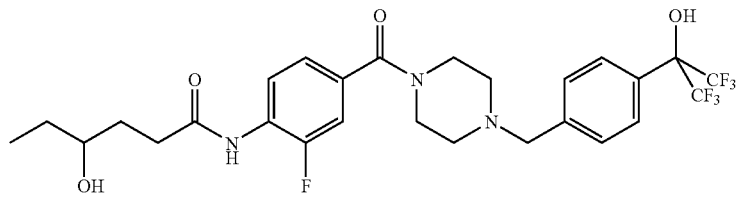 [SMILES: CCC(O)CCC(=O)Nc1ccc(C(=O)N2CCN(Cc3ccc(C(O)(C(F)(F)F)C(F)(F)F)cc3)CC2)cc1F]

A mixture of 4-methylpentanoyl chloride (1.564 mmol, 0.211 g), (4-amino-3-fluorophenyl)(4-(4-(1,1,1,3,3,3-hexafluoro-2-hydroxypropan-2-yl)benzyl)piperazin-1-yl)methanone (1.043 mmol, 0.5 g) and triethylamine (2.086 mmol, 0.290 mL, 0.211 g) were stirred in dichloromethane at 0° C. for 1 hour. The reaction mixture was washed with water, dried over sodium sulfate, concentrated under vacuum and purified by silica chromatography (eluting with a solvent gradient from dichloromethane to 5% methanol/dichloromethane) to afford the title compound (54 mg).

MS (ESI) m/z 578.3 [M+H]$^+$

The following compounds were prepared in a similar manner:

11B: N-(2-Fluoro-4-(4-(4-(1,1,1,3,3,3-hexafluoro-2-hydroxypropan-2-yl)benzyl)piperazine-1-carbonyl)phenyl)-3-(1-methylcyclopropyl)propanamide MS (ESI) m/z 590.7 [M+H]$^+$ 11C: 3-Cyclopropyl-N-(2-fluoro-4-(4-(4-(1,1,1,3,3,3-hexafluoro-2-hydroxypropan-2-yl)benzyl)piperazine-1-carbonyl)phenyl)propanamide MS (ESI) m/z 576.5 [M+H]$^+$ 11D: N-(2-Fluoro-4-(4-(4-(1,1,1,3,3,3-hexafluoro-2-hydroxypropan-2-yl)benzyl)piperazine-1-carbonyl)phenyl)-2-(pyridin-4-yl)acetamide MS (ESI) m/z 599.3 [M+H]$^+$

EXAMPLE 12

N-(2-Fluoro-4-(4-(4-(1,1,1,3,3,3-hexafluoro-2-hydroxypropan-2-yl)benzyl)piperazine-1-carbonyl)phenyl)-4-hydroxyhexanamide, racemate

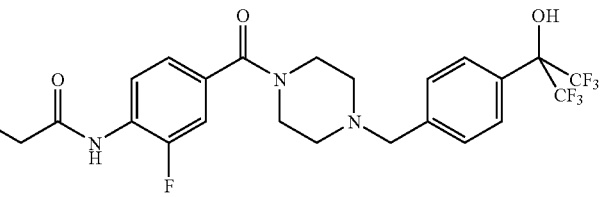

(4-Amino-3-fluorophenyl)(4-(4-(1,1,1,3,3,3-hexafluoro-2-hydroxypropan-2-yl)-benzyl)piperazin-1-yl)methanone (0.417 mmol, 0.2 g) was stirred in toluene (5 mL). Timethylaluminium (0.834 mmol, 0.834 mL, 1 M in heptane) was added and the reaction stirred for 10 minutes at room temperature. (4-amino-3-fluorophenyl)(4-(4-(1,1,1,3,3,3-hexafluoro-2-hydroxypropan-2-yl)benzyl)piperazin-1-yl)methanone (0.417 mmol, 0.2 g) was added and the reaction heated to reflux for 1 hour. The reaction mixture was quenched with water. Ethyl acetate was added and the layers separated. The organic was concentrated under vacuum and purified by silica chromatography (eluting with a solvent gradient from dichloromethane to 5% methanol/dichloromethane) to afford the title compound (24 mg).

MS (ESI) m/z 594.7 [M+H]$^+$

EXAMPLE 13

Cyclopropylmethyl 2-fluoro-4-(4-(4-(1,1,1,3,3,3-hexafluoro-2-hydroxypropan-2-yl)benzyl)piperazine-1-carbonyl)phenylcarbamate

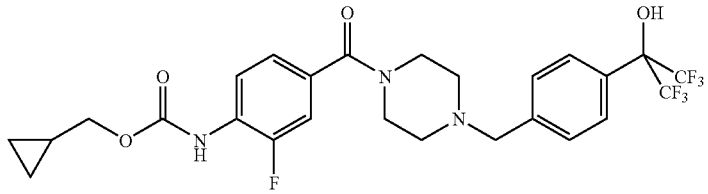 [SMILES: O=C(Nc1ccc(C(=O)N2CCN(Cc3ccc(C(O)(C(F)(F)F)C(F)(F)F)cc3)CC2)cc1F)OCC1CC1]

(4-Amino-3-fluorophenyl)(4-(4-(1,1,1,3,3,3-hexafluoro-2-hydroxypropan-2-yl)-benzyl)piperazin-1-yl)methanone (0.209 mmol, 0.1 g) and 4-nitrophenyl carbonochloridate (0.209 mmol, 0.042 g) were combined and stirred in dichloromethane (1 mL) at room temperature for 30 minutes. Cyclopropylmethanol (0.417 mmol, 0.030 g) and N,N-dimethylaminopyridine (0.003 g, 0.0209 mmol) were added and the reaction stirred at room temperature for 17 hours. The reaction was concentrated under vacuum and purified by acidic reverse phase HPLC to afford the title compound (22 mg).

MS (ESI) m/z 578.2 [M+H]$^+$

The following compound was prepared in a similar manner:

13B: 4-Hydroxycyclohexyl 2-fluoro-4-(4-(4-(1,1,1,3,3,3-hexafluoro-2-hydroxypropan-2-yl)benzyl)piperazine-1-carbonyl)phenylcarbamate

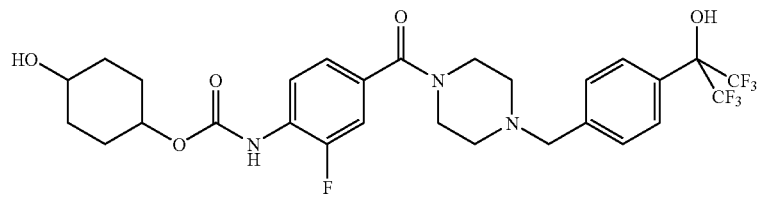 [SMILES: O=C(Nc1ccc(C(=O)N2CCN(Cc3ccc(C(O)(C(F)(F)F)C(F)(F)F)cc3)CC2)cc1F)OC1CCC(O)CC1]

MS (ESI) m/z 622.0 [M+H]+

EXAMPLE 14

1-(2-Chloro-4-(4-(4-(1,1,1,3,3,3-hexafluoro-2-hydroxypropan-2-yl)benzyl)piperazine-1-carbonyl)phenyl)-3-(2-hydroxy-2-methylpropyl)urea

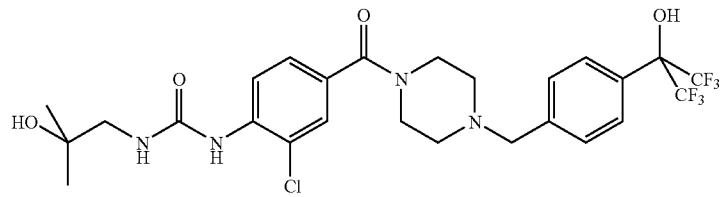 [SMILES: CC(C)(O)CNC(=O)Nc1ccc(C(=O)N2CCN(Cc3ccc(C(O)(C(F)(F)F)C(F)(F)F)cc3)CC2)cc1Cl]

A: tert-Butyl 4-(4-amino-3-chlorobenzoyl)piperazine-1-carboxylate

To a stirred mixture of 4-amino-3-chlorobenzoic acid (58.3 mmol, 10 g), tert-butyl piperazine-1-carboxylate (58.3 mmol, 10.86 g) and triethylamine (146 mmol, 20.31 mL, 14.74 g) in dichloromethane (200 mL) was added N-(3-dimethylaminopropyl)-N'-ethylcarbodiimide hydrochloride (69.9 mmol, 13.41 g). The reaction was stirred for 24 hours then was diluted with ethyl acetate and water. The organic layer was separated, dried (magnesium sulfate) and concentrated under reduced pressure. Diethyl ether was added and the solid was filtered off to give the title compound (15.4 g).

MS (ESI) m/z 340.3 [M+H]+

B: (4-Amino-3-chlorophenyl)(piperazin-1-yl)methanone

A mixture of tert-butyl 4-(4-amino-3-chlorobenzoyl)piperazine-1-carboxylate (45.3 mmol, 15.4 g), dichloromethane (50 mL) and 2,2,2-trifluoroacetic acid (136 mmol, 15.50 g) were stirred for 24 hours. The reaction was concentrated under reduced pressure and was then basified with potassium carbonate (aqueous). The aqueous was extracted with ethyl acetate and then dichloromethane to give the title compound (7.7 g).

MS (ESI) m/z 240.1 [M+H]+

C: (4-Amino-3-chlorophenyl)(4-(4-(1,1,1,3,3,3-hexafluoro-2-hydroxypropan-2-yl)benzyl)piperazin-1-yl)methanone A mixture of (4-amino-3-chlorophenyl)(piperazin-1-yl)methanone (6.67 mmol, 1.6 g), 2-(4-(bromomethyl)phenyl)-1,1,1,3,3,3-hexafluoropropan-2-ol (6.67 mmol, 2.250 g), sodium hydrogencarbonate (20.02 mmol, 1.682 g) and sodium iodide (0.334 mmol, 0.050 g) in acetonitrile (50 mL) was stirred for 24 hours. The reaction was concentrated under reduced pressure and dichloromethane was added. The mixture was filtered and the filtrate was chromatographed on silica eluting with dichloromethane to dichloromethane/ethyl acetate to give the title compound (1.66 g).

MS (ESI) m/z 496.3 [M+H]+

D: (4-Amino-3-chlorophenyl)(4-(4-(2-(tert-butyldimethylsilyloxy)-1,1,1,3,3,3-hexafluoropropan-2-yl)benzyl)piperazin-1-yl)methanone 1,8-Diazabicyclo[5.4.0]undec-7-ene (4.22 mmol, 0.631 mL, 0.643 g) was added to a cooled (ice/slurry) solution of (4-amino-3-chlorophenyl)(4-(4-(1,1,1,3,3,3-hexafluoro-2-hydroxypropan-2-yl)benzyl)piperazin-1-yl)methanone (3.25 mmol, 1.61 g) and tert-butyldimethylchlorosilane (4.22 mmol, 0.636 g) in dichloromethane (20 mL) under nitrogen. The resulting solution was stirred for 15 minutes prior to the removal of the external cooling bath. The reaction was allowed to warm to room temperature and stirred for 16 hours. The reaction mixture was diluted with dichloromethane (100 ml) and washed with 0.5M hydrochloric acid (100 ml), 0.5M sodium hydroxide (100 ml) and brine (100 ml). The organic phase was dried on magnesium sulfate, filtered and concentrated under vacuum to give a crude oil. This oil was purified by SCX chromatography to afford the title compound (1.616 g).

MS (ESI) m/z 610.0 [M+H]+

E: 1-(4-(4-(4-(2-(tert-Butyldimethylsilyloxy)-1,1,1,3,3-hexafluoropropan-2-yl)benzyl)piperazine-1-carbonyl)-2-chlorophenyl)-3-(2-hydroxy-2-methylpropyl)urea (4-Amino-3-chlorophenyl)(4-(4-(2-(tert-butyldimethylsilyloxy)-1,1,1,3,3,3-hexafluoropropan-2-yl)benzyl)piperazin-1-yl)methanone (0.410 mmol, 250 mg) and 4-nitrophenyl carbonochloridate (0.410 mmol, 83 mg) in dichloromethane (1 ml) were combined and heated at reflux for 1 hour. The reaction was allowed to cool to room temperature before the addition of 1-amino-2-methylpropan-2-ol (0.820 mmol, 73.1 mg) and triethylamine (0.410 mmol, 0.057 mL, 41.5 mg). The reaction was stirred at room temperature overnight. The reaction mixture was concentrated under vacuum and the resulting residue was purified by column chromatography (2-5% methanol in dichloromethane) to afford the title compound (190 mg).

MS (ESI) m/z 725.3 [M+H]$^+$

F: 1-(2-Chloro-4-(4-(4-(1,1,1,3,3,3-hexafluoro-2-hydroxypropan-2-yl)benzyl)piperazine-1-carbonyl)phenyl)-3-(2-hydroxy-2-methylpropyl)urea To a stirring solution of 1-(4-(4-(4-(2-(tert-butyldimethylsilyloxy)-1,1,1,3,3,3-hexafluoropropan-2-yl)benzyl)piperazine-1-carbonyl)-2-chlorophenyl)-3-(2-hydroxy-2-methylpropyl)urea (0.262 mmol, 190 mg) in tetrahydrofuran (1 mL) was added potassium fluoride (50% weight on celite) (0.524 mmol, 60.9 mg). The resulting suspension was stirred at room temperature for 16 hours. The reaction mixture was filtered through celite and concentrated under vacuum. The resulting residue was purified by SCX chromatography, followed by column chromatography (5-10% methanol in dichloromethane) to afford the title compound (55.5 mg).

MS (ESI) m/z 611.2 [M+H]$^+$

The following compounds were prepared in a similar manner:

14B: (S)-1-(2-Chloro-4-(4-(4-(1,1,1,3,3,3-hexafluoro-2-hydroxypropan-2-yl)benzyl)piperazine-1-carbonyl)phenyl)-3-(2-hydroxypropyl)urea MS (ESI) m/z 597.2 [M+H]$^+$ 14C: (R)-1-(2-Chloro-4-(4-(4-(1,1,1,3,3,3-hexafluoro-2-hydroxypropan-2-yl)benzyl)piperazine-1-carbonyl)phenyl)-3-(2-hydroxypropyl)urea MS (ESI) m/z 597.2 [M+H]$^+$ 14D: 1-(2-Chloro-4-(4-(4-(1,1,1,3,3,3-hexafluoro-2-hydroxypropan-2-yl)benzyl)piperazine-1-carbonyl)phenyl)-3-(3-hydroxy-3-methylbutyl)urea MS (ESI) m/z 625.0 [M+H]$^+$ 14E: 1-(2-Chloro-4-(4-(4-(1,1,1,3,3,3-hexafluoro-2-hydroxypropan-2-yl)benzyl)piperazine-1-carbonyl)phenyl)-3-((1-hydroxycyclopropyl)methyl)urea MS (ESI) m/z 609.2 [M+H]$^+$ 14F: 1-(2-Chloro-4-(4-(4-(1,1,1,3,3,3-hexafluoro-2-hydroxypropan-2-yl)benzyl)piperazine-1-carbonyl)phenyl)-3-(4-hydroxycyclohexyl)urea, trans MS (ESI) m/z 637.0 [M+H]$^+$ 14H: 1-(2-Chloro-4-[4-[4-(2,2,2-trifluoro-1-hydroxy-1-trifluoromethyl-ethyl)-benzyl]-piperazine-1-carbonyl]-phenyl)-3-(4-hydroxy-1,1-dioxo-tetrahydro-1λ$^6$-thiophen-3-yl)-urea, cis racemate

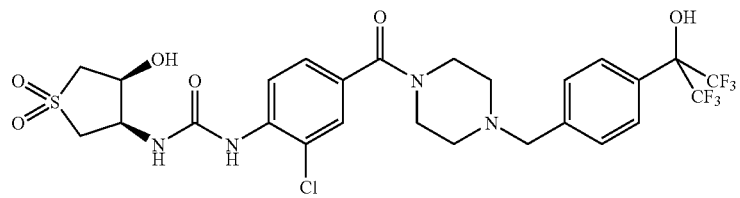 [SMILES: O=C(Nc1ccc(C(=O)N2CCN(Cc3ccc(C(O)(C(F)(F)F)C(F)(F)F)cc3)CC2)cc1Cl)N[C@H]1CS(=O)(=O)C[C@H]1O]

MS (ESI) m/z 673.3 [M+H]$^+$

EXAMPLE 15

1-Butyl-3-(5-(4-(4-(1,1,1,3,3,3-hexafluoro-2-hydroxypropan-2-yl)benzyl)piperazine-1-carbonyl)pyridin-2-yl)urea

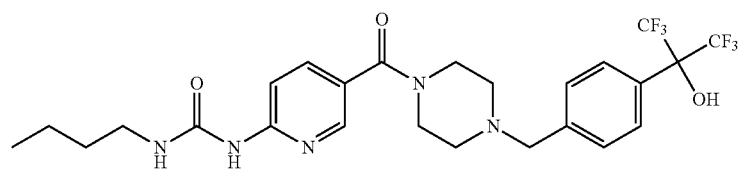 [SMILES: CCCCNC(=O)Nc1ccc(C(=O)N2CCN(Cc3ccc(C(O)(C(F)(F)F)C(F)(F)F)cc3)CC2)cn1]

A: (6-Aminopyridin-3-yl)(4-benzylpiperazin-1-yl) methanone

To a stirred solution of 6-aminonicotinic acid (1 g, 7.24 mmol) in dimethylformamide (50 mL) was added 1-benzylpiperazine (1.258 mL, 1.276 g, 7.24 mmol), triethylamine (2.018 mL, 1.465 g, 14.48 mmol), 1-hydroxybenzotriazole hydrate (1.109 g, 7.24 mmol) and N-(3-dimethylaminopropyl)-N'-ethylcarbodiimide hydrochloride (1.388 g, 7.24 mmol). After being stirred overnight at room temperature the reaction mixture was concentrated under vacuum. Purification by silica chromatography (eluting with 5% methanol/dichloromethane) gave the title compound (1.8 g).

MS (ESI) m/z 297.6 [M+H]+

B: 1-(5-(4-Benzylpiperazine-1-carbonyl)pyridin-2-yl)-3-butylurea (6-Aminopyridin-3-yl)(4-benzylpiperazin-1-yl)methanone (90 mg, 0.304 mmol) and n-butyl isocyanate (103 µl, 91 mg, 0.914 mmol) were combined in dimethylformamide (3 mL) and the mixture was heated to 100° C. for 6 hours. After this time the mixture was taken up in dichloromethane/methanol and loaded on to a strong cation exchange column (2 g) and washed with dichloromethane/methanol. Elution of the column with 2M ammonia in methanol gave a residue that was further purified by silica chromatography (eluting with 5% methanol/dichloromethane) to give the title compound (58 mg).

MS (ESI) m/z 396.4 [M+H]+

C: 1-Butyl-3-(5-(piperazine-1-carbonyl)pyridin-2-yl) urea 1-(5-(4-Benzylpiperazine-1-carbonyl)pyridin-2-yl)-3-butylurea (58 mg, 0.147 mmol) and palladium on carbon 10% (15.61 mg, 0.015 mmol) were stirred in ethanol (2.5 mL containing 3 drops of 5M hydrochoric acid) under a hydrogen atmosphere at 5 bar at room temperature overnight. The mixture was filtered and the residue was taken up in dichloromethane/methanol and loaded on to a strong cation exchange column (2 g) and washed with dichloromethane/methanol. Elution of the column with 2M ammonia in methanol gave the title compound (44 mg).

MS (ESI) m/z 306.5 [M+H]+

D: 1-Butyl-3-(5-(4-(4-(1,1,1,3,3,3-hexafluoro-2-hydroxypropan-2-yl)benzyl)piperazine-1-carbonyl)pyridin-2-yl)urea 1-Butyl-3-(5-(piperazine-1-carbonyl)pyridin-2-yl)urea (45 mg, 0.147 mmol), 2-(4-(bromomethyl)phenyl)-1,1,1,3,3,3-hexafluoropropan-2-ol (55 mg, 0.162 mmol), potassium carbonate (61 mg, 0.442 mmol) and sodium iodide (4 mg, 0.029 mmol) were stirred together in acetonitrile (1.5 mL) at reflux for 2 hours. After this time the mixture was cooled to room temperature and diluted with water and ethyl acetate. The organic layer was separated, dried and concentrated under reduced pressure. The residue was purified by silica chromatography eluting with 5% methanol in dichloromethane to give the title compound (29 mg).

MS (ESI) m/z 562.3 [M+H]+

EXAMPLE 16

(R)-1-(Cyclopropylmethyl)-3-(4-(4-(4-(1,1,1,3,3,3-hexafluoro-2-hydroxypropan-2-yl)benzyl)-3-(hydroxymethyl)piperazine-1-carbonylphenyl)urea

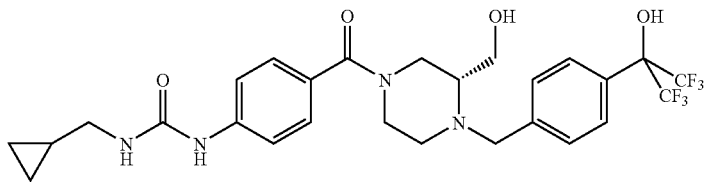 [SMILES: O=C(NCC1CC1)Nc1ccc(C(=O)N2CCN(Cc3ccc(C(O)(C(F)(F)F)C(F)(F)F)cc3)[C@@H](CO)C2)cc1]

A: (R)-1,1,1,3,3,3-Hexafluoro-2-(4-((2-(hydroxymethyl)piperazin-1-ylmethyl)phenyl)-propan-2-ol To a stirred solution of (R)-tert-butyl 3-(hydroxymethyl)piperazine-1-carboxylate (231 mg, 1.07 mmol), 2-(4-(bromomethyl)phenyl)-1,1,1,3,3,3-hexafluoropropan-2-ol (400 mg, 1.19 mmol) and sodium iodide (18 mg, 0.12 mmol) in acetonitrile (10 mL) was added potassium carbonate (655 mg, 4.75 mmol). The reaction mixture was stirred at room temperature for 3 days, before being diluted with dichloromethane (10 mL), filtered through cotton wool and concentrated under reduced pressure. The residue was purified by flash column chromatography (eluting with dichloromethane to 10% methanol in dichloromethane) to afford the intermediate (R)-tert-butyl 4-(4-(1,1,1,3,3,3-hexafluoro-2-hydroxypropan-2-yl)benzyl)-3-(hydroxymethyl)piperazine-1-carboxylate (250 mg, 0.53 mmol). To a stirred solution of (R)-tert-butyl 4-(4-(1,1,1,3,3,3-hexafluoro-2-hydroxypropan-2-yl)benzyl)-3-(hydroxymethyl)piperazine-1-carboxylate (220 mg, 0.466 mmol) in dichloromethane (3 mL), was added trifluoroacetic acid (3 mL, 38.3 mmol). The reaction mixture was stirred at room temperature for 5 hours before being purified directly by SCX chromatography, eluting with 2N ammonia in methanol solution to afford the title compound (165 mg). MS (ESI) m/z 373.3 [M+H]+

B: (R)-1-(Cyclopropylmethyl)-3-(4-(4-(4-(1,1,1,3,3,3-hexafluoro-2-hydroxypropan-2-yl)benzyl)-3-(hydroxymethyl)piperazine-1-carbonyl)phenyl)urea To a solution of 4-(3-(cyclopropylmethyl)ureido)benzoic acid (0.487 mmol, 114 mg), (R)-1,1,1,3,3,3-hexafluoro-2-(4-((2-(hydroxymethyl)piperazin-1-yl)methyl)phenyl)propan-2-ol (0.443 mmol, 165 mg) and triethylamine (1.330 mmol, 0.185 mL, 135 mg) in dichloromethane (4 mL) was added 1-propanephosphonic acid cyclic anhydride (0.665 mmol, 0.395 mL, 423 mg, 50% solution in ethyl acetate). The reaction was stirred for 3 hours and then was diluted with dichloromethane/saturated sodium hydrogen carbonate (aqueous). The organic layer was separated, dried (magnesium sulfate) and concentrated under reduced pressure. The residue was purified by silica column chromatography (eluting with ethyl acetate to 5% methanol/ethyl acetate and basic reverse phase HPLC to afford the title compound (92 mg).

MS (ESI) m/z 589.3 [M+H]+

EXAMPLE 17

(R)-1-(cyclopropylmethyl)-3-(4-(4-(4-(1,1,1,3,3,3-hexafluoro-2-hydroxypropan-2-yl)benzyl)-2-methylpiperazine-1-carbonyl)phenyl)urea

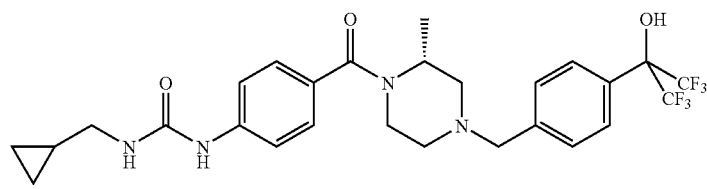 [SMILES: C[C@@H]1CN(Cc2ccc(C(O)(C(F)(F)F)C(F)(F)F)cc2)CCN1C(=O)c1ccc(NC(=O)NCC2CC2)cc1]

A: (R)-1,1,1,3,3,3-Hexafluoro-2-(4-((3-methylpiperazin-1-yl)methyl)phenyl)propan-2-ol (R)-2-Methylpiperazine (37.9 mmol, 3.8 g), 2-(4-(bromomethyl)phenyl)-1,1,1,3,3,3-hexafluoropropan-2-ol (37.9 mmol, 12.79 g) and potassium carbonate (76 mmol, 10.49 g) were stirred at room temperature in acetonitrile (50 mL) overnight. The reaction mixture was diluted with ethyl acetate and filtered through dicalite. The filtrate was concentrated under vacuum. The resulting residue was purified by silica chromatography (eluting with a solvent gradient from dichloromethane to 85/15/1.5 dichloromethane/methanol/ammonia) to afford the title compound (4.06 g).

MS (ESI) m/z 357.0 [M+H]$^+$

B: (R)-1-(Cyclopropylmethyl)-3-(4-(4-(4-(1,1,1,3,3,3-hexafluoro-2-hydroxypropan-2-yl)benzyl)-2-methylpiperazine-1-carbonyl)phenyl)urea (R)-1,1,1,3,3,3-Hexafluoro-2-(4-((3-methylpiperazin-1-yl)methyl)phenyl)propan-2-ol (0.427 mmol, 0.152 g), 4-(3-(cyclopropylmethyl)ureido)benzoic acid (0.427 mmol, 0.1 g) and triethylamine (1.281 mmol, 0.178 mL, 0.130 g) were combined in dichloromethane and stirred at room temperature. 1-Propanephosphonic acid cyclic anhydride (0.640 mmol, 0.381 mL, 0.407 g; 50% solution in ethyl acetate) was added and the reaction allowed to stir for 1 hour. The reaction mixture was washed with saturated sodium bicarbonate solution, dried over sodium sulfate and concentrated under vacuum. The resulting residue was purified by silica chromatography (eluting with a solvent gradient from dichloromethane to 5% methanol/dichloromethane) to afford the title compound (38 mg).

MS (ESI) m/z 573.2 [M+H]$^+$

EXAMPLE 18

(S)-1-(Cyclopropylmethyl)-3-(4-(4-(4-(1,1,1,3,3,3-hexafluoro-2-hydroxypropan-2-yl)benzyl)-2-methylpiperazine-1-carbonyl)phenyl)urea

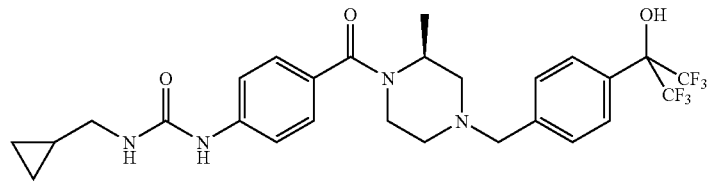 [SMILES: C[C@H]1CN(Cc2ccc(C(O)(C(F)(F)F)C(F)(F)F)cc2)CCN1C(=O)c1ccc(NC(=O)NCC2CC2)cc1]

A: (S)-1,1,1,3,3,3-Hexafluoro-2-(4-((3-methylpiperazin-1-yl)methyl)phenyl)propan-2-ol (S)-2-Methylpiperazine (28 mmol, 2.8 g), 2-(4-(bromomethyl)phenyl)-1,1,1,3,3,3-hexafluoropropan-2-ol (28 mmol, 9.42 g) and potassium carbonate (55.9 mmol, 9.42 g) were stirred at room temperature in acetonitrile (50 mL) overnight The reaction mixture was diluted with ethyl acetate and filtered through dicalite. The filtrate was concentrated under vacuum and the resulting residue was purified by silica chromatography (eluting with a solvent gradient from dichloromethane to 85/15/1.5 dichloromethane/methanol/ammonia) to afford the title compound (4.55 g). MS (ESI) m/z 357.0 [M+H]$^+$

B: (S)-1-(Cyclopropylmethyl)-3-(4-(4-(4-(1,1,1,3,3,3-hexafluoro-2-hydroxypropan-2-yl)benzyl)-2-methylpiperazine-1-carbonyl)phenyl)urea (S)-1,1,1,3,3,3-Hexafluoro-2-(4-((3-methylpiperazin-1-yl)methyl)phenyl)propan-2-ol (0.854 mmol, 0.304 g), 4-(3-(cyclopropylmethyl)ureido)benzoic acid (0.854 mmol, 0.2 g)

and triethylamine (2.56 mmol, 0.356 mL, 0.259 g) were combined in dichloromethane and stirred at room temperature. 1-Propanephosphonic acid cyclic anhydride (1.28 mmol, 0.762 mL, 0.815 g; 50% solution in ethyl acetate) was added and the reaction allowed to stir for 1 hour. The reaction mixture was washed with saturated sodium bicarbonate solution, dried over sodium sulfate and concentrated under vacuum. The resulting residue was purified by silica chromatography (eluting with a solvent gradient from dichloromethane to 5% methanol/dichloromethane) to afford the title compound (32 mg).

MS (ESI) m/z 573.0 [M+H]$^+$

EXAMPLE 19

1-(Cyclopropylmethyl)-3-(4-(-4-(4-(1,1,1,3,3,3-hexafluoro-2-hydroxypropan-2-yl)benzyl)-2,6-cis-dimethylpiperazine-1-carbonyl)phenyl)urea B: 1-(Cyclopropylmethyl)-3-(4-(-4-(4-(1,1,1,3,3,3-hexafluoro-2-hydroxypropan-2-yl)benzyl)-2,6-cis-dimethylpiperazine-1-carbonyl)phenyl)urea 2-(4-((-3,5-cis-Dimethylpiperazin-1-yl)methyl)phenyl)-1,1,1,3,3,3-hexafluoro-propan-2-ol (0.27 mmol, 0.1 g), 4-(3-(cyclopropylmethyl)ureido)benzoic acid (0.27 mmol, 0.063 g) and triethylamine (0.81 mmol, 0.113 mL, 0.082 g) were combined in dichloromethane and stirred at room temperature. 1-Propanephosphonic acid cyclic anhydride (0.405 mmol, 0.241 mL, 0.258 g; 50% solution in ethyl acetate) was added and the reaction allowed to stir for 1 hour. The reaction mixture was washed with saturated sodium bicarbonate solution, dried over sodium sulfate and concentrated under

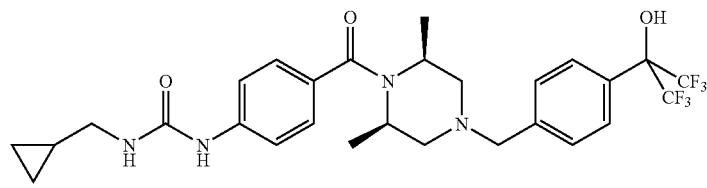 [SMILES: C[C@@H]1CN(Cc2ccc(C(O)(C(F)(F)F)C(F)(F)F)cc2)C[C@H](C)N1C(=O)c1ccc(NC(=O)NCC2CC2)cc1]

A: 2-(4-((-3,5-cis-Dimethylpiperazin-1-yl)methyl) phenyl)-1,1,1,3,3,3-hexafluoropropan-2-ol 2,6-cis-Dimethylpiperazine (40.3 mmol, 4.6 g), 2-(4-(bromomethyl)phenyl)-1,1,1,3,3,3-hexafluoropropan-2-ol (40.3 mmol, 13.58 g) and potassium carbonate (81 mmol, 11.13 g) were combined and stirred overnight at room temperature in acetonitrile (25 mL). The reaction mixture was diluted with ethyl acetate and filtered through dicalite. The filtrate was concentrated under vacuum. The resulting residue was purified by silica chromatography (eluting with a solvent gradient from dichloromethane to 90/10/1 dichloromethane/methanol/ammonia) to afford the title compound (8.91 g).

MS (ESI) m/z 371.1 [M+H]$^+$ vacuum. The resulting residue was purified by acidic preparative HPLC to afford the desired compound (3 mg). MS (ESI) m/z 587.3 [M+H]$^+$

EXAMPLE 20

1-(Cyclopropylmethyl)-3-(4-(4-(4-(1,1,1,3,3,3-hexafluoro-2-hydroxypropan-2-yl)benzyl)-1,4-diazepane-1-carbonyl)phenyl)urea

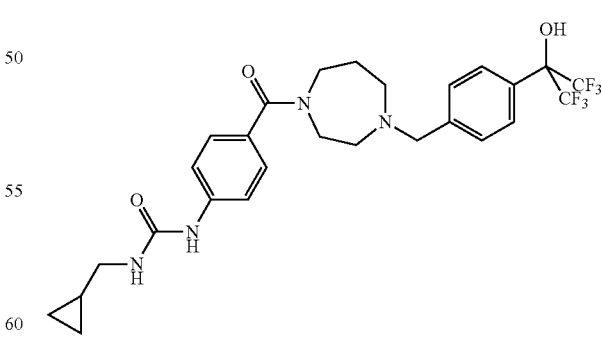

A: tert-Butyl 4-(4-(1,1,1,3,3,3-hexafluoro-2-hydroxypropan-2-yl)benzyl)-1,4-diazepane-1-carboxylate A mixture of tert-butyl 1,4-diazepane-1-carboxylate (24.52 mmol, 4.91 g), 2-(4-(bromomethyl)phenyl)-1,1,1,3,3, 3-hexafluoropropan-2-ol (24.52 mmol, 8.26 g) and sodium hydrogencarbonate (36.8 mmol, 3.09 g) in acetonitrile (100 mL) was stirred for 24 hours then was concentrated under reduced pressure. Dichloromethane was added and the suspension was filtered. The filtrate was concentrated under reduced pressure. The residue was chromatographed on silica eluting with dichloromethane to dichloromethane/methanol (5%) to give the title compound (7.1 g). MS (ESI) m/z 457.2 [M+H]$^+$ B: 2-(4-((1,4-Diazepan-1-yl)methyl)phenyl)-1,1,1,3,3,3-hexafluoropropan-2-ol A mixture of tert-butyl 4-(4-(1,1,1,3,3,3-hexafluoro-2-hydroxypropan-2-yl)benzyl)-1,4-diazepane-1-carboxylate (15.34 mmol, 7 g), dichloromethane (15 mL) and trifluoroacetic acid (15.00 mL) was stirred for 24 hours. The reaction was purified by SCX chromatography to give the title compound (4.2 g). MS (ESI) m/z 357.1 [M+H]$^+$ C: 1-(Cyclopropylmethyl)-3-(4-(4-(4-(1,1,1,3,3,3-hexafluoro-2-hydroxypropan-2-yl)benzyl)-1,4-diazepane-1-carbonyl)phenyl)urea To a mixture of 4-(3-(cyclopropylmethyl)ureido)benzoic acid (2.134 mmol, 0.5 g), 2-(4-((1,4-diazepan-1-yl)methyl)phenyl)-1,1,1,3,3,3-hexafluoropropan-2-ol (2.134 mmol, 0.761 g) and triethylamine (5.34 mmol, 0.744 mL, 0.540 g) in dichloromethane (30 mL) was added N-(3-dimethylaminopropyl)-N'-ethylcarbodiimide hydrochloride (2.56 mmol, 0.491 g). The reaction was stirred for 24 hours then was chromatographed on silica eluting with dichloromethane to dichloromethane/methanol (6%) then re-chromatographed on silica eluting with ethyl acetate to ethyl acetate/methanol (2%) to give the title compound (780 mg). MS (ESI) m/z 573.0 [M+H]$^+$

EXAMPLE 21

1-((3-(2-Fluoro-4-(4-(4-(1,1,1,3,3,3-hexafluoro-2-hydroxypropan-2-yl)benzyl)piperazine-1-carbonyl)phenyl)ureido)methyl)cyclopropanecarboxamide A: 1-((3-(2-Fluoro-4-(piperazine-1-carbonyl)phenyl)ureido)methyl)cyclopropane-carboxamide

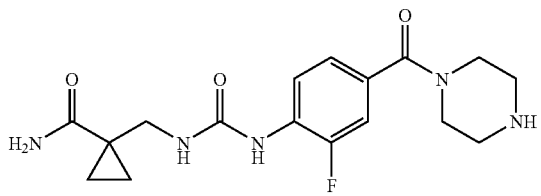

Step 1: Bis(trichloromethyl) carbonate (0.229 mmol, 67.9 mg) was added dropwise to a stirred solution of tert-butyl 4-(4-amino-3-fluorobenzoyl)piperazine-1-carboxylate (0.618 mmol, 200 mg) and N-ethyl-N-isopropylpropan-2-amine (2.103 mmol, 0.348 mL, 272 mg) in dichloromethane (1 mL) at room temperature. After 30 minutes, 1-(aminomethyl)cyclopropanecarbonitrile (0.618 mmol, 59.5 mg) was added and stirring continued overnight. Purification by silica chromatography eluting with dichloromethane to ethyl acetate gave the intermediate tert-butyl 4-(4-(3-((1-cyanocyclopropyl)methyl)ureido)-3-fluorobenzoyl)piperazine-1-carboxylate.

Step 2: The intermediate tert-butyl 4-(4-(3-((1-cyanocyclopropyl)methyl)ureido)-3-fluorobenzoyl)piperazine-1-carboxylate was dissolved in dichloromethane (~2 mL) and trifluoroacetic acid (~0.5 ml) and stirred at ambient temperature overnight. Purification by SCX chromatography yielded the title compound (110 mg). MS (ESI) m/z 364.5 [M+H]$^+$ B: 1-((3-(2-Fluoro-4-(4-(4-(1,1,1,3,3,3-hexafluoro-2-hydroxypropan-2-yl)benzyl)piperazine-1-carbonyl)phenyl)ureido)methyl)cyclopropanecarboxamide 2-(4-(Bromomethyl)phenyl)-1,1,1,3,3,3-hexafluoropropan-2-ol (0.303 mmol, 102 mg), 1-((3-(2-fluoro-4-(piperazine-1-carbonyl)phenyl)ureido)methyl)cyclopropanecarboxamide (0.303 mmol, 110 mg) and potassium carbonate (0.303 mmol, 42 mg) were stirred in acetonitrile (2 ml) at

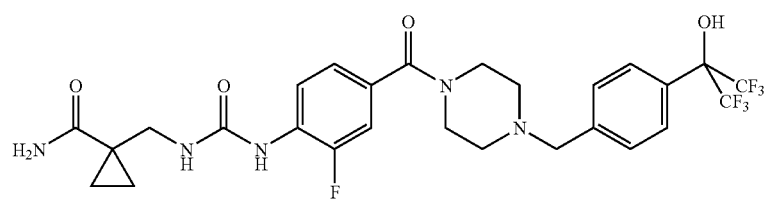 [SMILES: NC(=O)C1(CNC(=O)Nc2ccc(C(=O)N3CCN(Cc4ccc(C(O)(C(F)(F)F)C(F)(F)F)cc4)CC3)cc2F)CC1]

room temperature for 4 hours. The reaction was concentrated under reduced pressure and the residue obtained was purified by silica chromatography eluting with dichloromethane increasing to dichloromethane:methanol (10%). Further purification by HPLC and SCX chromatography yielded the title compound (18 mg). MS (ESI) m/z 620.7 [M+H]$^+$

EXAMPLE 22

1-(5-tert-Butylisoxazol-3-yl)-3-(2-fluoro-4-(4-(4-(1,1,1,3,3,3-hexafluoro-2-hydroxypropan-2-yl)benzyl)piperazine-1-carbonyl)phenyl)urea

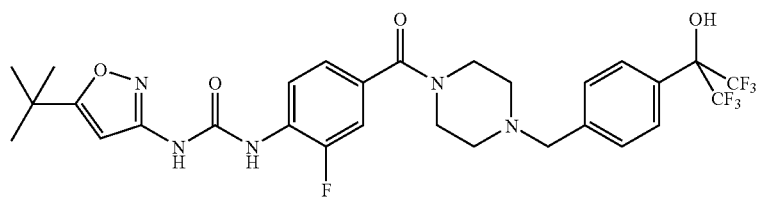 [SMILES: CC(C)(C)c1cc(NC(=O)Nc2ccc(C(=O)N3CCN(Cc4ccc(C(O)(C(F)(F)F)C(F)(F)F)cc4)CC3)cc2F)no1]

(4-Amino-3-fluorophenyl)(4-(4-(1,1,1,3,3,3-hexafluoro-2-hydroxypropan-2-yl)benzyl)piperazin-1-yl)methanone (0.417 mmol, 0.2 g) and 4-nitrophenyl carbono-chloridate (0.417 mmol, 0.084 g) were combined and stirred in tetrahydrofuran (2 mL) at room temperature for 1 hour. 5-tert-Butylisoxazol-3-amine (1.252 mmol, 0.175 g) was added and the reaction heated in the microwave to 120° C. for 10 minutes. The solvent was removed at reduced pressure and the resulting residue purified by silica column chromatography (eluant dichloromethane/methanol 0% to 5%) to afford the title compound (14 mg). MS (ESI) m/z 646.5 [M+H]$^+$ 22B: 1-(2-Fluoro-4-(4-(4-(1,1,1,3,3,3-hexafluoro-2-hydroxypropan-2-yl)benzyl)piperazine-1-carbonyl)phenyl)-3-(Pyridazin-4-yl)urea MS (ESI) m/z 601.2 [M+H]$^+$ 22C: 1-(5-Cyclopropyl-1,3,4-thiadiazol-2-yl)-3-(2-fluoro-4-(4-(4-(1,1,1,3,33-hexafluoro-2-hydroxypropan-2-yl)benzyl)piperazine-1-carbonyl)phenyl)urea MS (ESI) m/z 647.2 [M+H]$^+$ 22D: 1-(2-Fluoro-4-(4-(4-(1,1,1,3,3,3-hexafluoro-2-hydroxypropan-2-yl)benzyl)piperazine-1-carbonyl)phenyl)-3-(3-(methylsulfonyl)phenyl)urea MS (ESI) m/z 677.0 [M+H]$^+$ 22E: 1-(2-Fluoro-4-(4-(4-(1,1,1,3,3,3-hexafluoro-2-hydroxypropan-2-yl)benzyl)piperazine-1-carbonyl)phenyl)-3-(6-methoxypyridin-3-yl)urea

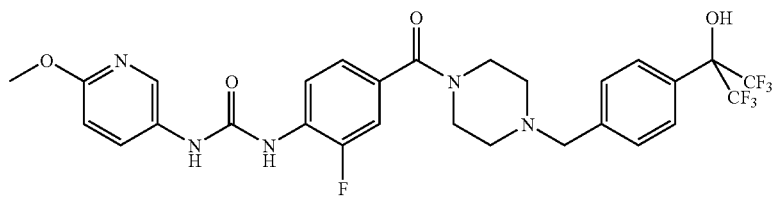 [SMILES: COc1ccc(NC(=O)Nc2ccc(C(=O)N3CCN(Cc4ccc(C(O)(C(F)(F)F)C(F)(F)F)cc4)CC3)cc2F)cn1]

The following compounds were prepared in a similar manner:

22A: 1-(3-Cyanophenyl)-3-(2-fluoro-4-(4-(4-(1,1,1,3,3,3-hexafluoro-2-hydroxypropan-2-yl)benzyl)piperazine-1-carbonyl)phenyl)urea MS (ESI) m/z 624.2 [M+H]$^+$ MS (ESI) m/z 630.0 [M+H]$^+$ 22F: 1-(4-Cyanophenyl)-3-(2-fluoro-4-(4-(4-(1,1,1,3,3,3-hexafluoro-2-hydroxypropan-2-yl)benzyl)piperazine-1-carbonyl)phenyl)urea MS (ESI) m/z 624.0 [M+H]$^+$ 22G: 1-(2-fluoro-4-(4-(4-(1,1,1,3,3,3-hexafluoro-2-hydroxypropan-2-yl)benzyl)piperazine-1-carbonyl)phenyl)-3-(3-isopropyl-1,2,4-thiadiazol-5-yl)urea

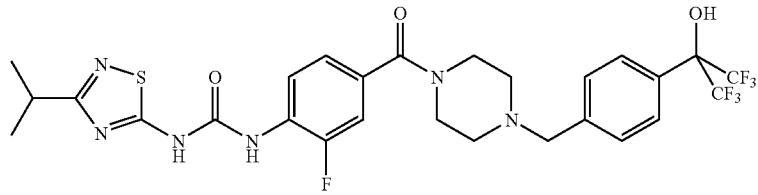 [SMILES: CC(C)c1nsc(NC(=O)Nc2ccc(C(=O)N3CCN(Cc4ccc(C(O)(C(F)(F)F)C(F)(F)F)cc4)CC3)cc2F)n1]

MS (ESI) m/z 649.2 [M+H]+

22H: 1-(2-Fluoro-4-(4-(4-(1,1,1,3,3,3-hexafluoro-2-hydroxypropan-2-yl)benzyl)piperazine-1-carbonyl)phenyl)-3-(2-methylpyridin-4-yl)urea MS (ESI) m/z 614.2 [M+H]+

22I: 1-(2-Fluoro-4-(4-(4-(1,1,1,3,3,3-hexafluoro-2-hydroxypropan-2-yl)benzyl)piperazine-1-carbonyl)phenyl)-3-(2-(trifluoromethyl)pyridin-4-yl)urea MS (ESI) m/z 668.0 [M+H]+

22J: 1-(2-Fluoro-4-(4-(4-(1,1,1,3,3,3-hexa-fluoro-2-hydroxypropan-2-yl)benzyl)piperazine-1-carbonyl)phenyl)-3-(4-methoxyphenyl)urea MS (ESI) m/z 629.2 [M+H]+

EXAMPLE 23

1-(2-Fluoro-4-(4-(4-(1,1,1,3,3,3-hexafluoro-2-hydroxypropan-2-yl)benzyl)piperazine-1-carbonyl)phenyl)-3-phenylurea

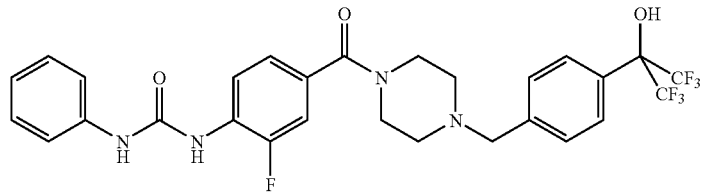 [SMILES: O=C(Nc1ccccc1)Nc1ccc(C(=O)N2CCN(Cc3ccc(C(O)(C(F)(F)F)C(F)(F)F)cc3)CC2)cc1F]

(4-Amino-3-fluorophenyl)(4-(4-(1,1,1,3,3,3-hexafluoro-2-hydroxypropan-2-yl)benzyl)piperazin-1-yl)methanone (0.209 mmol, 0.1 g) and isocyanatobenzene (0.229 mmol, 0.025 mL, 0.027 g) were combined and heated in the microwave at 100° C. for 10 minutes. Further isocyanatobenzene (0.229 mmol, 0.025 mL, 0.027 g) was added and the reaction heated in the microwave for a further 10 minutes at 100° C. The reaction mixture was concentrated under reduced pressure and purified by acidic preparative HPLC to afford the title compound (71 mg). MS (ESI) m/z 599.0 [M+H]+

The following compounds were prepared in a similar manner:

23B: 1-(2-Fluoro-4-(4-(4-(1,1,1,3,3,3-hexafluoro-2-hydroxypropan-2-yl)benzyl)piperazine-1-carbonyl)phenyl)-3-(2-fluorophenyl)urea MS (ESI) m/z 617.3 [M+H]$^+$ 23C: Ethyl 4-(3-(2-fluoro-4-(4-(4-(1,1,1,3,3,3-hexafluoro-2-hydroxypropan-2-yl)benzyl)piperazine-1-carbonyl)phenyl)ureido)benzoate MS (ESI) m/z 671.5 [M+H]$^+$ 23D: Ethyl 3-(3-(2-fluoro-4-(4-(4-(1,1,1,3,3,3-hexafluoro-2-hydroxypropan-2-yl)benzyl)piperazine-1-carbonyl)phenyl)ureido)benzoate MS (ESI) m/z 671.5 [M+H]$^+$ 23E: Ethyl 2-(3-(2-fluoro-4-(4-(4-(1,1,1,3,3,3-hexafluoro-2-hydroxypropan-2-yl)benzyl)piperazine-1-carbonyl)phenyl)ureido)acetate MS (ESI) m/z 609.0 [M+H]$^+$ 23F: 1-(2-Fluoro-4-(4-(4-(1,1,1,3,3,3-hexafluoro-2-hydroxypropan-2-yl)benzyl)piperazine-1-carbonyl)phenyl)-3-(furan-2-ylmethyl)urea MS (ESI) m/z 603.5 [M+H]$^+$

EXAMPLE 24

1-(2-Fluoro-4-(4-(4-(1,1,1,3,3,3-hexafluoro-2-hydroxypropan-2-yl)benzyl)piperazine-1-carbonyl)phenyl)-3-(5-methylisoxazol-3-yl)urea

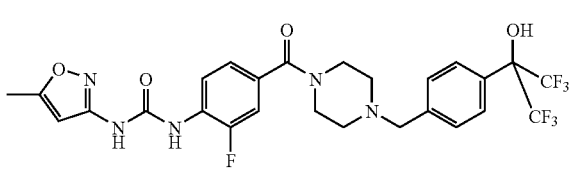 [SMILES: Cc1cc(NC(=O)Nc2ccc(C(=O)N3CCN(Cc4ccc(C(O)(C(F)(F)F)C(F)(F)F)cc4)CC3)cc2F)no1]

Step 1: 5-Methylisoxazol-3-amine (3.06 mmol, 0.3 g) and Hunig's base (3.06 mmol, 0.505 mL, 0.395 g) were stirred in dichloromethane (20 mL) at −78° C. Phenyl carbonochloridate (3.06 mmol, 0.384 mL, 0.479 g) was added dropwise and the reaction allowed to warm to 0° C. then room temperature and stirred for 1 hour. The reaction mixture was washed with saturated sodium bicarbonate solution, dried over sodium sulfate and concentrated under reduced pressure to give the intermediate phenyl 5-methylisoxazol-3-ylcarbamate. MS (ESI) m/z 219.3 [M+H]$^+$ Step 2: The intermediate phenyl 5-methylisoxazol-3-ylcarbamate and (4-amino-3-fluorophenyl)(4-(4-(1,1,1,3,3,3-hexafluoro-2-hydroxypropan-2-yl)benzyl)piperazin-1-yl)methanone (0.417 mmol, 0.2 g) were combined in dioxane (2 mL) and heated to 80° C. overnight in a Reactivial. The solvent was removed at reduced pressure and the resulting residue was purified by silica column chromatography (eluant dichloromethane/methanol 0% to 3%) to afford the title compound (68 mg).
MS (ESI) m/z 604.2 [M+H]$^+$ The following compounds were prepared in a similar manner:

24B: 1-(2-Fluoro-4-(4-(4-(1,1,1,3,3,3-hexafluoro-2-hydroxypropan-2-yl)benzyl)piperazine-1-carbonyl)phenyl)-3-(3-fluoropyridin-4-yl)urea MS (ESI) m/z 618.3 [M+H]$^+$ 24C: 1-(5-Cyanopyridin-2-yl)-3-(2-fluoro-4-(4-(4-(1,1,1,3,3,3-hexafluoro-2-hydroxypropan-2-yl)benzyl)piperazine-1-carbonyl)phenyl)urea MS (ESI) m/z 625.0 [M+H]$^+$ 24D: 1-(4,5-Dihydrothiazol-2-yl)-3-(2-fluoro-4-(4-(4-(1,1,1,3,3,3-hexafluoro-2-hydroxypropan-2-yl)benzyl)piperazine-1-carbonyl)phenyl)urea MS (ESI) m/z 608.0 [M+H]$^+$ 24E: 1-(2-Fluoro-4-(4-(4-(1,1,1,3,3,3-hexafluoro-2-hydroxypropan-2-yl)benzyl)piperazine-1-carbonyl)phenyl)-3-(1,3,4-thiadiazol-2-yl)urea MS (ESI) m/z 607.0 [M+H]$^+$ 24F: 1-(2-Fluoro-4-(4-(4-(1,1,1,3,3,3-hexafluoro-2-hydroxypropan-2-yl)benzyl)piperazine-1-carbonyl)phenyl)-3-(thiazol-2-yl)urea MS (ESI) m/z 606.2 [M+H]$^+$ 24G: 1-(2-Fluoro-4-(4-(4-(1,1,1,3,3,3-hexafluoro-2-hydroxypropan-2-yl)benzyl)piperazine-1-carbonyl)phenyl)-3-(pyridin-4-yl)urea MS (ESI) m/z 600.3 [M+H]$^+$ 24H: 1-(2-Fluoro-4-(4-(4-(1,1,1,3,3,3-hexafluoro-2-hydroxypropan-2-yl)benzyl)piperazine-1-carbonyl)phenyl)-3-(oxazol-2-yl)urea MS (ESI) m/z 590.2 [M+H]$^+$ 24I: 1-(2-Fluoro-4-(4-(4-(1,1,1,3,3,3-hexafluoro-2-hydroxypropan-2-yl)benzyl)piperazine-1-carbonyl)phenyl)-3-(isoxazol-3-yl)urea MS (ESI) m/z 590.2 [M+H]$^+$ 24J: 1-(2-Fluoro-4-(4-(4-(1,1,1,3,3,3-hexafluoro-2-hydroxypropan-2-yl)benzyl)piperazine-1-carbonyl)phenyl)-3-(pyridazin-3-yl)urea

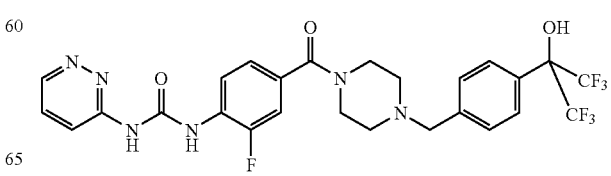

MS (ESI) m/z 601.2 [M+H]+ 24K: 1-(2-Fluoro-4-(4-(4-(1,1,1,3,3,3-hexafluoro-2-hydroxypropan-2-yl)benzyl)piperazine-1-carbonyl)phenyl)-3-(4-methylthiazol-2-yl)urea MS (ESI) m/z 620.2 [M+H]+

24L: 1-(5-Cyanothiazol-2-yl)-3-(2-fluoro-4-(4-(4-(1,1,1,3,3,3-hexafluoro-2-hydroxypropan-2-yl)benzyl)piperazine-1-carbonyl)phenyl)urea MS (ESI) m/z 631.5 [M+H]+

24M: 1-(2-Fluoro-4-(4-(4-(1,1,1,3,3,3-hexafluoro-2-hydroxypropan-2-yl)benzyl)piperazine-1-carbonyl)phenyl)-3-(isoxazol-4-yl)urea MS (ESI) m/z 590.3 [M+H]+

The following compound was prepared in a similar manner starting from (4-aminophenyl)-(4-(4-(1,1,1,3,3,3-hexafluoro-2-hydroxypropan-2-yl)benzyl)piperazin-1-yl)methanone:

24N: 1-(3-Fluoropyridin-4-yl)-3-(4-(4-(4-(1,1,1,3,3,3-hexafluoro-2-hydroxypropan-2-yl)benzyl)piperazine-1-carbonyl)phenyl)urea MS (ESI) m/z 600.3 [M+H]+

EXAMPLE 25

1-(2-Fluoro-4-(4-(4-(1,1,1,3,3,3-hexafluoro-2-hydroxypropan-2-yl)benzyl)piperazine-1-carbonyl)phenyl)-3-(pyridin-2-yl)urea

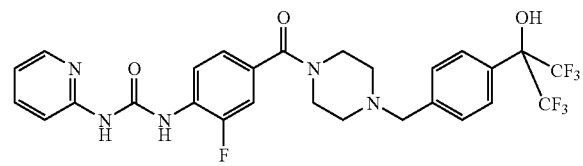 [SMILES: O=C(Nc1ccccn1)Nc1ccc(C(=O)N2CCN(Cc3ccc(C(O)(C(F)(F)F)C(F)(F)F)cc3)CC2)cc1F]

A: 1-(4-(4-(4-(2-(tert-Butyldimethylsilyloxy)-1,1,1,3,3,3-hexafluoropropan-2-yl)benzyl)piperazine-1-carbonyl)-2-fluorophenyl)-3-(pyridin-2-yl)urea

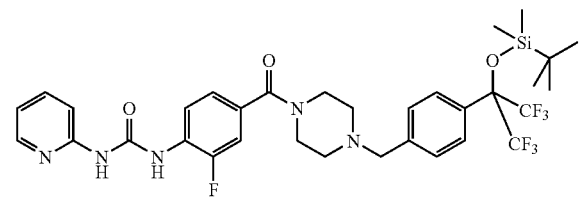 [SMILES: CC(C)(C)[Si](C)(C)OC(c1ccc(CN2CCN(C(=O)c3ccc(NC(=O)Nc4ccccn4)c(F)c3)CC2)cc1)(C(F)(F)F)C(F)(F)F]

(4-Amino-3-fluorophenyl)(4-(4-(2-(tert-butyldimethylsilyloxy)-1,1,1,3,3,3-hexa-fluoropropan-2-yl)benzyl)piperazin-1-yl)methanone (200 mg, 0.337 mmol) and 4-nitro-phenyl carbonochloridate (0.337 mmol, 0.068 g) were combined and stirred at room temperature for 1 hour in dichloromethane (1 mL). Pyridin-2-amine (0.674 mmol, 0.063 g) and triethylamine (0.674 mmol, 0.094 mL, 0.068 g) were added and the reaction mixture heated using microwave irradiation to 120° C. for 10 minutes. The reaction mixture was purified by silica column chromatography (eluant dichloromethane/methanol 0% to 2%) to afford the title compound (69 mg). MS (ESI) m/z 714.2 [M+H]+

B: 1-(2-Fluoro-4-(4-(4-(1,1,1,3,3,3-hexafluoro-2-hydroxypropan-2-yl)benzyl)piperazine-1-carbonyl)phenyl)-3-(pyridin-2-yl)urea 1-(4-(4-(4-(2-(tert-butyldimethylsilyloxy)-1,1,3,3,3-hexafluoropropan-2-yl)benzyl)piperazine-1-carbonyl)-2-fluorophenyl)-3-(pyridin-2-yl)urea (69 mg) and potassium fluoride (50% in celite) (0.961 mmol, 0.112 g) were combined and heated to reflux for 48 hours in tetrahydrofuran (5 mL). The solid was filtered off and the filtrate concentrated under reduced pressure. The resulting residue was purified by silica column chromatography (eluant dichloromethane/methanol 0% to 4%) to afford the title compound (26 mg). MS (ESI) m/z 600.2 [M+H]+

The following compounds were prepared in a similar manner:

25B: 1-(2-Fluoro-4-(4-(4-(1,1,1,3,3,3-hexafluoro-2-hydroxypropan-2-yl)benzyl)piperazine-1-carbonyl)phenyl)-3-(3-methylisoxazol-5-yl)urea MS (ESI) m/z 604.5 [M+H]+

25C: 1-(2-Fluoro-4-(4-(4-(1,1,1,3,3,3-hexafluoro-2-hydroxypropan-2-yl)benzyl)piperazine-1-carbonyl)phenyl)-3-(3-methyl-1,2,4-oxadiazol-5-yl)urea MS (ESI) m/z 605.2 [M+H]+

25D: 1-(2-Fluoro-4-(4-(4-(1,1,1,3,3,3-hexafluoro-2-hydroxypropan-2-yl)benzyl)piperazine-1-carbonyl)phenyl)-3-(pyridin-3-yl)urea MS (ESI) m/z 600.0 [M+H]+

EXAMPLE 26

1-(2-Fluoro-4-(4-(4-(1,1,1,3,3,3-hexafluoro-2-hydroxypropan-2-yl)benzyl)piperazine-1-carbonyl)phenyl)-3-(Pyrimidin-4-yl)urea

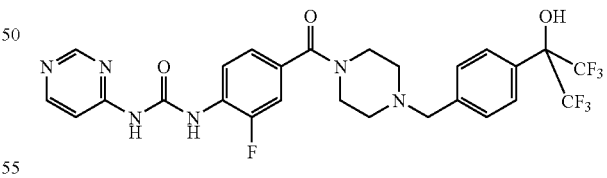

Pyrimidin-4-amine (0.337 mmol, 0.032 g) and N-ethyl-N-isopropylpropan-2-amine (1.145 mmol, 0.189 mL, 0.148 g) were stirred in dichloromethane (2 mL) at room temperature. Triphosgene (0.125 mmol, 0.037 g) was added and the reaction stirred for 30 minutes. (4-Amino-3-fluorophenyl)(4-(4-(2-(tert-butyldimethylsilyloxy)-1,1,1,3,3,3-hexafluoropropan-2-yl)benzyl)piperazin-1-yl)methanone (0.168 mmol, 0.1 g) was added and the reaction heated to 120° C. in the microwave for 10 minutes. The reaction mixture was washed with water and concentrated under reduced pressure. The resulting residue was purified by silica column chromatography (eluant dichloromethane/methanol 0% to 5%) to afford the title compound (63 mg). MS (ESI) m/z 715.7 [M+H]+

B: 1-(2-Fluoro-4-(4-(4-(1,1,1,3,3,3-hexafluoro-2-hydroxypropan-2-yl)benzyl)piperazine-1-carbonyl)phenyl)-3-(pyrimidin-4-yl)urea 1-(4-(4-(4-(2-(tert-butyldimethylsilyloxy)-1,1,1,3,3,3-hexafluoropropan-2-yl)benzyl)-piperazine-1-carbonyl)-2-fluorophenyl)-3-(pyrimidin-4-yl)urea (0.088 mmol, 0.0627 g) and potassium fluoride (50% on celite) (0.877 mmol, 0.102 g) were combined and heated to reflux in tetrahydrofuran (5 mL) overnight. The reaction mixture was filtered and the filtrate concentrated under reduced pressure. The resulting residue was purified by silica column chromatography (eluant dichloromethane/methanol 0% to 5%) to afford the title compound (8 mg). MS (ESI) m/z 601.3 [M+H]+

The following compound was prepared in a similar manner:

26B: 1-(2-Fluoro-4-(4-(4-(1,1,1,3,3,3-hexafluoro-2-hydroxypropan-2-yl)benzyl)piperazine-1-carbonyl)phenyl)-3-(Pyrazin-2-yl)urea MS (ESI) m/z 601.3 [M+H]+

EXAMPLE 27

1-(2-Cyano-2-methylpropyl)-3-(2-fluoro-4-(4-(4-(1,1,1,3,3,3-hexafluoro-2-hydroxypropan-2-yl)benzyl)piperazine-1-carbonyl)phenyl)urea hydrochloride

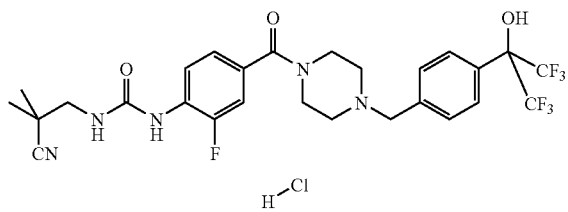 [SMILES: CC(C)(C#N)CNC(=O)Nc1ccc(C(=O)N2CCN(Cc3ccc(C(O)(C(F)(F)F)C(F)(F)F)cc3)CC2)cc1F ; Cl]

A: (4-Amino-3-fluorophenyl)(4-benzylpiperazin-1-yl)methanone

4-Amino-3-fluorobenzoic acid (28.4 mmol, 4.40 g), 1-benzylpiperazine (28.4 mmol, 4.93 mL, 5 g) and triethylamine (85 mmol, 11.86 mL, 8.61 g) were stirred in dichloromethane at room temperature. 1-Propanephosphonic acid cyclic anhydride (42.6 mmol, 25.2 mL, 27.1 g, 50% solution in ethyl acetate) was added and the reaction mixture stirred at room temperature for 1 hour. The reaction mixture was washed with saturated sodium bicarbonate solution and concentrated under reduced pressure to afford the title compound (7.51 g). MS (ESI) m/z 314.1 [M+H]+

B: 1-(4-(4-Benzylpiperazine-1-carbonyl)-2-fluorophenyl)-3-(2-cyano-2-methylpropyl)urea (4-Amino-3-fluorophenyl)(4-benzylpiperazin-1-yl)methanone and Hunig's base (32.5 mmol, 5.38 mL, 4.21 g) were stirred in dichloromethane. Triphosgene (3.54 mmol, 1.051 g) was added and the reaction stirred at ambient temperature for 30 minutes. 3-Amino-2,2-dimethylpropanenitrile hydrochloride (9.57 mmol, 1.289 g) was added and the reaction stirred for a further 30 minutes. The reaction mixture was washed with water and the organic layer concentrated under reduced pressure. The resulting residue was purified by silica column chromatography (eluant dichloromethane/methanol 0% to 5%) to afford the title compound (1.809 g). MS (ESI) m/z 438.1 [M+H]+

C: 1-(2-Cyano-2-methylpropyl)-3-(2-fluoro-4-(piperazine-1-carbonyl)phenyl)urea 1-(4-(4-Benzylpiperazine-1-carbonyl)-2-fluorophenyl)-3-(2-cyano-2-methylpropyl)urea (4.12 mmol, 1.802 g) and 10% palladium on carbon (0.824 mmol, 0.877 g) were stirred in ethanol (40 mL) under a hydrogen atmosphere at 5 bar at room temperature overnight with a few drops of 5M hydrochloric acid. The catalyst was filtered off and the filtrate concentrated under reduced pressure to afford the title compound (1.033 g). MS (ESI) m/z 348.3 [M+H]+

D: 1-(2-Cyano-2-methylpropyl)-3-(2-fluoro-4-(4-(4-(1,1,1,3,3,3-hexafluoro-2-hydroxypropan-2-yl)benzyl)piperazine-1-carbonyl)phenyl)urea hydrochloride 1-(2-Cyano-2-methylpropyl)-3-(2-fluoro-4-(piperazine-1-carbonyl)phenyl)urea (2.96 mmol, 1.03 g), 2-(4-(bromomethyl)phenyl)-1,1,1,3,3,3-hexafluoropropan-2-ol (2.96 mmol, 0.999 g) and potassium carbonate (5.93 mmol, 0.820 g) were stirred overnight at room temperature in acetonitrile (50 mL). The solvent was removed at reduced pressure and the resulting residue purified by silica column chromatography (eluant dichloromethane/methanol 0% to 5%). The resulting residue was then treated with 2M hydrochloric acid in ether to afford the title compound (151 mg).

MS (ESI) m/z 604.7 [M+H]+

EXAMPLE 28

1-(2-Fluoro-4-{4-[4-(2,2,2-trifluoro-1-hydroxy-1-trifluoromethyl-ethyl)-benzyl]-piperazine-1-carbonyl}-phenyl)-3-(1-oxo-tetrahydro-thiopyran-4-yl)-urea

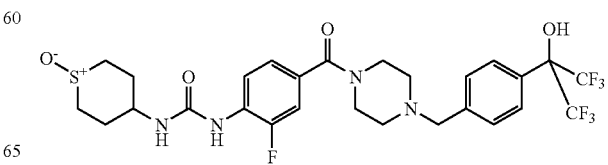

A: 1-[4-(4-{4-[1-(tert-Butyl-dimethyl-silanyloxy)-2,2,2-trifluoro-1-trifluoromethyl-ethyl]-benzyl}-piperazine-1-carbonyl)-2-fluoro-phenyl]-3-(1-oxo-tetrahydro-thiopyran-4-yl)-urea

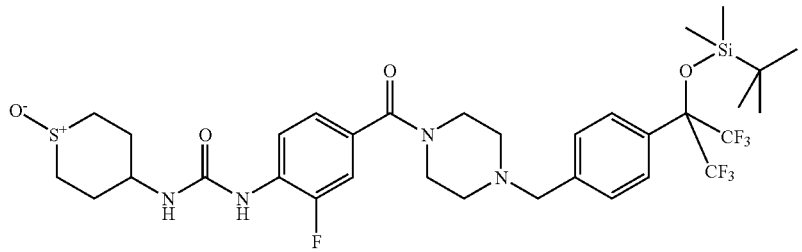 [SMILES: CC(C)(C)[Si](C)(C)OC(c1ccc(CN2CCN(C(=O)c3ccc(NC(=O)NC4CC[S+]([O-])CC4)c(F)c3)CC2)cc1)(C(F)(F)F)C(F)(F)F]

Step) 1: A solution of (4-amino-3-fluorophenyl)(4-(4-(2-(tert-butyldimethylsilyloxy)-1,1,1,3,3,3-hexafluoropropan-2-yl)benzyl)piperazin-1-yl)methanone (4.21 mmol, 2.5 g) and 4-nitrophenyl carbonochloridate (4.21 mmol, 0.849 g) in dichloromethane (20 mL) were stirred at ambient temperature for 30 minutes. Tetrahydro-2H-thiopyran-4-amine (8.42 mmol, 0.987 g) and triethylamine (14.39 mmol, 2 mL, 1.456 g) were added and the reaction stirred overnight. The reaction mixture was diluted with dichloromethane (30 mL) and saturated sodium hydrogen carbonate solution (50 mL) and the layers separated. The organic layer was dried over magnesium sulfate and concentrated under vacuum. The residue was dissolved in dichloromethane and purified by column chromatography (eluent dichloromethane/methanol 2-8%) to afford the intermediate 1-(4-(4-(4-(2-(tert-butyldimethylsilyloxy)-1,1,3,3,3-hexafluoropropan-2-yl)benzyl)piperazine-1-carbonyl)-2-fluorophenyl)-3-(tetrahydro-2H-thiopyran-4-yl)urea (1.8 g).

Step 2: To an ice-cooled solution of 1-(4-(4-(4-(2-(tert-butyldimethylsilyloxy)-1,1,1,3,3,3-hexafluoropropan-2-yl)benzyl)piperazine-1-carbonyl)-2-fluorophenyl)-3-(tetrahydro-2H-thiopyran-4-yl)urea (0.679 mmol, 500 mg) in dichloromethane (5 mL) was added 3-chloroperoxybenzoic acid (0.746 mmol, 167 mg). The resulting mixture was stirred at ambient temperature for 1 hour before the addition of 1 M hydrochloric acid (10 mL). The organic layer was separated, dried over magnesium sulphate and concentrated under vacuum. The residue was dissolved in dichloromethane and purified by column chromatography (eluent dichloromethane/methanol 2-10%) to afford the title compound (130 mg). MS (ESI) m/z 753.3 [M+H]$^+$ B: 1-(2-Fluoro-4-{4-[4-(2,2,2-trifluoro-1-hydroxy-1-trifluoromethyl-ethyl)-benzyl]-piperazine-1-carbonyl}-phenyl)-3-(1-oxo-tetrahydro-thiopyran-4-yl)-urea To a stirring solution of 1-[4-(4-{4-[1-(tert-butyl-dimethyl-silanyloxy)-2,2,2-trifluoro-1-trifluoromethyl-ethyl]-benzyl}-piperazine-1-carbonyl)-2-fluoro-phenyl]-3-(1-oxo-tetrahydro-thiopyran-4-yl)-urea (0.173 mmol, 130 mg) in tetrahydrofuran (1 mL) was added potassium fluoride (50% wt on celite) (1.727 mmol, 201 mg). The resulting suspension was heated to 80° C. for 48 hours. The reaction mixture was filtered through celite and purified by SCX chromatography to afford the title compound (20 mg). MS (ESI) m/z 639.0 [M+H]$^+$ The following compound was prepared in a similar manner from tetrahydrothiophen-3-amine:

28B: 1-(2-Fluoro-4-{4-[4-(2,2,2-trifluoro-1-hydroxy-1-trifluoromethyl-ethyl)-benzyl]-piperazine-1-carbonyl}-phenyl)-3-(1-oxo-tetrahydro-thiophen-3-yl)-urea MS (ESI) m/z 625.0 [M+H]$^+$

EXAMPLE 29

(R)-tert-Butyl 3-(3-(2-fluoro-4-(4-(4-(1,1,1,3,3,3-hexafluoro-2-hydroxypropan-2-yl)benzyl)piperazine-1-carbonyl)phenyl)ureido)pyrrolidine-1-carboxylate

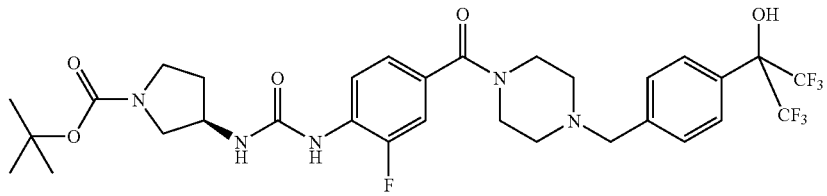 [SMILES: CC(C)(C)OC(=O)N1CC[C@@H](NC(=O)Nc2ccc(C(=O)N3CCN(Cc4ccc(C(O)(C(F)(F)F)C(F)(F)F)cc4)CC3)cc2F)C1]

A: (R)-tert-Butyl 3-(3-(4-(4-(4-(2-(tert-butyldimethylsilyloxy)-1,1,1,3,3,3-hexafluoropropan-2-yl)benzyl)piperazine-1-carbonyl)-2-fluorophenyl)ureido)pyrrolidine-1-carboxylate

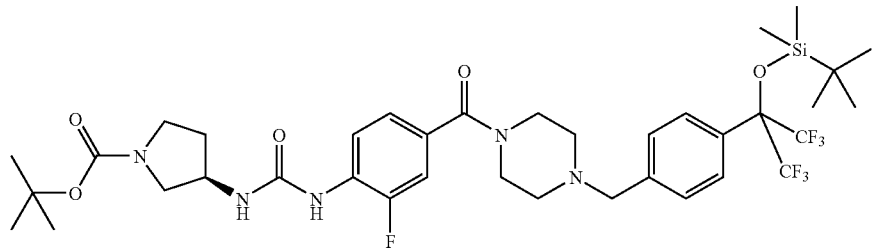 [SMILES: CC(C)(C)OC(=O)N1CC[C@@H](NC(=O)Nc2ccc(C(=O)N3CCN(Cc4ccc(C(O[Si](C)(C)C(C)(C)C)(C(F)(F)F)C(F)(F)F)cc4)CC3)cc2F)C1]

A solution of (4-amino-3-fluorophenyl)(4-(4-(2-(tert-butyldimethylsilyloxy)-1,1,1,3,3,3-hexafluoropropan-2-yl)benzyl)piperazin-1-yl)methanone (0.674 mmol, 400 mg) and 4-nitrophenyl carbonochloridate (0.674 mmol, 136 mg) in dichloromethane (10 mL) was stirred at room temperature for 30 minutes. (R)-tert-Butyl 3-aminopyrrolidine-1-carboxylate (2.021 mmol, 0.353 mL, 376 mg) was added and the reaction stirred at room temperature overnight. The reaction mixture was diluted with dichloromethane (10 mL) and washed with saturated aqueous sodium hydrogen carbonate solution (10 mL). The organic phase was concentrated and the resulting residue was purified by column chromatography on silica gel (eluting with dichloromethane—5% methanol/95% dichloromethane gradient) to afford the title compound (300 mg).

MS (ESI) m/z 806.7 [M+H]⁺

B: (R)-tert-Butyl 3-(3-(2-fluoro-4-(4-(4-(1,1,1,3,3,3-hexafluoro-2-hydroxypropan-2-yl)benzyl)piperazine-1-carbonyl)phenyl)ureido)pyrrolidine-1-carboxylate To a stirring solution of (R)-tert-butyl 3-(3-(4-(4-(4-(2-(tert-butyldimethylsilyloxy)-1,1,1,3,3,3-hexafluoropropan-2-yl)benzyl)piperazine-1-carbonyl)-2-fluorophenyl)ureido)pyrrolidine-1-carboxylate (0.372 mmol, 300 mg) in tetrahydrofuran (10 mL) was added potassium fluoride (50% weight on celite) (3.72 mmol, 433 mg). The resulting suspension was heated to 80° C. for 16 hours. The reaction mixture was filtered through celite and concentrated under vacuum. The resulting residue was purified by column chromatography on silica gel (eluting with dichloromethane—5% methanol/95% dichloromethane gradient) to afford the title compound (210 mg). MS (ESI) m/z 692.3 [M+H]⁺

EXAMPLE 30

(R)-1-(1-(2-Cyclopropylacetyl)pyrrolidin-3-yl)-3-(2-fluoro-4-(4-(4-(1,1,1,3,3,3-hexafluoro-2-hydroxypropan-2-yl)benzyl)piperazine-1-carbonyl)phenyl)urea

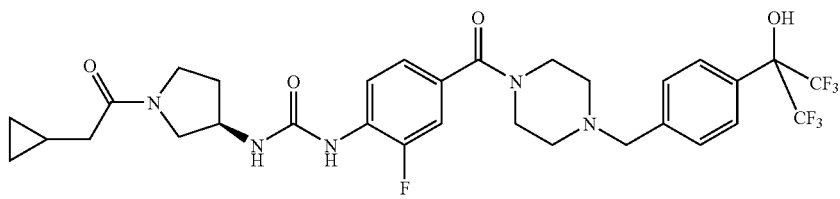 [SMILES: O=C(Nc1ccc(C(=O)N2CCN(Cc3ccc(C(O)(C(F)(F)F)C(F)(F)F)cc3)CC2)cc1F)N[C@@H]1CCN(C(=O)CC2CC2)C1]

A: (R)-1-(2-Fluoro-4-(4-(4-(1,1,1,3,3,3-hexafluoro-2-hydroxypropan-2-yl)benzyl)piperazine-1-carbonyl)phenyl)-3-(pyrrolidin-3-yl)urea To a stirring solution of (R)-tert-butyl 3-(3-(2-fluoro-4-(4-(4-(1,1,1,3,3,3-hexafluoro-2-hydroxypropan-2-yl)benzyl)piperazine-1-carbonyl)phenyl)ureido)pyrrolidine-1-carboxylate (0.289 mmol, 200 mg) in dichloromethane (5 mL) was added trifluoroacetic acid (7.23 mmol, 824 mg) and the mixture allowed to stir at room temperature for 5 hours. The reaction mixture was purified by strong cation exchange column chromatography to afford the title compound (146 mg). MS (ESI) m/z 592.3 [M+H]⁺

B: (R)-1-(1-(2-Cyclopropylacetyl)pyrrolidin-3-yl)-3-(2-fluoro-4-(4-(4-(1,1,1,3,3,3-hexafluoro-2-hydroxypropan-2-yl)benzyl)piperazine-1-carbonyl)phenyl)urea To a stirring solution of (R)-1-(2-fluoro-4-(4-(4-(1,1,1,3,3,3-hexafluoro-2-hydroxypropan-2-yl)benzyl)piperazine-1- carbonyl)phenyl)-3-(pyrrolidin-3-yl)urea (0.123 mmol, 73 mg), 2-cyclopropylacetic acid (0.123 mmol, 12.4 mg) and triethylamine (0.370 mmol, 35.5 mg) in dichloromethane (2 mL) was added 1-propanephosphonic acid cyclic anhydride (0.370 mmol, 118 mg; 50% solution in ethyl acetate). The reaction mixture was stirred at room temperature for 1 hour. The reaction mixture was diluted with dichloromethane (2 mL) and washed with saturated aqueous sodium hydrogen carbonate solution (3 mL). The organic phase was concentrated and the resulting residue was purified by HPLC and then treated with strong cation exchange column chromatography to afford the title compound (28 mg). MS (ESI) m/z 674.3 [M+H]$^+$

EXAMPLE 31

1-(4-(4-(4-(1,1,1,3,3,3-Hexafluoro-2-hydroxypropan-2-yl)benzyl)piperazine-1-carbonyl)-2-methoxyphenyl)-3-(pyridin-4-yl)urea

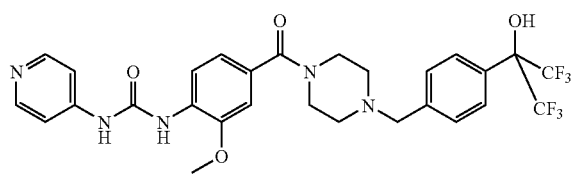 [SMILES: COc1cc(C(=O)N2CCN(Cc3ccc(C(O)(C(F)(F)F)C(F)(F)F)cc3)CC2)ccc1NC(=O)Nc1ccncc1]

A: tert-Butyl 4-(4-(1,1,1,3,3,3-hexafluoro-2-hydroxypropan-2-yl)benzyl)piperazine-1-carboxylate

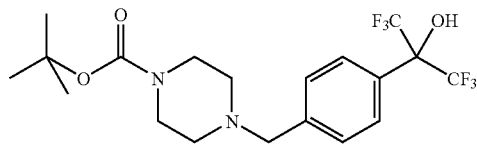 [SMILES: CC(C)(C)OC(=O)N1CCN(Cc2ccc(C(O)(C(F)(F)F)C(F)(F)F)cc2)CC1]

2-(4-(Bromomethyl)phenyl)-1,1,1,3,3,3-hexafluoropropan-2-ol (14.83 mmol, 5 g), tert-butyl piperazine-1-carboxylate (14.83 mmol, 2.76 g) and potassium carbonate (44.5 mmol, 6.15 g) were combined and stirred at room temperature overnight in acetonitrile (50 mL). The reaction mixture was filtered and the solvent removed at reduced pressure. The residue was taken up in ethyl acetate and washed with saturated sodium bicarbonate solution. The organic layer was dried over magnesium sulphate and concentrated under vacuum to afford the title compound (7.12 g).
MS (ESI) m/z 442.9 [M+H]$^+$ B: 1,1,1,3,3,3-Hexafluoro-2-(4-(piperazin-1-ylmethyl)phenyl)propan-2-ol To a solution of tert-butyl 4-(4-(1,1,1,3,3,3-hexafluoro-2-hydroxypropan-2-yl)benzyl)piperazine-1-carboxylate (16.09 mmol, 7.12 g) in dichloromethane (30 mL) was added trifluoroacetic acid (5 mL) and the reaction stirred at room temperature for 2 hours. The reaction mixture was concentrated under vacuum and purified by SCX chromatography to afford the title compound (3.5 g). MS (ESI) m/z 343.1 [M+H]$^+$ C: (4-Amino-3-methoxyphenyl)(4-(4-(1,1,1,3,3,3-hexafluoro-2-hydroxypropan-2-yl)benzyl)piperazin-1-yl)methanone

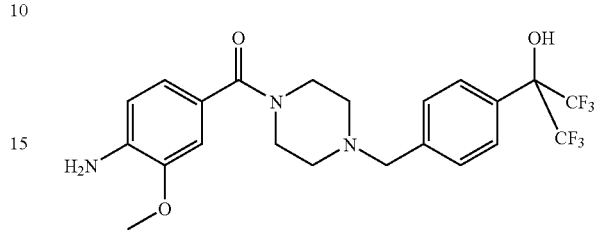

4-Amino-3-methoxybenzoic acid (2.045 mmol, 0.342 g), 1,1,1,3,3,3-hexafluoro-2-(4-(piperazin-1-ylmethyl)phenyl)propan-2-ol (2.045 mmol, 0.700 g) and triethylamine (6.14 mmol, 0.853 mL, 0.621 g) were combined and stirred at room temperature in dichloro-methane (5 mL). 1-Propanephosphonic acid cyclic anhydride (3.07 mmol, 1.826 mL, 1.952 g; 50% solution in ethyl acetate) was added and the reaction stirred for 1 hour. The reaction mixture was diluted with dichloromethane and saturated sodium hydrogen carbonate solution and the layers separated. The organic layer was dried over magnesium sulfate and concentrated under vacuum to afford the title compound (1.13 g). MS (ESI) m/z 492.1 [M+H]$^+$ D: 1-(4-(4-(4-(1,1,1,3,3,3-Hexafluoro-2-hydroxypropan-2-yl)benzyl)piperazine-1-carbonyl)-2-methoxyphenyl)-3-(pyridin-4-yl)urea (4-Amino-3-methoxyphenyl)(4-(4-(1,1,1,3,3,3-hexafluoro-2-hydroxypropan-2-yl)benzyl)piperazin-1-yl)methanone (0.407 mmol, 200 mg) and phenyl pyridin-4-ylcarbamate (0.610 mmol, 131 mg) were combined in dioxane (2 mL) and heated to 80° C. overnight in a reactivial. The reaction mixture was concentrated under vacuum and the residue was purified by column chromatography (dichloromethane—4% methanol/dichloromethane) to afford title compound (12.2 mg). MS (ESI) m/z 612.3 [M+H]$^+$

EXAMPLE 32

1-(4-(4-(4-(1,1,1,3,3,3-Hexafluoro-2-hydroxypropan-2-yl)benzyl)piperazine-1-carbonyl)-2-methoxyphenyl)-3-((1 r,4r)-4-hydroxycyclohexyl)urea

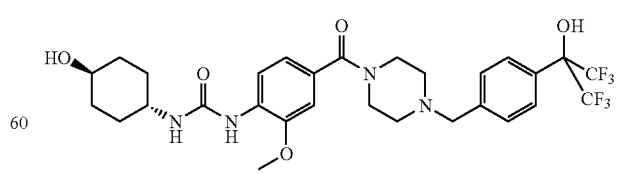

(4-Amino-3-methoxyphenyl)(4-(4-(1,1,1,3,3,3-hexafluoro-2-hydroxypropan-2-yl)benzyl)piperazin-1-yl)methanone (0.509 mmol, 250 mg) and 4-nitrophenyl carbonochloridate (0.509 mmol, 103 mg) in dichlormethane (1 mL)

were stirred at room temperature for 30 minutes. (1R,4R)-4-Aminocyclohexanol (1.017 mmol, 117 mg) and triethylamine (1.526 mmol, 0.213 mL, 154 mg) were added and the reaction was stirred at room temperature overnight. The reaction mixture was diluted with dichloromethane and saturated sodium hydrogen carbonate solution, and filtered through a hydrophobic frit. The organic layer was concentrated, and the residue taken up in dichloromethane and purified by column chromatography (2-8% methanol in dichloromethane) to afford title compound (77.6 mg) as a white solid. MS (ESI) m/z 633.0 [M+H]$^+$ The following compound was prepared in a similar manner:

32B: 1-(4-(4-(4-(1,1,1,3,3,3-Hexafluoro-2-hydroxypropan-2-yl)benzyl)piperazine-1-carbonyl)-2-methoxyphenyl)-3-(pyridazin-4-yl)urea

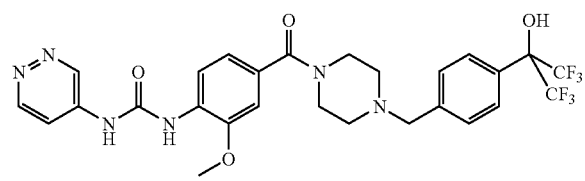 [SMILES: COc1cc(C(=O)N2CCN(Cc3ccc(C(O)(C(F)(F)F)C(F)(F)F)cc3)CC2)ccc1NC(=O)Nc1ccnnc1]

MS (ESI) m/z 613.3 [M+H]$^+$

EXAMPLE 33

1-(2,6-Difluoro-4-(4-(4-(1,1,1,3,3,3-hexafluoro-2-hydroxypropan-2-yl)benzyl)piperazine-1-carbonyl)phenyl)-3-(pyridin-4-yl)urea

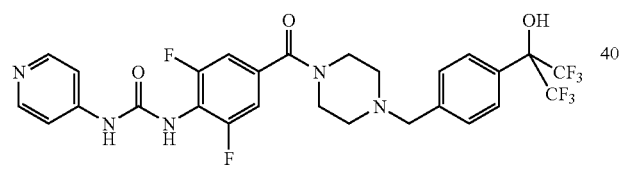

A: (4-Amino-3,5-difluorophenyl)(4-(4-(1,1,1,3,3,3-hexafluoro-2-hydroxypropan-2-yl)benzyl)piperazin-1-yl)methanone

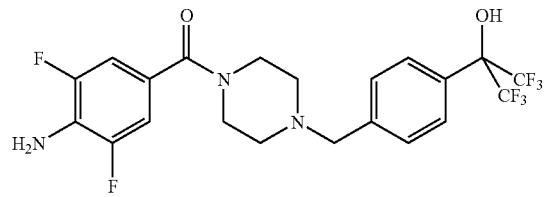 [SMILES: Nc1c(F)cc(C(=O)N2CCN(Cc3ccc(C(O)(C(F)(F)F)C(F)(F)F)cc3)CC2)cc1F]

4-Amino-3,5-difluorobenzoic acid (1.899 mmol, 329 mg), 1,1,1,3,3,3-hexafluoro-2-(4-(piperazin-1-ylmethyl)phenyl)propan-2-ol (1.899 mmol, 650 mg) and triethylamine (5.70 mmol, 0.792 mL, 576 mg) were combined and stirred at room temperature in dichloromethane (5 mL). 1-Propanephosphonic acid cyclic anhydride (2.85 mmol, 1.696 mL, 1813 mg; 50% solution in ethyl acetate) was added and the reaction stirred for 2 hours. Saturated sodium hydrogen carbonate solution was added to the reaction mixture and the layers separated. The organic layer was dried over magnesium sulfate and concentrated under vacuum to afford the title compound (340 mg) as a pale pink solid. MS (ESI) m/z 498.7 [M+H]$^+$ B: 1-(2,6-Difluoro-4-(4-(4-(1,1,1,3,3,3-hexafluoro-2-hydroxypropan-2-yl)benzyl)piperazine-1-carbonyl)phenyl)-3-(pyridin-4-yl)urea (4-Amino-3,5-difluorophenyl)(4-(4-(1,1,1,3,3,3-hexafluoro-2-hydroxypropan-2-yl)benzyl)piperazin-1-yl)methanone (0.342 mmol, 170 mg) and phenyl pyridin-4-ylcarbamate (0.513 mmol, 110 mg) were combined in dioxane (2 mL) and heated to 80° C. overnight in a reactivial. The reaction mixture was concentrated under vacuum and the residue was purified by column chromatography (dichloromethane—4% methanol/dichloromethane) to afford title compound (45 mg). MS (ESI) m/z 618.3 [M+H]$^+$

EXAMPLE 34

1-(4-(4-(4-(1,1,1,3,3,3-Hexafluoro-2-hydroxypropan-2-yl)benzyl)piperazine-1-carbonyl)-2-(trifluoromethoxy)phenyl)-3-(pyridin-4-yl)urea

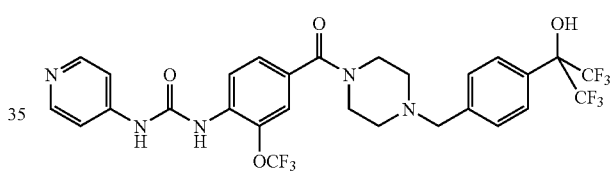

A: (4-Amino-3-(trifluoromethoxy)phenyl)(4-(4-(1,1,1,3,3,3-hexafluoro-2-hydroxypropan-2-yl)benzyl)piperazin-1-yl)methanone

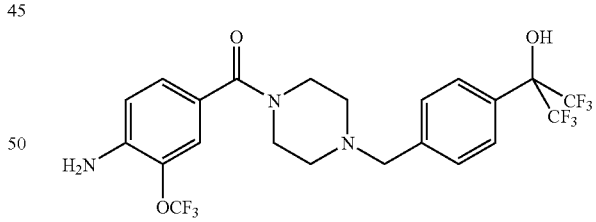

4-Amino-3-(trifluoromethoxy)benzoic acid (2.045 mmol, 0.452 g), 1,1,1,3,3,3-hexafluoro-2-(4-(piperazin-1-ylmethyl)phenyl)propan-2-ol (2.045 mmol, 0.700 g) and triethylamine (6.14 mmol, 0.853 mL, 0,621 g) were combined and stirred at room temperature in dichloromethane (5 mL). 1-Propanephosphonic acid cyclic anhydride (3.07 mmol, 1.826 mL, 1.952 g; 50% solution in ethyl acetate) was added and the reaction stirred for 1 hour. The reaction mixture was diluted with dichloromethane and saturated sodium hydrogen carbonate solution and the layers separated. The organic layer was dried over magnesium sulfate and concentrated under vacuum to afford the title compound (1.26 g). MS (ESI) m/z 546.5 [M+H]$^+$ B: 1-(4-(4-(4-(1,1,1,3,3,3-Hexafluoro-2-hydroxypropan-2-yl)benzyl)piperazine-1-carbonyl)-2-(trifluoromethoxy)phenyl)-3-(pyridin-4-yl)urea (4-Amino-3-(trifluoromethoxy)phenyl)(4-(4-(1,1,1,3,3,3-hexafluoro-2-hydroxypropan-2-yl)benzyl)piperazin-1-yl)methanone (0.367 mmol, 200 mg) and phenyl pyridin-4-ylcarbamate (0.550 mmol, 118 mg) were combined in dioxane (2 mL) and heated to 80° C. overnight in a reactivial. The reaction mixture was concentrated under vacuum and the residue was purified by column chromatography (dichloromethane—4% methanol/dichloromethane) to afford title compound (11.7 mg). MS (ESI) m/z 666.3 [M+H]$^+$

EXAMPLE 35

1-(5-Bromo-2-fluoro-4-(4-(4-(1,1,1,3,3,3-hexafluoro-2-hydroxypropan-2-yl)benzyl)piperazine-1-carbonyl)phenyl)-3-(pyridin-4-yl)urea

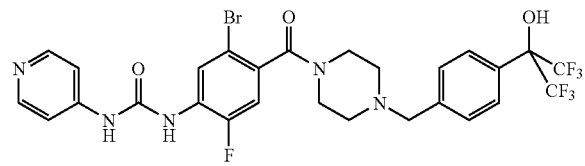 [SMILES: O=C(Nc1ccncc1)Nc1cc(Br)c(C(=O)N2CCN(Cc3ccc(C(O)(C(F)(F)F)C(F)(F)F)cc3)CC2)cc1F]

A: Methyl 4-(benzylamino)-2-bromo-5-fluorobenzoate

Step 1: A solution of 2-bromo-4,5-difluorobenzoic acid (5 g, 21.10 mmol) in methanol was treated with 1 mL of 10M hydrochloric acid and heated to reflux for 72 hours. The reaction mixture was evaporated under vacuum, dissolved in ether and washed with water before drying (magnesium sulfate) and evaporation to a give the intermediate methyl 2-bromo-4,5-difluorobenzoate (5 g) as a colourless oil.

Step 2: A solution of the intermediate methyl 2-bromo-4,5-difluorobenzoate (4.4 g, 17.53 mmol) and benzylamine (2.066 g, 2.108 mL, 19.28 mmol) in N,N-dimethylsulfoxide was treated with dibasic potassium phosphate (12.21 g, 70.1 mmol) and heated to 75° C. for 18 hours in an open tube. The reaction mixture was then diluted with of ethyl acetate (200 mL), washed with of water (4×150 mL) and saturated brine before drying (sodium sulfate) and evaporation to yield the title compound (5.3 g). $^1$H NMR (CDCl$_3$, 400 MHz): δ 3.86 (2H, s), 4.40 (2H, d), 4.69 (1H, br s), 6.91 (1H, d), 7.35 (5H, m), 7.63 (1H, d)

B: Methyl 4-amino-2-bromo-5-fluorobenzoate

A suspension of the methyl 4-(benzylamino)-2-bromo-5-fluorobenzoate (2.4 g, 7.10 mmol) in acetic acid was treated with 10% palladium on charcoal (250 mg) and stirred at room temperature under 2 bar hydrogen for 18 hours. The reaction mixture was then diluted with methanol, filtered through celite and evaporated to low volume. The residue was suspended in water (50 mL) and basified with 5% sodium carbonate solution then was extracted with ethyl acetate (2×). The combined organic phases were dried (sodium sulfate) and evaporated to a sandy solid. This crude solid was dissolved in the methanol and passed down an SCX cartridge. Evaporation of the methanol eluents gave the title compound (1.3 g).

$^1$H NMR (CDCl$_3$, 400 MHz): δ 3.87 (3H, s), 4.11 (2H, br s), 7.02 (1H, d), 7.63 (1H, d)

C: 4-Amino-2-bromo-5-fluorobenzoic acid

A solution of the intermediate methyl 4-amino-2-bromo-5-fluorobenzoate (5.24 mmol, 1.3 g) in tetrahydrofuran (15 mL) was treated with a solution of lithium hydroxide (15.72 mmol, 0.66 g) in water (15 mL) and stirred at 60° C. for 4 hours. The reaction mixture was then cooled to room temperature, taken to ~pH 5 with dilute hydrochloric acid and concentrated under vacuum. The residue was dissolved in tetrahydrofuran and purified by column chromatography (9:1 dichloromethane/methanol) to give the title compound (1.1 g). $^1$H NMR ((CD$_3$)$_2$SO, 400 MHz): δ6.11 (2H, s), 7.02 (1H, d), 7.52 (1H, d)

D: (4-Amino-2-bromo-5-fluorophenyl)(4-(4-(1,1,1,3,3,3-hexafluoro-2-hydroxypropan-2-yl)benzyl)piperazin-1-yl)methanone 4-Amino-2-bromo-5-fluorobenzoic acid (2.045 mmol, 0.479 g), 1,1,1,3,3,3-hexafluoro-2-(4-(piperazin-1-ylmethyl)phenyl)propan-2-ol (2.045 mmol, 0.7 g) and triethylamine (6.14 mmol, 0.853 mL, 0.621 g) were combined and stirred at room temperature in dichloromethane (5 mL). 1-Propanephosphonic acid cyclic anhydride (3.07 mmol, 1.826 mL, 1.952 g; 50% solution in ethyl acetate) was added and the reaction stirred for 1 hour. The reaction mixture was diluted with dichloromethane and saturated sodium hydrogen carbonate solution and the layers separated. The organic layer was dried over magnesium sulfate and concentrated under vacuum to afford the title compound (660 mg). MS (ESI) m/z 558.5 [M+H]$^+$ E: 1-(5-Bromo-2-fluoro-4-(4-(4-(1,1,1,3,3,3-hexafluoro-2-hydroxypropan-2-yl)benzyl)piperazine-1-carbonyl)phenyl)-3-(pyridin-4-yl)urea (4-Amino-2-bromo-5-fluorophenyl)(4-(4-(1,1,1,3,3,3-hexafluoro-2-hydroxypropan-2-yl)benzyl)piperazin-1-yl)methanone (0.358 mmol, 200 mg) and phenyl pyridin-4-ylcarbamate (0.537 mmol, 115 mg) were combined in dioxane (2 mL) and heated to 80° C. overnight in a reactivial. The reaction mixture was concentrated under vacuum and the residue was purified by column chromatography (dichloromethane—4% methanol/dichloromethane) to afford title compound (13 mg). MS (ESI) m/z 679.3 [M+H]$^+$

EXAMPLE 36

4-(4-(4-(1,1,1,3,3,3-Hexafluoro-2-hydroxypropan-2-yl)benzyl)piperazine-1-carbonyl)phenyl cyclopropylmethylcarbamate

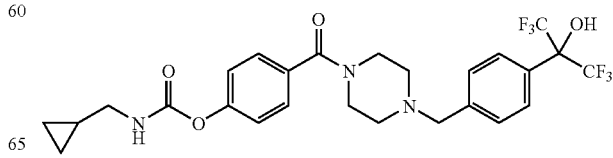

A: (4-(4-(1,1,1,3,3,3-Hexafluoro-2-hydroxypropan-2-yl)benzyl)piperazin-1-yl)(4-hydroxyphenyl)methanone 4-Hydroxybenzoic acid (2.045 mmol, 0.282 g), 1,1,1,3,3,3-hexafluoro-2-(4-(piperazin-1-ylmethyl)phenyl)propan-2-ol (2.045 mmol, 0.7 g) and triethylamine (6.14 mmol, 0.853 mL, 0.621 g) were combined and stirred at room temperature in dichloromethane (5 mL). 1-Propanephosphonic acid cyclic anhydride (3.07 mmol, 1.826 mL, 1.952 g; 50% solution in ethyl acetate) was added and the reaction stirred for 2 hours. The reaction mixture was washed with saturated sodium bicarbonate solution and the organic layer dried over magnesium sulphate and concentrated under vacuum. The residue was dissolved in dichloromethane with a few drops of methanol and purified by column chromatography (dichloromethane—6% methanol in dichloromethane) to afford the title compound (90 mg). MS (ESI) m/z 463.0 [M+H]$^+$

B: 4-(4-(4-(1,1,1,3,3,3-Hexafluoro-2-hydroxypropan-2-yl)benzyl)piperazine-1-carbonyl)phenyl cyclopropylmethylcarbamate To a stirring solution of (4-(4-(1,1,1,3,3,3-hexafluoro-2-hydroxypropan-2-yl)benzyl)piperazin-1-yl)(4-hydroxyphenyl)methanone (0.195 mmol, 90 mg) in tetrahydrofuran (1 mL) was added triethylamine (0.584 mmol, 0.081 mL, 59.1 mg) and bis(4-nitrophenyl) carbonate (0.195 mmol, 59.2 mg). The reaction mixture was stirred at room temperature for 1 hour before the addition of cyclopropylmethanamine (0.389 mmol, 0.040 mL, 27.7 mg). The reaction was stirred at room temperature for a further 2 hours. The reaction mixture was concentrated under vacuum and the residue was dissolved in dichloromethane and purified by column chromatography (dichloromethane—5% methanol in dichloromethane) to afford title compound (19.9 mg).
MS (ESI) m/z 560.2 [M+H]$^+$

EXAMPLE 37

Methyl 1-(4-(3-(cyclopropylmethyl)ureido)benzoyl)-4-(4-(1,1,1,3,3,3-hexafluoro-2-hydroxypropan-2-yl)benzyl)piperazine-2-carboxylate

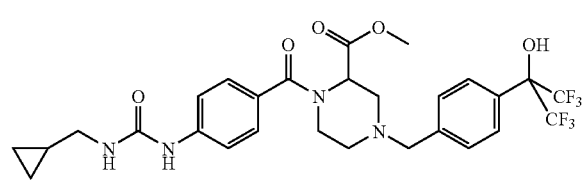 [SMILES: COC(=O)C1CN(Cc2ccc(C(O)(C(F)(F)F)C(F)(F)F)cc2)CCN1C(=O)c1ccc(NC(=O)NCC2CC2)cc1]

A: Methyl 4-(4-(1,1,1,3,3,3-hexafluoro-2-hydroxypropan-2-yl)benzyl)piperazine-2-carboxylate 2-(4-(Bromomethyl)phenyl)-1,1,1,3,3,3-hexafluoropropan-2-ol (4.61 mmol, 1.553 g), potassium carbonate (13.82 mmol, 1.910 g) and methyl piperazine-2-carboxylate dihydrochloride (4.61 mmol, 1 g) were combined and stirred at room temperature overnight in acetonitrile (25 mL). The reaction mixture was filtered and the solid washed with ethyl acetate. The organic was concentrated under reduced pressure. The resulting residue was purified by silica column chromatography (eluant dichloromethane/methanol/ammonia 95/5/0.5) to afford the title compound (464 mg).
MS (ESI) m/z 401.1 [M+H]$^+$

B: Methyl 1-(4-(3-(cyclopropylmethyl)ureido)benzoyl)-4-(4-(1,1,1,3,3,3-hexafluoro-2-hydroxypropan-2-yl)benzyl)piperazine-2-carboxylate 4-(3-(Cyclopropylmethyl)ureido)benzoic acid (0.213 mmol, 0.05 g), methyl 4-(4-(1,1,1,3,3,3-hexafluoro-2-hydroxypropan-2-yl)benzyl)piperazine-2-carboxylate (0.213 mmol, 0.085 g) and triethylamine (0.640 mmol, 0.089 mL, 0.065 g) were combined and stirred in dichloromethane. 1-Propanephosphonic acid cyclic anhydride (0.320 mmol, 0.191 mL, 0.204 g) was added and the reaction stirred for 2 hours at room temperature. This was washed with water and the resulting residue purified by acidic prep HPLC to afford the title compound (45 mg). MS (ESI) m/z 617.2 [M+H]$^+$

EXAMPLE 38

1-(4-(3-(Cyclopropylmethyl)ureido)benzoyl)-4-(4-(1,1,1,3,3,3-hexafluoro-2-hydroxypropan-2-yl)benzyl)piperazine-2-carboxylic acid

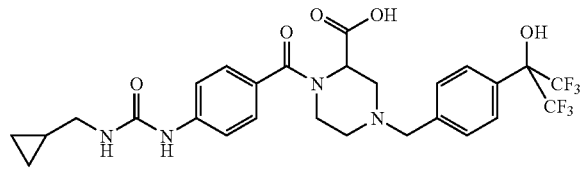 [SMILES: O=C(NCC1CC1)Nc1ccc(C(=O)N2CCN(Cc3ccc(C(O)(C(F)(F)F)C(F)(F)F)cc3)CC2C(=O)O)cc1]

Methyl 1-(4-(3-(cyclopropylmethyl)ureido)benzoyl)-4-(4-(1,1,1,3,3,3-hexafluoro-2-hydroxypropan-2-yl)benzyl)piperazine-2-carboxylate (0.032 mmol, 0.02 g) and sodium hydroxide (0.032 mmol, 1.298 mg) were combined and heated to 80° C. in methanol (1 mL) for 6 hours in a reactivial. The reaction mixture was concentrated under reduced pressure. The resulting residue was passed down an SCX column to afford the title compound (16 mg). MS (ESI) m/z 603.2 [M+H]$^+$

EXAMPLE 39

1-(Cyclopropylmethyl)-3-(4-(4-(4-(1,1,3,3,3-hexafluoro-2-hydroxypropan-2-yl)benzyl)-3-oxopiperazine-1-carbonyl)phenyl)urea

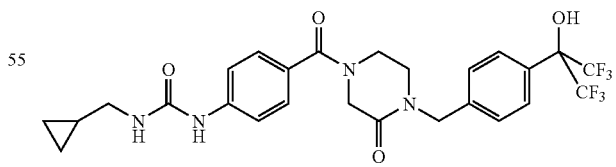

A: tert-Butyl 4-(4-(1,1,1,3,3,3-hexafluoro-2-hydroxypropan-2-yl)benzyl)-3-oxopiperazine-1-carboxylate To a stirring solution of tert-butyl 3-oxopiperazine-1-carboxylate (9.99 mmol, 2 g) in dry N-methyl-2-pyrrolidinone (2 mL) was added sodium hydride (30.0 mmol, 1.198 g). The mixture was stirred at room temperature under nitrogen for 20 min before the addition of 2-(4-(bromomethyl)phenyl)-1,1,1,3,3,3-hexafluoropropan-2-ol (10.99 mmol, 3.70 g). The mixture was stirred for a further 14 hours. The reaction mixture was diluted with ethyl acetate (100 mL) and washed with water (4×75 mL). The organic phase was dried over magnesium sulfate, filtered and the filtrate concentrated. The resulting residue was purified by column chromatography on silica gel (eluting with dichloromethane—3.5% methanol/96.5% dichloromethane gradient) to afford the title compound (1.44 g).
MS (ESI) m/z 457.4 [M+H]$^+$ B: 1-(4-(1,1,1,3,3,3-Hexafluoro-2-hydroxypropan-2-yl)benzyl)piperazin-2-one To a stirring solution of tert-butyl 4-(4-(1,1,1,3,3,3-hexafluoro-2-hydroxypropan-2-yl)benzyl)-3-oxopiperazine-1-carboxylate (3.05 mmol, 1.39 g) in dichloromethane (15 mL) was added trifluoroacetic acid (30.5 mmol, 3.47 g) and the mixture allowed to stir at room temperature for 5 hours. The reaction mixture was concentrated and the resulting residue purified by strong cation exchange column chromatography to afford the title compound (932 mg). MS (ESI) m/z 357.0 [M+H]$^+$ C: 1-(Cyclopropylmethyl)-3-(4-(4-(4-(1,1,1,3,3,3-hexafluoro-2-hydroxypropan-2-yl)benzyl)-3-oxopiperazine-1-carbonyl)phenyl)urea To a stirring solution of 4-(3-(cyclopropylmethyl)ureido)benzoic acid (0.337 mmol, 79 mg), 1-(4-(1,1,1,3,3,3-hexafluoro-2-hydroxypropan-2-yl)benzyl)piperazin-2-one (0.281 mmol, 100 mg) and triethylamine (0.842 mmol, 85 mg) in dichloromethane (10 ml) was added 1-propanephosphonic acid cyclic anhydride (0.421 mmol, 268 mg; 50% solution in ethyl acetate). The reaction mixture was stirred at room temperature for 2 hours. The reaction mixture was diluted with dichloromethane (20 mL) and washed with saturated aqueous sodium hydrogen carbonate solution (30 mL). The organic phase was concentrated and the resulting residue was purified by column chromatography on silica gel (eluting with 5% methanol/95% dichloromethane) to afford the title compound (36 mg). MS (ESI) m/z 573.0 [M+H]$^+$

EXAMPLE 40

1-(Cyclopropylmethyl)-3-(2-fluoro-4-(4-(4-(1,1,3,3,3-hexafluoro-2-hydroxypropan-2-yl)benzyl)-3-oxopiperazine-1-carbonyl)phenyl)urea

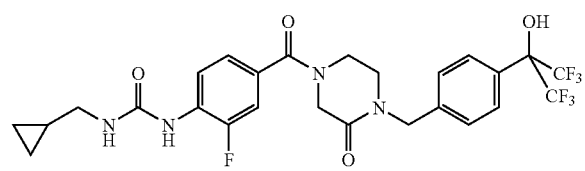 [SMILES: O=C(NCC1CC1)Nc1ccc(C(=O)N2CCN(Cc3ccc(C(O)(C(F)(F)F)C(F)(F)F)cc3)C(=O)C2)cc1F]

A: 4-(4-Amino-3-fluorobenzoyl)-1-(4-(1,1,1,3,3,3-hexafluoro-2-hydroxypropan-2-yl)benzyl)piperazin-2-one To a stirring solution of 4-amino-3-fluorobenzoic acid (1.965 mmol, 305 mg), 1-(4-(1,1,1,3,3,3-hexafluoro-2-hydroxypropan-2-yl)benzyl)piperazin-2-one (1.965 mmol, 700 mg) and triethylamine (5.89 mmol, 596 mg) in dichloromethane (10 mL) was added 1-propanephosphonic acid cyclic anhydride (2.95 mmol, 1876 mg; 50% solution in ethyl acetate). The reaction mixture was stirred at room temperature for 2 hours. The reaction mixture was diluted with dichloromethane (20 mL) and washed with saturated aqueous sodium hydrogen carbonate solution (30 mL). The organic phase was concentrated and the resulting residue was purified by column chromatography on silica gel (eluting with 50% ethyl acetate/50% dichloromethane—100% ethyl acetate gradient) to afford the title compound (550 mg). MS (ESI) m/z 492.3 [M–H]$^-$ B: 1-(Cyclopropylmethyl)-3-(2-fluoro-4-(4-(4-(1,1,1,3,3,3-hexafluoro-2-hydroxypropan-2-yl)benzyl)-3-oxopiperazine-1-carbonyl)phenyl)urea A solution of 4-(4-amino-3-fluorobenzoyl)-1-(4-(1,1,1,3,3,3-hexafluoro-2-hydroxypropan-2-yl)benzyl)piperazin-2-one (0.405 mmol, 200 mg) and 4-nitrophenyl carbonochloridate (0.405 mmol, 82 mg) in 1,4-dioxane (2 mL) was stirred at room temperature for 30 minutes. Cyclopropylmethanamine (0.405 mmol, 28.8 mg) and triethylamine (1.216 mmol, 123 mg) were added and the reaction stirred at room temperature overnight. The reaction mixture was diluted with dichloromethane (10 mL) and washed with saturated aqueous sodium hydrogen carbonate solution (10 mL). The organic phase was concentrated and the resulting residue was purified by column chromatography on silica gel (eliciting with 3% methanol/97% dichloromethane—10% methanol/90% dichloromethane gradient) to afford the title compound (45 mg).
MS (ESI) m/z 589.3 [M–H]

The following compounds were prepared in a similar manner:

40B: 1-(2-Fluoro-4-(4-(4-(1,1,1,3,3,3-hexafluoro-2-hydroxypropan-2-yl)benzyl)-3-oxopiperazine-1-carbonyl)phenyl)-3-(tetrahydro-2H-pyran-4-yl)urea

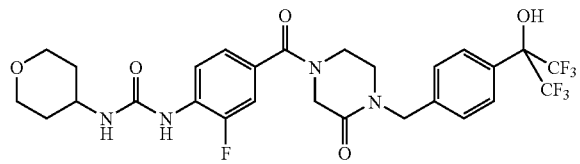 [SMILES: O=C(Nc1ccc(C(=O)N2CCN(Cc3ccc(C(O)(C(F)(F)F)C(F)(F)F)cc3)C(=O)C2)cc1F)NC1CCOCC1]

MS (ESI) m/z 619.5 [M–H]$^-$

40C: 1-(2-Fluoro-4-(4-(4-(1,1,1,3,3,3-hexafluoro-2-hydroxypropan-2-yl)benzyl)-3-oxopiperazine-1-carbonyl)phenyl)-3-(pyridazin-4-yl)urea

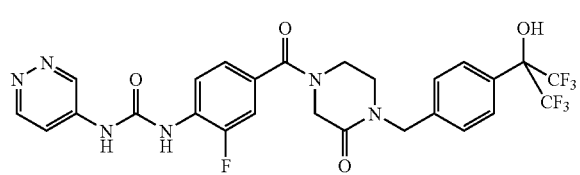 [SMILES: O=C(Nc1ccnnc1)Nc1ccc(C(=O)N2CCN(Cc3ccc(C(O)(C(F)(F)F)C(F)(F)F)cc3)C(=O)C2)cc1F]

MS (ESI) m/z 613.0 [M–H]$^-$

40D: 1-(2-Fluoro-4-(4-(4-(1,1,1,3,3,3-hexafluoro-2-hydroxypropan-2-yl)benzyl)-3-oxopiperazine-1-carbonyl)phenyl)-3-(pyrimidin-4-yl)urea

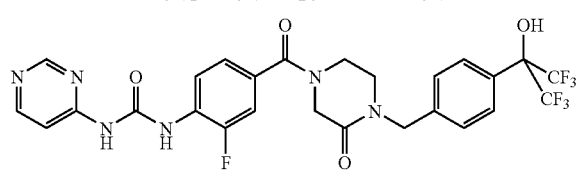 [SMILES: O=C(Nc1ccncn1)Nc1ccc(C(=O)N2CCN(Cc3ccc(C(O)(C(F)(F)F)C(F)(F)F)cc3)C(=O)C2)cc1F]

MS (ESI) m/z 615.2 [M+H]$^+$

EXAMPLE 41

1-(2-Fluoro-4-(4-(4-(1,1,1,1,3,3,3-hexafluoro-2-hydroxypropan-2-yl)benzyl)-3-oxopiperazine-1-carbonyl)phenyl)-3-(pyridin-4-yl)urea

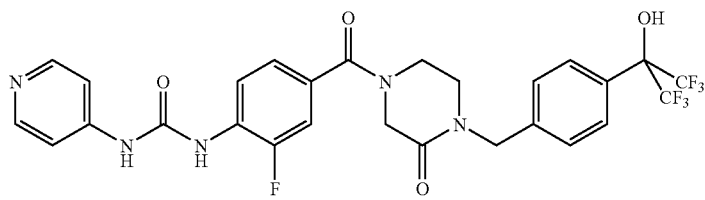 [SMILES: O=C(Nc1ccncc1)Nc1ccc(C(=O)N2CCN(Cc3ccc(C(O)(C(F)(F)F)C(F)(F)F)cc3)C(=O)C2)cc1F]

Step 1: A solution of pyridin-4-amine (2.125 mmol, 200 mg) and N-ethyl-N-isopropylpropan-2-amine (2.125 mmol, 27 mg) in dichloromethane (5 mL) was cooled to −78° C. Phenyl carbonochloridate (2.125 mmol, 333 mg) was added dropwise and the mixture allowed to warm to room temperature with stirring over 2 hours. The reaction mixture was diluted with dichloromethane (15 mL) and washed with saturated sodium hydrogen carbonate solution (10 mL). The organic phase was concentrated to give the intermediate phenyl pyridin-4-ylcarbamate.

Step 2: The intermediate phenyl pyridin-4-ylcarbamate (0.608 mmol, 130 mg) was dissolved in 1,4-dioxane (5 mL). 4-(4-Amino-3-fluorobenzoyl)-1-(4-(1,1,1,3,3,3-hexafluoro-2-hydroxypropan-2-yl)benzyl)piperazin-2-one (0.304 mmol, 150 mg) was added and the reaction mixture heated to 90° C. for 18 hours. The reaction mixture was concentrated and the resulting residue was purified by column chromatography on silica gel (eluting with 3% methanol/97% dichloromethane—15% methanol/90% dichloromethane gradient) to afford the title compound (40 mg). MS (ESI) m/z 612.2 [M−H]⁻

EXAMPLE 42

1-(Cyclopropylmethyl)-3-(4-(4-(4-(1,1,1,3,3,3-hexafluoro-2-hydroxypropan-2-yl)benzyl)piperazin-1-ylsulfonyl)phenyl)urea A: 2-(4-((4-(4-Aminophenylsulfonyl)piperazin-1-yl)methyl)phenyl)-1,1,1,3,3,3-hexafluoropropan-2-ol Step 1: 4-Nitrobenzene-1-sulfonyl chloride (0.23 g) was added to a solution of 1,1,1,3,3,3-hexafluoro-2-(4-(piperazin-1-ylmethyl)phenyl)propan-2-ol (0.5 g) in dry dichloromethane (10 mL) containing triethylamine (0.498 mmol, 0.15 mL, 0.050 g). The reaction was stirred for 15 minutes. Water (15 mL) was added, then the product was extracted into ethyl acetate (20 ml), washed with water (3×20 ml), dried over magnesium sulphate and concentrated under reduced pressure to afford the intermediate 1,1,1,3,3,3-hexafluoro-2-(4-((4-(4-nitrophenylsulfonyl)piperazin-1-yl)methyl)phenyl)propan-2-ol as a pale yellow gum (0.212 g).

Step 2: Iron (4.12 mmol, 0.23 g) (reduced powder) was added to a suspension of the intermediate 1,1,1,3,3,3-hexafluoro-2-(4-((4-(4-nitrophenylsulfonyl)piperazin-1-yl)methyl)phenyl)propan-2-ol (0.212 g) in isopropanol (10 mL) containing 5M hydrochloric acid (0.05 mL) and the mixture heated under reflux for 1.5 hours. The reaction was diluted with dichloromethane (20 mL), filtered through a pad of dicalite, dried over magnesium sulphate and concentrated under reduced pressure. The resulting light brown solid was dissolved in methanol and filtered through a silica carbonate column to yield the title compound. MS (ESI) m/z 498.0 [M+H]⁺

B: 1-(Cyclopropylmethyl)-3-(4-(4-(4-(1,1,1,3,3,3-hexafluoro-2-hydroxypropan-2-yl)benzyl)piperazin-1-ylsulfonyl)phenyl)urea 4-Nitrophenyl carbonochloridate (0.126 mmol, 0.02549 g) was added to a stirred solution of 2-(4-((4-(4-aminophenyl-

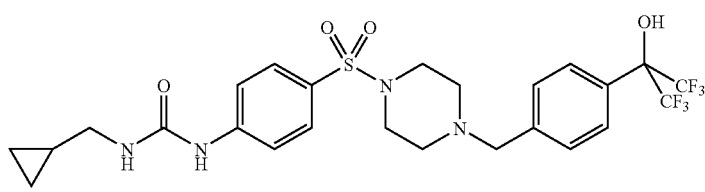 [SMILES: O=C(NCC1CC1)Nc1ccc(S(=O)(=O)N2CCN(Cc3ccc(C(O)(C(F)(F)F)C(F)(F)F)cc3)CC2)cc1]

sulfonyl)piperazin-1-yl)methyl)phenyl)-1,1,1,3,3,3-hexafluoropropan-2-ol (0.126 mmol, 0.0629 g) in dichloromethane (1 mL). After 1 hour, cyclopropylethanamine (0.380 mmol, 0.027 g) was added and stirring was continued for 1 hour. Water (5 mL) was added and the organic layer was separated, washed with water (3×10 mL), dried over magnesium sulphate and concentrated under reduced pressure to give a yellow gum. Purification was achieved by preparative HPLC, giving after filtration through a silica carbonate column in methanol, the title compound as a pale gum (15.2 mg). MS (ESI) m/z 595.0 [M+H]$^+$

EXAMPLE 43

1-(4-(4-(4-(1,1,1,1,3,3,3-hexafluoro-2-hydroxypropan-2-yl)benzyl)piperazin-1-yl)phenyl)-3-(pyridin-4-yl)urea

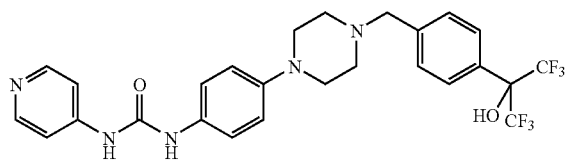 [SMILES: O=C(Nc1ccncc1)Nc1ccc(N2CCN(Cc3ccc(C(O)(C(F)(F)F)C(F)(F)F)cc3)CC2)cc1]

A: 1,1,1,3,3,3-Hexafluoro-2-(4-((4-(4-nitrophenyl)piperazin-1-yl)methyl)phenyl)propan-2-ol A mixture of 1-(4-nitrophenyl)piperazine (19.30 mmol, 4 g), 2-(4-(bromomethyl)-phenyl)-1,1,1,3,3,3-hexafluoropropan-2-ol (19.30 mmol, 6.51 g) and potassium carbonate (19.30 mmol, 2.67 g) in acetonitrile (10 mL) was refluxed for 20 hours and was then concentrated under reduced pressure. Dichloromethane was added and the insolubles were filtered off. The filtrate was chromatographed on silica eluting with a gradient of dichloromethane to dichloromethane/ethyl acetate (10%) to give the title compound (8 g).
MS (ESI) m/z 464.0 [M+H]$^+$ B: 2-(4-((4-(4-Aminophenyl)piperazin-1-yl)methyl)phenyl)-1,1,1,3,3,3-hexafluoropropan-2-ol To a stirred mixture of 1,1,1,3,3,3-hexafluoro-2-(4-((4-(4-nitrophenyl)piperazin-1-yl)methyl)phenyl)propan-2-ol (17.26 mmol, 8 g) and iron (143 mmol, 8 g) in 2-propanol was added 2M hydrochloric acid. The reaction was refluxed for 3 hours. The reaction was filtered through celite washing with 2-propanol and concentrated under reduced pressure. Water and ethyl acetate was added. Solid potassium carbonate was added until the aqueous layer was basic. The organic phase was separated and the water layer was extracted with dichloromethane. The combined organic phases were combined, dried (sodium sulfate) and concentrated under reduced pressure. The crude material was chromatographed on silica eluting with ethyl acetate. The brown solid obtained was stirred in ether and filtered to give the title compound (3.8 g). MS (ESI) m/z 434.1 [M+H]$^+$ C: 1-(4-(4-(4-(1,1,1,3,3,3-Hexafluoro-2-hydroxypropan-2-yl)benzyl)piperazin-1-yl)phenyl)-3-(pyridin-4-yl)urea 2-(4-((4-(4-Aminophenyl)piperazin-1-yl)methyl)phenyl)-1,1,1,3,3,3-hexafluoro-propan-2-ol (0.231 mmol, 0.1 g) and phenyl pyridin-4-ylcarbamate (0.346 mmol, 0.074 g) were combined in dioxane (1 mL) in a Reactivial and heated to 100° C. for 2 days. The reaction mixture was concentrated at reduced pressure. The resulting residue was taken up in dichloromethane, washed with water, dried over sodium sulphate and concentrated at reduced pressure. The residue was purified by silica chromatography (eluting with a solvent gradient from dichloromethane to 6% methanol/dichloromethane) to afford the title compound (43 mg). MS (ESI) m/z 555.2 [M+H]$^+$

EXAMPLE 44

Ethyl 4-(3-(4-(4-(4-(1,1,1,3,3,3-hexafluoro-2-hydroxypropan-2-yl)benzyl)piperazin-1-yl)phenyl)ureido)benzoate

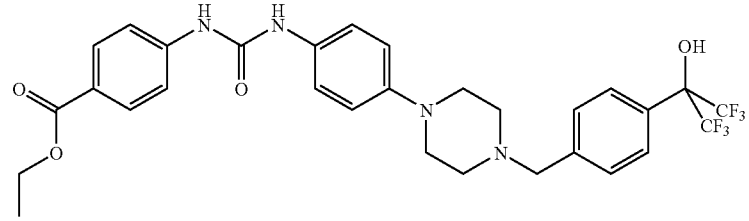 [SMILES: CCOC(=O)c1ccc(NC(=O)Nc2ccc(N3CCN(Cc4ccc(C(O)(C(F)(F)F)C(F)(F)F)cc4)CC3)cc2)cc1]

2-(4-((4-(4-Aminophenyl)piperazin-1-yl)methyl)phenyl)-1,1,1,3,3,3-hexafluoropropan-2-ol (0.461 mmol, 200 mg) and ethyl 4-isocyanatobenzoate (0.554 mmol, 0.060 mL, 106 mg) were combined in dichloromethane and heated in a microwave at 100° C. for 10 minutes. The reaction mixture was concentrated under vacuum. The residue was purified by acidic preparative HPLC and SCX chromatography to afford the title compound (212.3 mg). MS (ESI) m/z 625.2 [M+H]$^+$ The following compound was prepared in a similar manner:

44B: 1-(4-(4-(4-(1,1,1,3,3,3-Hexafluoro-2-hydroxypropan-2-yl)benzyl)piperazin-1-yl)phenyl)-3-phenylurea

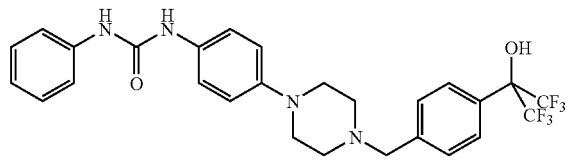 [SMILES: O=C(Nc1ccccc1)Nc1ccc(N2CCN(Cc3ccc(C(O)(C(F)(F)F)C(F)(F)F)cc3)CC2)cc1]

MS (ESI) m/z 553.5 [M+H]$^+$

EXAMPLE 45

4-(3-(4-(4-(4-(1,1,1,3,3,3-Hexafluoro-2-hydroxypropan-2-yl)benzylpiperazin-1-yl)phenyl)ureido)benzoic acid

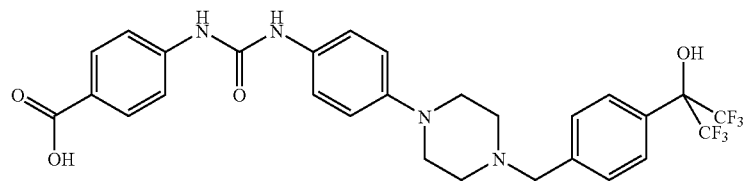 [SMILES: O=C(Nc1ccc(C(=O)O)cc1)Nc1ccc(N2CCN(Cc3ccc(C(O)(C(F)(F)F)C(F)(F)F)cc3)CC2)cc1]

Ethyl 4-(3-(4-(4-(4-(1,1,1,3,3,3-hexafluoro-2-hydroxypropan-2-yl)benzyl)piperazin-1-yl)phenyl)ureido)benzoate (0.315 mmol, 196.8 mg), and sodium hydroxide (0.315 mmol, 12.60 mg) were combined in ethanol (3 mL) and heated at 80° C. for 48 hours. The reaction mixture was concentrated under vacuum and the residue was partitioned between water and dichloromethane. The aqueous layer was separated and purified by SCX chromatography to obtain crude product. The crude product was further purified by acidic preparative HPLC and SCX chromatography to afford the title compound (55.3 mg). MS (ESI) m/z 597.2 [M+H]$^+$

EXAMPLE 46

1-(2-Fluoro-4-((4-(4-(1,1,1,3,3,3-hexafluoro-2-hydroxypropan-2-yl)benzyl)piperazin-1-yl)methyl)phenyl)-3-(pyridin-4-yl)urea

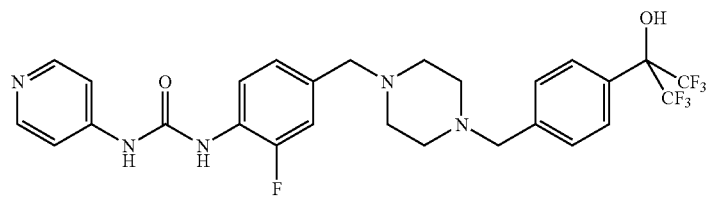 [SMILES: O=C(Nc1ccncc1)Nc1ccc(CN2CCN(Cc3ccc(C(O)(C(F)(F)F)C(F)(F)F)cc3)CC2)cc1F]

A: 2-(4-((4-(4-Amino-3-fluorobenzyl)piperazin-1-yl)methyl)phenyl)-1,1,1,3,3,3-hexafluoropropan-2-ol Borane tetrahydrofuran complex (13.05 mmol, 1.26 mL, 1.121 g) was added to a solution of (4-amino-3-fluorophenyl)(4-(4-(1,1,1,3,3,3-hexafluoro-2-hydroxypropan-2-yl)benzyl)piperazin-1-yl)methanone (1.043 mmol, 0.5 g) in tetrahydrofuran (8 mL) under nitrogen and the reaction heated to reflux for 5.5 hours. 5M Hydrochloric acid (10 mL) was added and the reaction was heated to reflux for 30 minutes, and then was cooled to ambient temperature. The product was extracted into dichloromethane (50 mL), washed with water (3×50 mL), dried over magnesium sulphate and concentrated under reduced pressure. The residue was purified by preparative HPLC affording the title compound (0.143 g). MS (ESI) m/z 466.0 [M+H]$^+$ B: 1-(2-Fluoro-4-((4-(4-(1,1,1,3,3,3-hexafluoro-2-hydroxypropan-2-yl)benzyl)piperazin-1-yl)methyl)phenyl)-3-(pyridin-4-yl)urea Phenyl pyridin-4-ylcarbamate (0.461 mmol, 0.099 g) was added to a stirred solution of 2-(4-((4-(4-amino-3-fluorobenzyl)piperazin-1-yl)methyl)phenyl)-1,1,1,3,3,3-hexafluoropropan-2-ol (0.279 mmol, 0.139) in dioxane (7 mL) and mixture heated in a microwave reactor for 10 minutes at 130°

C. Water (10 mL) was added to the reaction followed by dichloromethane (10 ml). The organic layer was separated, washed with water (3×10 mL), dried over magnesium sulphate and concentrated under reduced pressure. The residue was purified by preparative HPLC giving the title compound (0.023 g). MS (ESI) m/z 586.3 [M+H]$^+$

EXAMPLE 47

1-(Cyclopropylmethyl)-3-(4-(4-(4-(1,1,1,3,3,3-hexafluoro-2-hydroxypropan-2-yl)benzoyl)piperazine-1-carbonyl)phenyl)urea

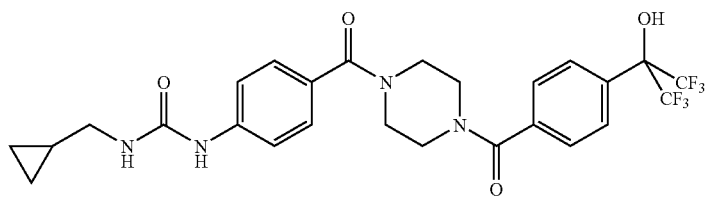 [SMILES: O=C(NCC1CC1)Nc1ccc(C(=O)N2CCN(C(=O)c3ccc(C(O)(C(F)(F)F)C(F)(F)F)cc3)CC2)cc1]

To a solution of 1-(cyclopropylmethyl)-3-(4-(piperazine-1-carbonyl)phenyl)urea (1.654 mmol, 500 mg), 4-(1,1,1,3,3,3-hexafluoro-2-hydroxypropan-2-yl)benzoic acid (1.654 mmol, 476 mg) and triethylamine (4.96 mmol, 0.691 mL, 502 mg) in dichloromethane (50 mL) was added 1-propanephosphonic acid cyclic anhydride (2.480 mmol, 0.738 mL, 789 mg; 50% solution in ethyl acetate). The reaction mixture was stirred for 2 hours then was diluted with ethyl acetate and sodium carbonate (aqueous). The organic layer was separated, dried (magnesium carbonate) and concentrated under reduced pressure. The residue was chromatographed on silica eluting with a gradient of dichloromethane to ethyl acetate to give the title compound (180 mg). MS (ESI) m/z 571.0 [M−H]−

EXAMPLE 48

1-(3-(4-(4-(1,1,1,3,3,3-Hexafluoro-2-hydroxypropan-2-yl)benzyl)piperazine-1-carbonyl)phenyl)-3-(pyridin-4-yl)urea

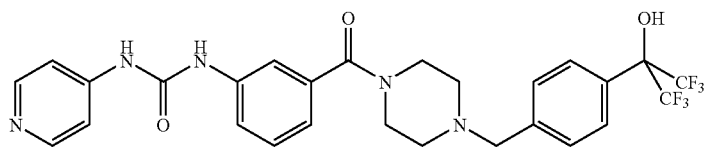 [SMILES: O=C(Nc1ccncc1)Nc1cccc(C(=O)N2CCN(Cc3ccc(C(O)(C(F)(F)F)C(F)(F)F)cc3)CC2)c1]

A: (4-(4-(1,1,1,3,3,3-Hexafluoro-2-hydroxypropan-2-yl)benzyl)piperazin-1-yl)(3-nitrophenyl)methanone To a stirred mixture of 1,1,1,3,3,3-hexafluoro-2-(4-(piperazin-1-ylmethyl)phenyl)-propan-2-ol (3.21 mmol, 1.1 g) and triethylamine (3.21 mmol, 0.448 mL, 0.325 g) in dichloromethane at 0° C. was added 3-nitrobenzoyl chloride (3.21 mmol, 0.596 g). The reaction was stirred at 0° C. for 2 hours then was allowed to warm to room temperature and stir overnight. The reaction was purified by chromatography on silica (eluting dichloromethane to dichloromethane/methanol) and SCX column chromatography to give the title compound (850 mg). MS (ESI) m/z 492.3 [M+H]+

B: (3-Aminophenyl)(4-(4-(1,1,1,3,3,3-hexafluoro-2-hydroxypropan-2-yl)benzylpiperazin-1-yl)methanone To a stirred suspension of (4-(4-(1,1,1,3,3,3-hexafluoro-2-hydroxypropan-2-yl)benzyl)piperazin-1-yl)(3-nitrophenyl)methanone (1.730 mmol, 850 mg) and iron powder (17.30 mmol, 966 mg) in 2-propanol was added a small volume of hydrochloric acid (37%). The reaction was refluxed for 1 hour then was allowed to cool to room temperature. The reaction was diluted with dichloromethane and solid potassium carbonated was added. The reaction was stirred for 1 hour then was filtered through celite washing with dichloromethane. The filtrate was concentrated under reduced pressure. The crude material was chromatographed on silica eluting with ethyl acetate to give the title compound (440 mg). MS (ESI) m/z 462.2 [M+H]+

C: 1-(3-(4-(4-(1,1,1,3,3,3-Hexafluoro-2-hydroxypropan-2-yl)benzyl)piperazine-1-carbonyl)phenyl)-3-(pyridin-4-yl)urea A mixture of phenyl pyridin-4-ylcarbamate (1.430 mmol, 306 mg) and (3-aminophenyl)(4-(4-(1,1,1,3,3,3-hexafluoro-2-hydroxypropan-2-yl)benzyl)piperazin-1-yl)methanone (0.954 mmol, 440 mg) in dioxane was heated in a Reactivial at 100° C. (heating block temperature) for 2 days. Chromatography on silica (eluting with a gradient of dichloromethane to dichloromethane/methanol) gave the title compound (200 mg).
MS (ESI) m/z 582.3 [M+H]+

EXAMPLE 49

1-(3-((4-(4-(1,1,1,3,3,3-Hexafluoro-2-hydroxypropan-2-yl)benzyl)piperazin-1-yl)methyl)phenyl)-3-(pyridin-4-yl)urea C: 1-(3-((4-(4-(1,1,1,3,3,3-Hexafluoro-2-hydroxypropan-2-yl)benzyl)piperazin-1-yl)methyl)phenyl)-3-(pyridin-4-yl)urea A mixture of phenyl pyridin-4-ylcarbamate (1.173 mmol, 251 mg) and 2-(4-((4-(3-aminobenzyl)piperazin-1-yl)methyl)phenyl)-1,1,1,3,3,3-hexafluoropropan-2-ol (0.782 mmol, 350 mg) in dioxane was heated in a Reactivial at 100° C. for 3 days. The reaction was then concentrated under reduced pressure. Chromatography on silica eluting with a

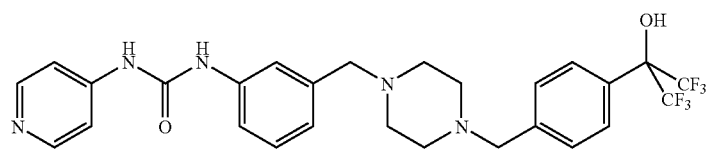 [SMILES: O=C(Nc1ccncc1)Nc1cccc(CN2CCN(Cc3ccc(C(O)(C(F)(F)F)C(F)(F)F)cc3)CC2)c1]

A: 1,1,1,3,3,3-Hexafluoro-2-(4-((4-(3-nitrobenzyl)piperazin-1-yl)methyl)phenyl)propan-2-ol To a stirred mixture of 1,1,1,3,3,3-hexafluoro-2-(4-(piperazin-1-ylmethyl)phenyl)-propan-2-ol (3.21 mmol, 1.1 g) and triethylamine (3.21 mmol, 0.448 ml, 0.325 g) in dichloromethane was added 1-(bromomethyl)-3-nitrobenzene (3.21 mmol, 0.694 g). The reaction was stirred for 20 hours gradient of dichloromethane to dichloromethane/methanol gave the title compound (100 mg). MS (ESI) m/z 568.5 [M+H]+

EXAMPLE 50

N-(Cyclopropylmethyl)-2-(4-(4-(4-(1,1,1,3,3,3-hexafluoro-2-hydroxypropan-2-yl)benzyl)piperazine-1-carbonyl)phenyl)acetamide

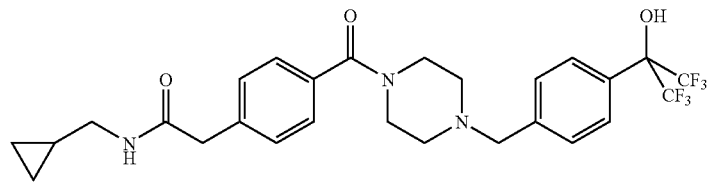 [SMILES: O=C(Cc1ccc(C(=O)N2CCN(Cc3ccc(C(O)(C(F)(F)F)C(F)(F)F)cc3)CC2)cc1)NCC1CC1]

then was diluted with dichloromethane and sodium hydrogen carbonate (aqueous). The organic layer was separated and poured onto a SCX column. The column was eluted with 2M ammonia in methanol and concentrated under reduced pressure to give the title compound (1 g). MS (ESI) m/z 478.1 [M+H]+

B: 2-(4-((4-(3-Aminobenzyl)piperazin-1-yl)methyl)phenyl)-1,1,1,3,3,3-hexafluoropropan-2-ol To a stirred suspension of 1,1,1,3,3,3-hexafluoro-2-(4-((4-(3-nitrobenzyl)piperazin-1-yl)methyl)phenyl)propan-2-ol (2.095 mmol, 1 g) and iron powder (20.95 mmol, 1.170 g) in 2-propanol was added a small volume of hydrochloric acid (37%). The reaction was refluxed for 2 hours then was allowed to cool to room temperature. The reaction was diluted with dichloromethane and solid potassium carbonate was added. The suspension was stirred for 18 hours then was filtered through celite. The filtrate was concentrated under reduced pressure then was purified by silica chromatography eluting with ethyl acetate to give the title compound (600 mg). MS (ESI) m/z 448.3 [M+H]+

A: Methyl 4-(2-(cyclopropylmethylamino)-2-oxoethyl)benzoate tert-Butyl piperazine-1-carboxylate (53.7 mmol, 10 g), 2-(4-(bromomethyl)phenyl)-1,1,1,3,3,3-hexafluoropropan-2-ol (53.7 mmol, 18.10 g), and potassium carbonate (107 mmol, 14.84 g) were combined in acetonitrile (50 mL) and the reaction mixture stirred at room temperature overnight. The reaction mixture was concentrated under vacuum and the resulting residue dissolved in dichloromethane. The solution was washed with water, and the organic layer was separated and concentrated under vacuum to afford the title compound (1.31 g). MS (ESI) m/z 248.2 [M+H]+

B: Sodium 4-(2-(cyclopropylmethylamino)-2-oxoethyl)benzoate

Methyl 4-(2-(cyclopropylmethylamino)-2-oxoethyl)benzoate (5.26 mmol, 1.3 g), and sodium hydroxide (5.26 mmol, 0.210 g) were combined in methanol (15 mL) and the reaction mixture was stirred and refluxed at 65° C. After 4 hours, an additional equivalent of sodium hydroxide (5.26 mmol, 0.210 g) was added and reaction mixture stirred and refluxed at 65°

C. overnight. The reaction mixture was concentrated under vacuum to afford the title compound (1.7 g). MS (ESI) m/z 234.0 [M+H]+

C: N-(Cyclopropylmethyl)-2-(4-(4-(4-(1,1,1,3,3,3-hexafluoro-2-hydroxypropan-2-yl)benzyl)piperazine-1-carbonyl)phenyl)acetamide Sodium 4-(2-(cyclopropylmethylamino)-2-oxoethyl)benzoate (5.26 mmol, 1.342 g), 1,1,1,3,3,3-hexafluoro-2-(4-(piperazin-1-ylmethyl)phenyl)propan-2-ol (5.26 mmol, 1.800 g), and triethylamine (18.40 mmol, 2.56 mL, 1.862 g) were combined in dichloromethane (25 mL) and the reaction mixture stirred at room temperature for 15 minutes. 1-Propanephosphonic acid cyclic anhydride (7.89 mmol, 4.69 ml, 5.02 g; 50% solution in ethyl acetate) was added dropwise and the reaction mixture stirred at room temperature for 1 hour. The reaction mixture was washed with water, and the organic layer was separated and concentrated under vacuum to obtain crude product. The crude product was purified by SCX column chromatography, silica column chromatography (eluting with 90:10:1 dichloromethane/methanol/ammonia) and acidic preparative HPLC to afford the title compound (55.3 mg). MS (ESI) m/z 558.2 [M+H]+

EXAMPLE 51

1-(Cyclopropylmethyl)-3-(4-(4-(4-(1,1,1,3,3,3-hexafluoro-2-hydroxypropan-2-yl)-2-Propylbenzyl)piperazine-1-carbonyl)phenyl)urea

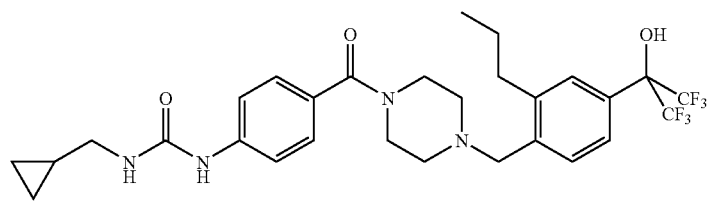 [SMILES: CCCc1cc(C(O)(C(F)(F)F)C(F)(F)F)ccc1CN1CCN(C(=O)c2ccc(NC(=O)NCC3CC3)cc2)CC1]

A: 2-(4-Amino-3-propylphenyl)-1,1,1,3,3,3-hexafluoropropan-2-ol

2-Propylaniline (111 mmol, 15 g), p-toluenesulfonic acid monohydrate (11.09 mmol, 2.110 g) and hexafluoroacetone trihydrate (111 mmol, 24.41 g) were combined and heated to 130° C. for 3 hours. The mixture was allowed to cool and diluted with ethyl acetate (250 mL). The solution was washed with sodium bicarbonate solution (3×100 mL), the organic phase was dried over magnesium sulfate, filtered and the filtrate was concentrated under reduced pressure. The resulting residue was allowed to crystallise overnight. The crystals were collected by filtration, washed with heptane (100 mL) and dried under vacuum to afford the title compound (14.3 g). MS (ESI) m/z 302.0 [M+H]+

B: 2-(4-Bromo-3-propylphenyl)-1,1,1,3,3,3-hexafluoropropan-2-ol 2-(4-Amino-3-propylphenyl)-1,1,1,3,3,3-hexafluoropropan-2-ol (33.2 mmol, 10 g) was dissolved in dioxane (15 mL) and water (30 mL) was added. The suspension was heated to reflux then hydrobromic acid (48% weight in water, 149 mmol, 17 mL) was added drop wise via an addition funnel over a 20 minute period. The mixture was heated for a further 20 minutes before cooling to 0° C. A solution of sodium nitrite (33.2 mmol, 2.290 g) in water (30 mL) was added to the mixture over a 30 minute period and the mixture stirred at 0° C. for 30 minutes. A solution of copper (I) bromide (38.2 mmol, 5.48 g) in water (30 mL) and hydrobromic acid (48% weight in water, 149 mmol, 17 mL) was added drop wise to the mixture over a 20 minute period at 0° C. and the mixture was allowed to stir at 0° C. for 20 minutes. The mixture was warmed to 60° C. for 20 minutes then allowed to stir at room temperature overnight. The reaction mixture was extracted with diethyl ether (3×100 mL), the organic phase was dried over magnesium sulfate, filtered and the filtrate was concentrated under vacuum. The resulting residue was purified by silica gel column chromatography (eluting with 10% ethyl acetate/90% heptane) to afford the title compound (6.1 g). MS (ESI) m/z 365.5 [M−H]

C: 4-(1,1,1,3,3,3-Hexafluoro-2-hydroxypropan-2-yl)-2-propylbenzaldehyde

To a nitrogen purged 3-necked flask was added 2-(4-bromo-3-propylphenyl)-1,1,1,3,3,3-hexafluoropropan-2-ol (2.74 mmol, 1 g) in anhydrous tetrahydrofuran (15 mL). The solution was cooled to −78° C. before the addition of n-butyl lithium in hexane (2.5M, 8.22 mmol, 3.29 mL). The mixture was stirred at −78° C. for 15 minutes before the drop wise addition of N,N-dimethylformamide (3.01 mmol, 0.220 g). The mixture was stirred at −78° C. for 10 minutes and was then allowed to warm to room temperature and stir for 30 minutes. The mixture was quenched with water (10 mL) and diluted with ethyl acetate (100 mL). The organic phase was separated, washed with water (2×50 mL), dried over magnesium sulfate, filtered and the filtrate was concentrated under reduced pressure. The resulting residue was purified by silica gel column chromatography (eluting with 10% ethyl acetate/90% heptane) to afford the title compound (4177 mg).

MS (ESI) m/z 313.3 [M−H]

D: 1,1,1,3,3,3-Hexafluoro-2-(4-(hydroxymethyl)-3-propylphenyl)propan-2-ol 4-(1,1,1,3,3,3-Hexafluoro-2-hydroxypropan-2-yl)-2-propylbenzaldehyde (0.636 mmol, 200 mg) was dissolved in methanol (4 mL)/dichloromethane (1 mL) and sodium borohydride (1.909 mmol, 72.2 mg) was added. The mixture was stirred at room temperature for 90 minutes then was concentrated under reduced pressure. The residue was dissolved in dichloromethane (50 mL) and washed with a saturated solution of sodium bicarbonate (25 mL). The organic phase was filtered through a hydrophobic frit and concentrated to afford the title compound (161 mg). MS (ESI) m/z 315.1 [M−H]

E: 1-(Cyclopropylmethyl)-3-(4-(4-(4-(1,1,1,3,3,3-hexafluoro-2-hydroxypropan-2-yl)-2-Propylbenzyl)piperazine-1-carbonyl)phenyl)urea 1,1,1,3,3,3-Hexafluoro-2-(4-(hydroxymethyl)-3-propylphenyl)propan-2-ol (0.509 mmol, 161 mg) was dissolved in dichloromethane (4 mL) and triethylamine (1.527 mmol, 155 mg) was added. The mixture was cooled to 0° C. before the addition of methanesulfonyl chloride (0.611 mmol, 70.0 mg). The mixture was stirred at 0° C. for 1 hour before warming to room temperature and stirring for 1 hour. The reaction mixture was diluted with dichloromethane (50 mL) and washed with water (2×10 mL). The organic phase was dried over magnesium sulfate, filtered and the filtrate was concentrated under reduced pressure. The resulting residue was dissolved in acetonitrile (4 mL) and 1-(cyclopropylmethyl)-3-(4-(piperazine-1-carbonyl)phenyl)urea (0.510 mmol, 154 mg) was added followed by potassium carbonate (1.529 mmol, 211 mg). The mixture was heated to reflux for 16 hours. The mixture was cooled, diluted with dichloromethane (50 mL) and washed with water (2×20 mL). The organic phase was dried over magnesium sulfate, filtered and the filtrate was concentrated under reduced pressure. The resulting residue was purified by HPLC and treated with strong cation exchange column chromatography to afford the title compound (63 mg). MS (ESI) m/z 601.3 [M+H]$^+$

EXAMPLE 52

1-(Cyclopropylmethyl)-3-(4-(4-((5-(1,1,1,3,3,3-hexafluoro-2-hydroxypropan-2-yl)thiazol-2-yl)methyl)piperazine-1-carbonyl)phenyl)urea

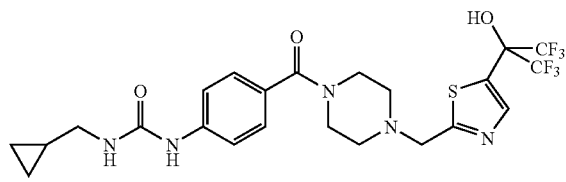 [SMILES: O=C(NCC1CC1)Nc1ccc(C(=O)N2CCN(Cc3ncc(C(O)(C(F)(F)F)C(F)(F)F)s3)CC2)cc1]

A: 2-(2-Aminothiazol-5-yl)-1,1,1,3,3,3-hexafluoropropan-2-ol

Thiazol-2-amine (150 mmol, 15 g), 4 Å powdered molecular sieves (1 g) and hexafluoroacetone trihydrate (300 mmol, 65.9 g) were combined and heated to 100° C. for 16 hours. The reaction mixture was cooled, diluted with ethyl acetate (200 mL) and filtered through celite. The filtrate was concentrated under reduced pressure to give a brown liquid which crystallised on standing. The solid was collected by filtration, washed with heptane (100 mL) then diethyl ether (50 mL) and dried under vacuum to afford the title compound (12.9 g). MS (ESI) m/z 266.7 [M+H]$^+$

B: 2-(2-Bromothiazol-5-yl)-1,1,1,3,3,3-hexafluoropropan-2-ol

To a stirring solution of copper (II) bromide (30.4 mmol, 6.80 g) in acetonitrile (100 mL) under nitrogen at 0° C. was added tert-butyl nitrite (33.5 mmol, 3.45 g). 2-(2-Aminothiazol-5-yl)-1,1,1,3,3,3-hexafluoropropan-2-ol (25.4 mmol, 6.75 g) in acetonitrile (40 mL) was then added portion wise and the mixture stirred at 0° C. for 30 minutes before warming to room temperature and stirring for 1 hour. The mixture was concentrated under reduced pressure and the resulting residue dissolved in ethyl acetate (150 mL). The solution was washed with 2M hydrochloric acid (3×75 mL), water (75 mL) and brine (75 mL). The organic phase was dried over magnesium sulfate, filtered and the filtrate was concentrated under reduced pressure. The resulting residue was purified by silica gel column chromatography (eluting with 10% ethyl acetate/90% heptane) to afford the title compound (7.1 g). MS (ESI) m/z 329.8 [M−H]$^-$

C: 5-(1,1,1,3,3,3-Hexafluoro-2-hydroxypropan-2-yl)thiazole-2-carbaldehyde

To a nitrogen purged three-necked flask was added n-butyl lithium in hexane (2.5M, 9.09 mmol, 3.64 mL) and diethyl ether (8 mL). The solution was cooled to −78° C. and 2-(2-bromothiazol-5-yl)-1,1,1,3,3,3-hexafluoropropan-2-ol (3.03 mmol, 1 g) in diethyl ether (7 mL) added drop wise over a period of 15 minutes. The mixture was stirred at −78° C. for 20 minutes before the drop wise addition of N,N-dimethylformamide (4.54 mmol, 0.332 g) in diethyl ether (4 mL). The mixture was stirred at −78° C. for 1 hour then was allowed to warm to −60° C. and stir for 1 hour. The mixture was slowly quenched with 4M hydrochloric acid at −60° C. and allowed to warm to room temperature. The mixture was extracted with diethyl ether (100 mL), washed with 4M hydrochloric acid (50 mL), followed by water (50 mL) and then brine (50 mL). The organic phase was dried over magnesium sulfate, filtered and the filtrate was concentrated under reduced pressure. The resulting residue was purified by silica gel column chromatography (eluting with a gradient of heptane to 50% ethyl acetate/50% heptane) to afford the title compound (500 mg). MS (ESI) m/z 278.0 [M−H]$^-$

D: 1,1,1,3,3,3-Hexafluoro-2-(2-(hydroxymethyl)thiazol-5-yl)propan-2-ol

To a stirring solution of 5-(1,1,1,3,3,3-hexafluoro-2-hydroxypropan-2-yl)thiazole-2-carbaldehyde (1.791 mmol, 500 mg) in methanol (4 mL) was added sodium borohydride (5.37 mmol, 203 mg). The mixture was stirred at room temperature for 90 minutes before concentrating under reduced pressure. The resulting residue was dissolved in dichloromethane (2 mL)/methanol (0.5 mL) and filtered through a plug of silica, washing with 20% methanol/80% dichloromethane. The filtrate was concentrated under reduced pressure to afford the title compound (150 mg). MS (ESI) m/z 280.0 [M−H]

E: 1-(Cyclopropylmethyl)-3-(4-(4-((5-(1,1,1,3,3,3-hexafluoro-2-hydroxypropan-2-yl)thiazol-2-yl)methyl)piperazine-1-carbonyl)phenyl)urea To a stirring solution of 1,1,1,3,3,3-hexafluoro-2-(2-(hydroxymethyl)thiazol-5-yl)propan-2-ol (0.533 mmol, 150 mg) and triethylamine (1.600 mmol, 162 mg) in dichloromethane (4 mL) at 0° C. was added methanesulfonyl chloride (0.533 mmol, 61.1 mg). The mixture was stirred at 0° C. for 1 hour before warming to room temperature and stirring for 1 hour. The reaction mixture was diluted with dichloromethane (50 mL) and washed with water (2×20 mL). The organic phase was dried over magnesium sulfate, filtered and the filtrate was concentrated under reduced pressure. The resulting residue was dissolved in acetonitrile (4 mL) and 1-(cyclopropylmethyl)-3-(4-(piperazine-1-carbonyl)phenyl)urea (0.635 mmol, 192 mg) was added followed by potassium carbonate (1.905 mmol, 263 mg). The mixture was heated to reflux for 6 hours then was cooled, diluted with dichloromethane (75 mL) and washed with water (2×20 mL). The organic phase was dried over magnesium sulfate, filtered and the filtrate was concentrated under reduced pressure. The resulting residue was purified by HPLC, strong cation exchange column chromatography and silica gel column chromatography (10% methanol/90% dichloromethane) to afford the title compound (1.5 mg).

MS (ESI) m/z 566.3 [M+H]+

EXAMPLE 53

1-(Cyclopropylmethyl)-3-(3-(4-(4-(1,1,1,3,3,3-hexafluoro-2-hydroxypropan-2-yl)benzyl)piperazin-1-ylsulfonyl)phenyl)urea

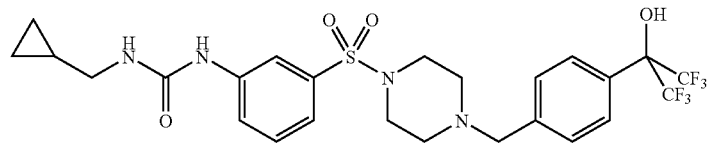 [SMILES: O=C(NCC1CC1)Nc1cccc(S(=O)(=O)N2CCN(Cc3ccc(C(O)(C(F)(F)F)C(F)(F)F)cc3)CC2)c1]

A: 1,1,1,3,3,3-Hexafluoro-2-(4-((4-(3-nitrophenylsulfonyl)piperazin-1-yl)methyl)phenyl)propan-2-ol 1,1,1,3,3,3-Hexafluoro-2-(4-(piperazin-1-ylmethyl)phenyl)propan-2-ol (2.366 mmol, 810 mg), 3-nitrobenzene-1-sulfonyl chloride (2.366 mmol, 524 mg) and pyridine (4.73 mmol, 0.383 mL, 374 mg) were combined in dichloromethane (20 mL) and stirred at room temperature for 1 hour. The reaction mixture was washed with water, and the organic layer was separated, dried and concentrated under vacuum. The residue was purified by SCX chromatography to afford the title compound (875.3 mg). MS (ESI) m/z 528.0 [M+H]+

B: 2-(4-((4-(3-Aminophenylsulfonyl)piperazin-1-yl)methyl)phenyl)-1,1,1,3,3,3-hexafluoropropan-2-ol 1,1,1,3,3,3-Hexafluoro-2-(4-((4-(3-nitrophenylsulfonyl)piperazin-1-yl)methyl)phenyl)propan-2-ol (1.660 mmol, 875.3 mg) and palladium on carbon were combined in ethyl acetate (20 mL). The reaction mixture was hydrogenated at 2 bar pressure for 1 hour. The reaction mixture was filtered through dicalite and concentrated under vacuum to afford the title compound (950.5 mg).

MS (ESI) m/z 498.0 [M+H]+

C: 1-(Cyclopropylmethyl)-3-(3-(4-(4-(1,1,1,3,3,3-hexafluoro-2-hydroxypropan-2-yl)benzyl)piperazin-1-ylsulfonyl)phenyl)urea 2-(4-((4-(3-Aminophenylsulfonyl)piperazin-1-yl)methyl)phenyl)-1,1,1,3,3,3-hexafluoropropan-2-ol (0.302 mmol, 150 mg) and 4-nitrophenyl carbonochloridate (0.302 mmol, 60.8 mg) were combined in a mixture of dichloromethane/dimethylformamide and stirred at room temperature for 1 hour. Cyclopropylmethanamine (0.603 mmol, 42.9 mg) was added and the reaction mixture was left to stir at room temperature for 15 minutes. The reaction mixture was purified by SCX chromatography and concentrated under vacuum. The residue was purified by silica column chromatography, eluting with 0%-4% methanol/dichloromethane gradient, to afford the title compound (52.3 mg).

MS (ESI) m/z 595.5 [M+H]+

EXAMPLE 54

Radioligand Competition Binding Scintillation Proximity Assay (SPA) Using Recombinant Human LXRα or LXRβ Protein These assays are used to evaluate the potency of compounds in their ability to compete with the binding of the agonist radioligand [$^3$H]T0901317. These assays utilise the purified ligand binding domain (LBD) of Liver X Receptor alpha (LXRα) or Liver X Receptor beta (LXRβ) fused to glutathione-5-transferase (GST) tagged protein (LXRα-LBD-GST and LXRβ-LBD-GST respectively) and scintillation proximity assay (SpA) technology to determine binding affinities (pKi) of compounds at the ligand binding domain (LBD) of the human nuclear hormone receptor LXRα or LXRβ.

Preparation of Recombinant Human LXRα and LXRβ

Human LXRα and LXRβ were expressed as GST-fusion proteins in *E. coli*. The LBD of LXRα or LXRβ was amplified by PCR and sub-cloned into the prokaryotic expression vector pGEX-4T-1 (GE Healthcare). Expression of LXRα or LXRβ from the pGEX-4T-1 plasmid in *E. Coli* resulted in the production of the recombinant glutathione-S-transferase (GST) LXRα-LBD or LXRβ-LBD fusion proteins. *E. coli*, containing either the LXRα or LXRβ pGEX-4T-1 plasmid, were propagated, induced, and harvested by centrifugation. The bacterial pellets were resuspended in lysis buffer containing 50 mM tris(Hydroxymethyl)aminomethane(TRIS)-pH 8.0, 100 mM Sodium Chloride (NaCl), 1 mM ethylenediaminetetraacetic acid (EDTA) and one tablet of Proteinase inhibitor cocktail complete/EDTA free (Roche) (per 50 mL of buffer). The mixtures were sonicated on ice with a Branson sonifier. The suspensions were centrifuged and dithiothreitol (DTT) added to the supernatants to obtain a final concentration of 25 mM. Recombinant human LXRα-LBD-GST or LXRβ-LBD-GST proteins were purified from the resulting supernatants by affinity chromatography on Glutathione-Sepharose Fast flow (Amersham), and the proteins eluted with buffer containing glutathione (50 mM tris pH 8.0, 2 mM DTT, 10 mM glutathione). Proteins were stored in 20 mM N-2-hydroxyethylpiperazine-N'-2-ethanesulfonic acid (HEPES), 2 mM DTT with 10% glycerol at −80° C.

Binding to LXRα or LXRβ LBDs

For LXRα or LXRβ assays, an aliquot of recombinant human LXRα-LBD-GST or LXRβ-LBD-GST protein was diluted to 0.5 µg/mL and incubated in a final volume of 100 µL SpA buffer (10 mM potassium hydrogen phosphate anhydrous [$K_2HPO_4$], 10 mM potassium Phosphate Monobasic [$KH_2PO_4$], 2 mM EDTA pH 7.1, 50 mM NaCl, 1 mM DTT, 2 mM 3-[(3-cholamidopropyl)dimethylammonio]-1-propanesulfonate (CHAPS)) containing Protein-A coupled scintillant filled YtSi SpA beads (GE Healthcare), to a final concentration of 1 mg/mL and Goat anti-GST antibody (GE Healthcare) to a final concentration of 5 μg/mL. T0901317 ($K_d$=10 nM) was used as a reference in each assay. To the assay mixture, 50 nM [$^3$H]T0901317 (50 Ci/mmol), ±test compound was added and the mixture incubated at 15° C. on a plate shaker for 2 hours. Test compounds were assayed over a concentration range. After incubation, the assay plates were read on a Packard TopCount. The pKi value for T0901317 in LXRα and LXRβ binding assays is: pKi=8.4±0.2. T0901317 at a concentration of 5 μM was used as the maximum binding control. Compounds of the invention show pKi values >5.0 or show >50% activity at 10M at LXRα and/or LXRP and preferred compounds show pKi values of >7 at LXRα and/or LXRβ, using these assay protocols.

LXRα and LXRβ Transactivation Assays

Intracellular agonist activity at LXRα and LXRβ was measured in vitro using recombinant chinese hamster ovary K1 (CHO.K1) cells stably expressing a natural estrogen responsive element (ERE)-containing luciferase reporter construct and either the human Estrogen receptor a (ERα)/LXRβ or ERα/LXRβ chimeric receptor protein respectively from a eukaryotic expression construct. The ERα/LXRβ and ERα/LXRβ chimeric receptor proteins contain the human LXRα or human LXRβ receptor LBD fused to the human ERα receptor DNA binding domain (DBD). In these assays compounds that can bind to the LBD of the human LXRα or LXRβ receptor, are able to activate the chimeric receptor protein intracellularly. Following activation, the ERα DBD can induce ERE-mediated luciferase expression via the natural ERE present in the rat oxytocin promoter luciferase construct (pROLUC). Using this system LXRα and LXRβ agonist-induced luciferase assays were generated using T0901317 as the agonist control.

Constructs

Expression constructs were prepared by inserting the ligand binding domain (LBD) of human LXRα or human LXRβ cDNA adjacent to the human ERα transcription factor DNA binding domain (DBD) to create pNGV1.ERα DBD-LXRαLBD and pNGVβ.ERαDBD-LXRβLBD. The pNGV1 mammalian expression construct (EMBL nucleotide sequence database file ASPNGV1, acc. #X99274) carries a selection marker for Neomycin (G418). The ERα responsive element of the rat oxytocin promoter (RO) was used to generate the promoter construct, pROLUC which contains several copies of the ERα response element (ERE) placed adjacent to the luciferase reporter gene. Construction of the promoter construct was based on the RO promoter region (position −363/+16) excised as a HindIII/MboI restriction enzyme fragment and linked to the firefly luciferase encoding sequence (Ivell and Richter., *Proc Natl Acad Sci USA*. 7: 2006-2010 (1984)). Stable CHO.K1 cell lines expressing pNGV1.ERαDBD-LXRαLBD or pNGV1.ERαDBD-LXRβLBD in combination with pROLUC were generated following transfection and selection of positive expressing clones using Neomycin. The best cell lines (CHO.K1LXRα and CHO.K1 LXRβ were selected on the basis of agonist window in response to 3 μM T0901317 and stability of response up to 20 passages.

Assay of Agonist Activity of Test Compounds in LXRα and LXRβ Transactivation Assays For LXRα and LXRβ transactivation assays CHO.K1 LXRα or CHO.K1 LXRβ cells respectively were seeded at a density of 25000 cells/well in 96 well plates in 200 μL of Dulbecco's Modified Eagle Medium (phenol red free) containing 5% charcoal treated bovine calf serum at 37° C. in a humidified atmosphere of 5% $CO_2$. After 6 hours post-seeding, compounds were characterised by incubation with cells for 16 hours across a concentration range. T0901317 at a concentration of 3 μM was used as the maximum agonist control in each assay. Luciferase activity was determined using a Luciferase assay kit (Perkin Elmer). Determination of luciferase activity was initiated by addition of lysis buffer to each well and light emission measured using a Packard Topcount reader. The $pEC_{50}$ values for T0901317 in the LXRα and LXRβ transactivation assays are: $pEC_{50}$=7.3±0.2 and 7.4±0.2 respectively. Agonist activities of test compounds were compared against the maximum agonist control. Preferred compounds of the invention were shown to have LXRα and/or LXRβ agonist activity using these assay protocols.

The invention claimed is:

1. A hexafluoroisopropanol derivative having the general Formula I

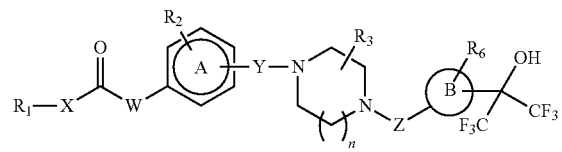

Formula I wherein

B represents a five or six membered aromatic ring which is substituted at a carbon atom by a hexafluoroisopropanol moiety, the ring optionally comprising one or two nitrogens, sulphur or oxygen;

n is 1 or 2;

Z is $CH_2$ or CO;

Y is CO, $SO_2$, $CH_2$ or a bond; and can be of meta or para substitution pattern;

A is a 6-membered aromatic ring optionally containing 1 or 2 nitrogen atoms;

X is $NR_4$, O or a bond;

W is NH, O or $CH_2$;

$R_1$ is $(C_{1-8})$alkyl, $(C_{3-8})$cycloalkyl or $(C_{3-8})$cycloalkyl $(C_{(1-4)})$alkyl, each of the alkyl groups being optionally substituted with hydroxyl, hydroxymethyl, $(C_{1-3})$alkyloxy, cyano, halogen, $CF_3$, $NR_7R_8$, $NR_7R_8CO$ or $R_9OCO$; or $R_1$ is 5- or 6-membered aromatic ring, optionally comprising 1-3 heteroatoms selected from O, S and N, the ring being optionally substituted by $(C_{1-3})$alkyl, $(C_{3-6})$cycloalkyl, $(C_{1-3})$alkyloxy, $(C_{1-3})$alkylsulfonyl, cyano, $CF_3$, $OCF_3$, halogen or $R_9OCO$, and the ring being optionally linked to X via a $(C_{1-3})$alkylene group which is optionally substituted by hydroxyl; or $R_1$ is a 5- or 6-membered saturated or unsaturated heterocyclic ring, comprising 1 or 2 heteroatoms selected from $NR_{10}$, O, S, SO and $SO_2$, the ring being optionally substituted by $(C_{1-3})$alkyl, hydroxyl, oxo, $NR_{11}R_{12}CH_2$ or $R_9OCO$, and the ring being optionally linked to X via a $(C_{1-3})$alkylene group which is optionally substituted by hydroxyl; or when X is $NR_4$, $R_1$, may together with $R_4$ and the N to which they are bonded form a 4-8 membered ring, which can be optionally substituted with hydroxyl or hydroxymethyl;

$R_2$ optionally represents 1-3 substituents independently selected from $(C_{1-4})$alkyl, $(C_{1-4})$alkyloxy, $CF_3$, $OCF_3$ and halogen;

R₃ optionally represents 1-4 substituents independently selected from $(C_{1-4})$alkyl and $(C_{1-4})$alkyl substituted by OH or 1 or more halogens; or R₃ represents oxo or COOR₅;

R₄, when present is H or $(C_{1-3})$alkyl;

R₅, when present is H or $(C_{1-3})$alkyl;

R₆, when present is H or $(C_{1-3})$alkyl;

R₇ and R₈, when present, are independently H, $(C_{1-3})$alkyl or $(C_{3-5})$cycloalkyl;

R₉, when present, is H, $(C_{1-3})$alkyl or $(C_{3-5})$cycloalkyl $(C_{1-3})$alkyl;

R₁₀, when present, is H, $(C_{1-3})$alkyl or CO$(C_{1-3})$alkyl;

R₁₁, and R₁₂, when present, are independently H or $(C_{1-3})$alkyl;

or a pharmaceutically acceptable salt thereof.

2. The hexafluoroisopropanol derivative of claim 1, wherein B represents substituted phenyl.

3. The hexafluoroisopropanol derivative of claim 2, wherein Z is CH₂, Y is CO, W is NH, X is NH and n is 1.

4. The hexafluoroisopropanol derivative of claim 3, wherein in addition A is a phenyl ring and Y and W are in para-position to each other.

5. The hexafluoroisopropanol derivative of claim 3, wherein R₂ represents F or Cl ortho to the W=NH-position; and wherein R₃ and R₆ are absent.

6. The hexafluoroisopropanol derivative of claim 1 which is selected from:

1-(cyclopropylmethyl)-3-(4-(4-(4-(1,1,1,3,3,3-hexafluoro-2-hydroxypropan-2-yl)benzyl)-piperazine-1-carbonyl)phenyl)urea;

1-butyl-3-(4-(4-(4-(1,1,1,3,3,3-hexafluoro-2-hydroxypropan-2-yl)benzyl)piperazine-1-carbonyl)-phenyl)urea;

1-(4-(4-(4-(1,1,1,3,3,3-hexafluoro-2-hydroxypropan-2-yl)benzyl)piperazine-1-carbonyl)phenyl)-3-isobutylurea;

1-cyclobutyl-3-(4-(4-(4-(1,1,1,3,3,3-hexafluoro-2-hydroxypropan-2-yl)benzyl)piperazine-1-carbonyl)phenyl)urea;

1-(2-fluoro-4-(4-(4-(1,1,1,3,3,3-hexafluoro-2-hydroxypropan-2-yl)benzyl)piperazine-1-carbonyl)phenyl)-3-(2-hydroxy-2-methylpropyl)urea;

1-(2-fluoro-4-(4-(4-(1,1,1,3,3,3-hexafluoro-2-hydroxypropan-2-yl)benzyl)piperazine-1-carbonyl)phenyl)-3-(3-hydroxy-3-methylbutyl)urea;

1-(cyclopropylmethyl)-3-(2-fluoro-4-(4-(4-(1,1,1,3,3,3-hexafluoro-2-hydroxypropan-2-yl)benzyl)piperazine-1-carbonyl)phenyl)urea;

(S)-1-(2-fluoro-4-(4-(4-(1,1,1,3,3,3-hexafluoro-2-hydroxypropan-2-yl)benzyl)-piperazine-1-carbonyl)phenyl)-3-(2-hydroxypropyl)urea;

(R)-1-(2-fluoro-4-(4-(4-(1,1,1,3,3,3-hexafluoro-2-hydroxypropan-2-yl)benzyl)-piperazine-1-carbonyl)phenyl)-3-(2-hydroxypropyl)urea;

1-(2-fluoro-4-(4-(4-(1,1,1,3,3,3-hexafluoro-2-hydroxypropan-2-yl)benzyl)piperazine-1-carbonyl)phenyl)-3-((1-hydroxycyclopropyl)methyl)urea;

(S)-1-(2-fluoro-4-(4-(4-(1,1,1,3,3,3-hexafluoro-2-hydroxypropan-2-yl)benzyl)-piperazine-1-carbonyl)phenyl)-3-(1-hydroxy-3-methylbutan-2-yl)urea;

1-(2-fluoro-4-(4-(4-(1,1,1,3,3,3-hexafluoro-2-hydroxypropan-2-yl)benzyl)piperazine-1-carbonyl)phenyl)-3-(4-hydroxycyclohexyl)urea, trans;

(S)-1-(2-fluoro-4-(4-(4-(1,1,1,3,3,3-hexafluoro-2-hydroxypropan-2-yl)benzyl)-piperazine-1-carbonyl)phenyl)-3-(1-hydroxypentan-2-yl)urea;

1-(2-chloro-4-(4-(4-(1,1,1,3,3,3-hexafluoro-2-hydroxypropan-2-yl)benzyl)piperazine-1-carbonyl)phenyl)-3-(2-hydroxy-2-methylpropyl)urea;

(S)-1-(2-chloro-4-(4-(4-(1,1,1,3,3,3-hexafluoro-2-hydroxypropan-2-yl)benzyl)-piperazine-1-carbonyl)phenyl)-3-(2-hydroxypropyl)urea;

(R)-1-(2-chloro-4-(4-(4-(1,1,1,3,3,3-hexafluoro-2-hydroxypropan-2-yl)benzyl)-piperazine-1-carbonyl)phenyl)-3-(2-hydroxypropyl)urea;

1-(2-chloro-4-(4-(4-(1,1,1,3,3,3-hexafluoro-2-hydroxypropan-2-yl)benzyl)piperazine-1-carbonyl)phenyl)-3-(3-hydroxy-3-methylbutyl)urea;

1-(2-chloro-4-(4-(4-(1,1,1,3,3,3-hexafluoro-2-hydroxypropan-2-yl)benzyl)piperazine-1-carbonyl)phenyl)-3-((1-hydroxycyclopropyl)methyl)urea; and 1-(2-chloro-4-(4-(4-(1,1,1,3,3,3-hexafluoro-2-hydroxypropan-2-yl)benzyl)piperazine-1-carbonyl)phenyl)-3-(4-hydroxycyclohexyl)urea, trans;

1-(2-amino-2-methylpropyl)-3-(2-fluoro-4-(4-(4-(1,1,1,3,3,3-hexafluoro-2-hydroxypropan-2-yl)benzyl)piperazine-1-carbonyl)phenyl)urea;

1-(2-fluoro-4-(4-(4-(1,1,1,3,3,3-hexafluoro-2-hydroxypropan-2-yl)benzyl)piperazine-1-carbonyl)phenyl)-3-((1S,2R)-2-hydroxycyclopentyl)urea;

1-(2-fluoro-4-(4-(4-(1,1,1,3,3,3-hexafluoro-2-hydroxypropan-2-yl)benzyl)piperazine-1-carbonyl)phenyl)-3-(3-hydroxycyclobutyl)urea, trans;

1-(2-fluoro-4-(4-(4-(1,1,1,3,3,3-hexafluoro-2-hydroxypropan-2-yl)benzyl)piperazine-1-carbonyl)phenyl)-3-((1-hydroxycyclobutyl)methyl)urea;

1-(2-(dimethylamino)-2-methylpropyl)-3-(2-fluoro-4-(4-(4-(1,1,1,3,3,3-hexafluoro-2-hydroxypropan-2-yl)benzyl)piperazine-1-carbonyl)phenyl)urea;

1-(2-fluoro-4-(4-(4-(1,1,1,3,3,3-hexafluoro-2-hydroxypropan-2-yl)benzyl)piperazine-1-carbonyl)phenyl)-3-(3,3,3-trifluoro-2-hydroxypropyl)urea;

1-(2-fluoro-4-(4-(4-(1,1,1,3,3,3-hexafluoro-2-hydroxypropan-2-yl)benzyl)piperazine-1-carbonyl)phenyl)-3-(tetrahydro-2H-pyran-4-yl)urea;

(R)-1-(2-fluoro-4-(4-(4-(1,1,1,3,3,3-hexafluoro-2-hydroxypropan-2-yl)benzyl)piperazine-1-carbonyl)phenyl)-3-(2-hydroxy-2-phenylethyl)urea;

(S)-1-(2-fluoro-4-(4-(4-(1,1,1,3,3,3-hexafluoro-2-hydroxypropan-2-yl)benzyl)piperazine-1-carbonyl)phenyl)-3-(2-hydroxy-2-phenylethyl)urea;

(S)-1-(2-fluoro-4-(4-(4-(1,1,1,3,3,3-hexafluoro-2-hydroxypropan-2-yl)benzyl)-piperazine-1-carbonyl)phenyl)-3-(6-oxopiperidin-3-yl)urea;

1-(2-fluoro-4-{4-[4-(2,2,2-trifluoro-1-hydroxy-1-trifluoromethyl-ethyl)-benzyl]-piperazine-1-carbonyl}-phenyl)-3-(4-hydroxy-1,1-dioxo-tetrahydro-1$\lambda^6$-thiophen-3-yl)-urea, cis racemate;

1-(1,1-dioxo-tetrahydro-1$\lambda^6$-thiophen-3-yl)-3-(2-fluoro-4-{4-[4-(2,2,2-trifluoro-1-hydroxy-1-trifluoromethyl-ethyl)-benzyl]-piperazine-1-carbonyl}-phenyl)-urea;

(R)-1-(2-fluoro-4-(4-(4-(1,1,1,3,3,3-hexafluoro-2-hydroxypropan-2-yl)benzyl)-piperazine-1-carbonyl)phenyl)-3-(tetrahydrofuran-3-yl)urea;

1-(1,1-dioxo-hexahydro-1$\lambda^6$-thiopyran-4-yl)-3-(2-fluoro-4-{4-[4-(2,2,2-trifluoro-1-hydroxy-1-trifluoromethyl-ethyl)-benzyl]-piperazine-1-carbonyl}-phenyl)-urea;

1-(2-fluoro-4-(4-(4-(1,1,1,3,3,3-hexafluoro-2-hydroxypropan-2-yl)benzyl)piperazine-1-carbonyl)phenyl)-3-((4-hydroxytetrahydro-2H-pyran-4-yl)methyl)urea;

(S)-1-(2-fluoro-4-(4-(4-(1,1,1,3,3,3-hexafluoro-2-hydroxypropan-2-yl)benzyl)-piperazine-1-carbonyl)phenyl)-3-(tetrahydrofuran-3-yl)urea;

1-(2-fluoro-4-(4-(4-(1,1,1,3,3,3-hexafluoro-2-hydroxypropan-2-yl)benzyl)piperazine-1-carbonyl)phenyl)-3-(4-hydroxytetrahydrofuran-3-yl)urea, cis racemate;
1-(2-fluoro-4-(4-(4-(1,1,1,3,3,3-hexafluoro-2-hydroxypropan-2-yl)benzyl)piperazine-1-carbonyl)phenyl)-3-((1S,2R)-2-hydroxycyclohexyl)urea, cis racemate;
1-(2-fluoro-4-(4-(4-(1,1,1,3,3,3-hexafluoro-2-hydroxypropan-2-yl)benzyl)piperazine-1-carbonyl)phenyl)-3-(2-hydroxybutyl)urea, racemate;
1-(2-chloro-4-{4-[4-(2,2,2-trifluoro-1-hydroxy-1-trifluoromethyl-ethyl)-benzyl]-piperazine-1-carbonyl}-phenyl)-3-(4-hydroxy-1,1-dioxo-tetrahydro-1λ⁶-thiophen-3-yl)-urea, cis racemate;
1-(5-tert-butylisoxazol-3-yl)-3-(2-fluoro-4-(4-(4-(1,1,1,3,3,3-hexafluoro-2-hydroxypropan-2-yl)benzyl)piperazine-1-carbonyl)phenyl)urea;
1-(2-fluoro-4-(4-(4-(1,1,1,3,3,3-hexafluoro-2-hydroxypropan-2-yl)benzyl)piperazine-1-carbonyl)phenyl)-3-(2-methylpyridin-4-yl)urea;
1-(2-fluoro-4-(4-(4-(1,1,1,3,3,3-hexafluoro-2-hydroxypropan-2-yl)benzyl)piperazine-1-carbonyl)phenyl)-3-(2-(trifluoromethyl)pyridin-4-yl)urea;
1-(2-fluoro-4-(4-(4-(1,1,1,3,3,3-hexafluoro-2-hydroxypropan-2-yl)benzyl)piperazine-1-carbonyl)phenyl)-3-(5-methylisoxazol-3-yl)urea;
1-(2-fluoro-4-(4-(4-(1,1,1,3,3,3-hexafluoro-2-hydroxypropan-2-yl)benzyl)piperazine-1-carbonyl)phenyl)-3-(3-fluoropyridin-4-yl)urea;
1-(2-fluoro-4-(4-(4-(1,1,1,3,3,3-hexafluoro-2-hydroxypropan-2-yl)benzyl)piperazine-1-carbonyl)phenyl)-3-(1,3,4-thiadiazol-2-yl)urea;
1-(2-fluoro-4-(4-(4-(1,1,1,3,3,3-hexafluoro-2-hydroxypropan-2-yl)benzyl)piperazine-1-carbonyl)phenyl)-3-(pyridin-4-yl)urea;
1-(2-fluoro-4-(4-(4-(1,1,1,3,3,3-hexafluoro-2-hydroxypropan-2-yl)benzyl)piperazine-1-carbonyl)phenyl)-3-(isoxazol-3-yl)urea;
1-(5-cyanothiazol-2-yl)-3-(2-fluoro-4-(4-(4-(1,1,1,3,3,3-hexafluoro-2-hydroxypropan-2-yl)benzyl)piperazine-1-carbonyl)phenyl)urea;
1-(2-fluoro-4-(4-(4-(1,1,1,3,3,3-hexafluoro-2-hydroxypropan-2-yl)benzyl)piperazine-1-carbonyl)phenyl)-3-(isoxazol-4-yl)urea;
1-(2-fluoro-4-(4-(4-(1,1,1,3,3,3-hexafluoro-2-hydroxypropan-2-yl)benzyl)piperazine-1-carbonyl)phenyl)-3-(pyridin-2-yl)urea;
1-(2-fluoro-4-(4-(4-(1,1,1,3,3,3-hexafluoro-2-hydroxypropan-2-yl)benzyl)piperazine-1-carbonyl)phenyl)-3-(3-methylisoxazol-5-yl)urea;
1-(2-fluoro-4-(4-(4-(1,1,1,3,3,3-hexafluoro-2-hydroxypropan-2-yl)benzyl)piperazine-1-carbonyl)phenyl)-3-(3-methyl-1,2,4-oxadiazol-5-yl)urea;
1-(2-fluoro-4-(4-(4-(1,1,1,3,3,3-hexafluoro-2-hydroxypropan-2-yl)benzyl)piperazine-1-carbonyl)phenyl)-3-(pyridin-3-yl)urea;
1-(2-fluoro-4-(4-(4-(1,1,1,3,3,3-hexafluoro-2-hydroxypropan-2-yl)benzyl)piperazine-1-carbonyl)phenyl)-3-(pyrazin-2-yl)urea;
1-(2-fluoro-4-{4-[4-(2,2,2-trifluoro-1-hydroxy-1-trifluoromethyl-ethyl)-benzyl]-piperazine-1-carbonyl}-phenyl)-3-(1-oxo-tetrahydro-thiopyran-4-yl)-urea; and
1-(2-fluoro-4-{4-[4-(2,2,2-trifluoro-1-hydroxy-1-trifluoromethyl-ethyl)-benzyl]-piperazine-1-carbonyl}-phenyl)-3-(1-oxo-tetrahydro-thiophen-3-yl)-urea;
or a pharmaceutically acceptable salt thereof.

7. A pharmaceutical composition comprising a hexafluoroisopropanol derivative of claim 1, or a pharmaceutically acceptable salt thereof, and one or more and pharmaceutically acceptable auxiliaries.

8. A pharmaceutical composition comprising a hexafluoroisopropanol derivative of claim 6, or a pharmaceutically acceptable salt thereof, and one or more pharmaceutically acceptable auxiliaries.

9. A method for treating atherosclerosis in a patient in need thereof, the method comprising administering to the patient an effective amount of the hexafluoroisopropanol derivative of claim 1 or a pharmaceutically acceptable salt thereof.

10. A method for treating a disorder selected from the group consisting of hypercholesterolemia, cholesterol gallstones, type II diabetes and obesity, in a patient in need thereof, the method comprising administering to the patient an effective amount of the hexafluoroisopropanol derivative of claim 1 or a pharmaceutically acceptable salt thereof.

11. A method for treating atherosclerosis in a patient in need thereof, the method comprising administering to the patient an effective amount of the hexafluoroisopropanol derivative of claim 6 or a pharmaceutically acceptable salt thereof.

12. A method for treating a disorder selected from the group consisting of hypercholesterolemia, cholesterol gallstones, type II diabetes and obesity, in a patient in need thereof, the method comprising administering to the patient an effective amount of the hexafluoroisopropanol derivative of claim 6 or a pharmaceutically acceptable salt thereof.

* * * * *